US005258527A

United States Patent [19]

Krauskopf et al.

[11] Patent Number: 5,258,527

[45] Date of Patent: Nov. 2, 1993

[54] INSECTICIDAL, ACARICIDAL AND HERBICIDAL 1-H-3-ARYL-PYRROLIDINE-2,4-DIONE DERIVATIVES

[75] Inventors: Birgit Krauskopf; Klaus Lürssen, both of Bergisch Gladbach; Hans-Joachim Santel, Leverkusen; Robert R. Schmidt, Bergisch Gladbach; Ulrike Wachendorff-Neumann; Reiner Fischer, both of Monheim; Christoph Erdelen, Leichlingen, all of Fed. Rep. of Germany

[73] Assignee: Bayer Aktiengesellschaft, Leverkusen, Fed. Rep. of Germany

[21] Appl. No.: 693,205

[22] Filed: Apr. 30, 1991

[30] Foreign Application Priority Data

May 10, 1990 [DE] Fed. Rep. of Germany ....... 4014941
Mar. 8, 1991 [DE] Fed. Rep. of Germany ....... 4107394

[51] Int. Cl.[5] .................... A01N 37/32; A01N 43/36; C07D 207/36; C07D 207/416

[52] U.S. Cl. .................................... 548/543; 504/283

[58] Field of Search ........................ 548/543; 504/283; 514/425

[56] References Cited

U.S. PATENT DOCUMENTS 3,272,842 9/1966 Easton et al. .................... 260/326.5
4,632,698 12/1986 Wheeler ............................... 71/106

FOREIGN PATENT DOCUMENTS 0377893 12/1989 European Pat. Off. .
0415185 8/1990 European Pat. Off. .
0423482 9/1990 European Pat. Off. .
2361084 12/1973 Fed. Rep. of Germany .
8804652 12/1987 PCT Int'l Appl. .

*Primary Examiner*—David B. Springer
*Attorney, Agent, or Firm*—Sprung Horn Kramer & Woods

[57] ABSTRACT

Insecticidal, acaricidal and herbicidal 1-H-3-aryl-pyrrolidine-2,4-dione derivatives of the formula

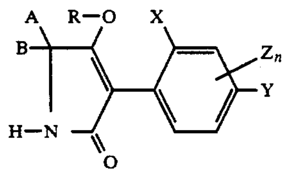

(I)

in which the variables are described in the specification.

10 Claims, No Drawings

INSECTICIDAL, ACARICIDAL AND HERBICIDAL 1-H-3-ARYL-PYRROLIDINE-2,4-DIONE DERIVATIVES

The invention relates to new 3-aryl-pyrrolidine-2,4-dione derivatives, to a plurality of processes for their preparation, and to their use as insecticides, acaricides and herbicides.

Pharmaceutical properties have previously been described for 3-acyl-pyrrolidine-2,4-diones (S. Suzuki et al. Chem. Pharm. Bull. 15, 1120 (1967)). Furthermore, N-phenyl-pyrrolidine-2,4-diones were synthesized by R. Schmierer and H. Mildenberger (Liebigs Ann. Chem. 1985 1095). However, a biological activity of these compounds was not described.

EP-A 0,262,399 discloses compounds of a similar structure (3-aryl-pyrrolidine-2,4-diones), but it has not emerged that they have herbicidal, insecticidal or acaricidal action.

DE-A 3,525,109 discloses 1-H-3-arylpyrrolidine-2,4-diones of a similar structure which are used as intermediates in the syntheses of dyes.

New 3-aryl-pyrrolidine-2,4-dione derivatives which are outlined by the formula (I)

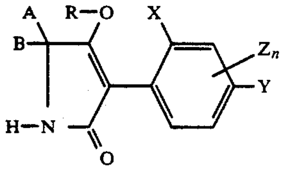

(I)

in which

X represents alkyl, halogen or alkoxy,

Y represents hydrogen, alkyl, halogen, alkoxy or halogenalkyl,

Z represents alkyl, halogen or alkoxy, n represents a number from 0–3,

R represents hydrogen, or represents the groups $-CO-R^1$, $-CO-O-R^2$ or $E^{\oplus}$ in which $R^1$ represents alkyl, alkenyl, alkoxyalkyl, alkylthioalkyl, polyalkoxyalkyl or cycloalkyl which can be interrupted by hetero atoms, each of these substituents being optionally substituted by halogen, or represents optionally substituted phenyl, optionally substituted phenylalkyl, substituted hetaryl, substituted phenoxyalkyl or substituted hetaryloxyalkyl and $R^2$ represents alkyl, alkenyl, alkoxyalkyl, polyalkoxyalkyl or optionally substituted phenyl, each of these substituents being optionally substituted by halogen, A represents hydrogen, or alkyl, alkenyl, alkynyl, alkoxyalkyl, alkylthioalkyl or cycloalkyl which is optionally interrupted by hetero atoms, each of these radicals being optionally substituted by halogen, or represents aryl, arylalkyl or hetaryl each of which is optionally substituted by halogen, alkyl, halogenoalkyl, alkoxy or nitro, B represents hydrogen, alkyl or alkoxyalkyl, or where A and B together with the carbon atom to which they are bonded form a carbocycle and $E^{\oplus}$ represents a metal ion equivalent or an ammonium ion, and the pure enantiomeric forms of compounds of the formula (I)

have now been found.

The following sub-groups may be defined below:

(Ia): compounds of the formula (I) where R = hydrogen, (Ib): compounds of the formula (I) where $R = COR^1$, (Ic): compounds of the formula (I) where $R = COOR^2$, (Id): compounds of the formula (I) where $R = E^{\oplus}$ represents a metal ion equivalent or an ammonium ion.

Furthermore, it has been found that 3-arylpyrrolidine-2,4-diones or their enols of the formula (Ia)

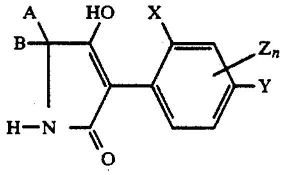

(Ia)

in which A, B, C, X, Y, Z and n have the abovementioned meanings, are obtained when (A) N-acylamino acid esters of the formula (II)

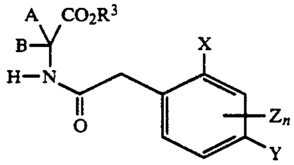

(II)

in which

A, B, X, Y, Z and n have the abovementioned meanings and $R^3$ represents alkyl, are subjected to intramolecular condensation in the presence of a diluent and in the presence of a base.

(B) Furthermore, it has been found that compounds of the formula (Ib)

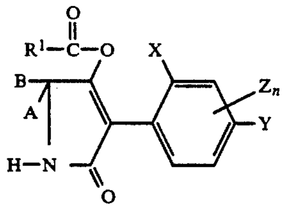

(Ib)

in which A, B, X, Y, Z, $R^1$ and n have the abovementioned meanings, are obtained when compounds of the formula (Ia)

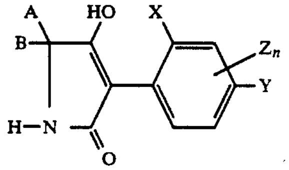

(Ia)

in which

A, B, X, Y, Z and n have the abovementioned meanings, are reacted

α) with acid halides of the general formula (III)

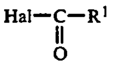

(III)

in which $R^1$ has the abovementioned meaning and

Hal represents halogen, in particular chlorine and bromine, if appropriate in the presence of a diluent and if appropriate in the presence of an acid-binding agent, or β) with carboxylic anhydrides of the general formula (IV)

$R^1—CO—O—CO—R^1$ (IV)

in which $R^1$ has the abovementioned meaning, if appropriate in the presence of a diluent and if appropriate in the presence of an acid-binding agent.

(C) Furthermore, it has been found that compounds of the formula (Ic)

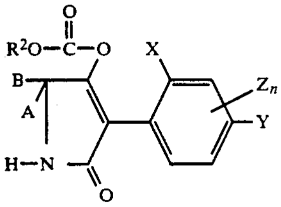

(Ic)

in which

A, B, C, X, Y, Z, $R^2$ and n have the abovementioned meanings, are obtained when compounds of the formula (Ia)

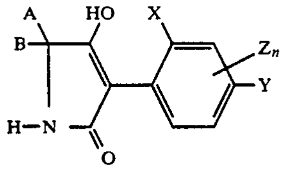

(Ia)

in which

A, B, X, Y, Z and n have the abovementioned meanings, are reacted with chloroformic esters of the general formula (V)

$R^2—O—CO—Cl$ (V)

in which $R^2$ has the abovementioned meaning, if appropriate in the presence of a diluent and if appropriate in the presence of an acid-binding agent.

D) Furthermore, it has been found that compounds of the formula (I)

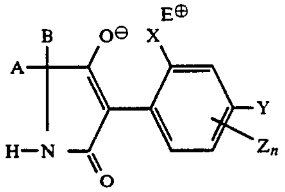

(Id)

in which X, Y, Z, A, B and n have the abovementioned meanings, are obtained when compounds of the formula (Ia)

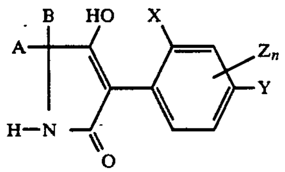

(Ia)

in which X, Y, Z, A, B and have the abovementioned meanings, are reacted with metal hydroxides or amines of the general formulae (VI) and (VII)

$Me_sOH_t$ (VI)

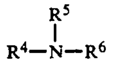

(VII)

in which

Me represents monovalent or divalent metal ions, s and t represent the numbers 1 and 2 and $R^4$, $R^5$ and $R^6$ independently of one another represent hydrogen and alkyl, if appropriate in the presence of a diluent.

Surprisingly, it has been found that the new 3-aryl-pyrrolidine-2,4-dione derivatives of the formula (I) are distinguished by outstanding insecticidal, acaricidal and herbicidal actions.

Preferred 3-aryl-pyrrolidine-2,4-dione derivatives of the formula (I) are those in which X represents $C_1$-$C_6$-alkyl, halogen or $C_1$-$C_6$-alkoxy, Y represent hydrogen, $C_1$-$C_6$-alkyl, halogen or $C_1$-$C_6$-alkoxy or $C_1$-$C_3$-halogenoalkyl, Z represents $C_1$-$C_6$-alkyl, halogen or $C_1$-$C_6$-alkoxy, n represents a number from 0–3, R represents hydrogen (Ia), or represents the groups of the formula $—CO—R^1$ or (Ib)

$—CO—O—R^2$ or (Ic)

$E^{\oplus}$ (Id)

in which $R^1$ represents $C_1$-$C_{20}$-alkyl, $C_2$-$C_{20}$-alkenyl, $C_1$-$C_8$-alkoxy-$C_2$-$C_8$-alkyl, $C_1$-$C_8$-alkylthio-$C_2$-$C_8$-alkyl, $C_1$-$C_8$-polyalkoxy-$C_2$-$C_8$-alkyl or cycloalkyl which has 3–8 ring atom sand which can be interrupted by oxygen and/or sulphur, each of these substituents being optionally substituted by halogen, or represents optionally halogen-, nitro-, $C_1$-$C_6$-alkyl-, $C_1$-$C_6$-alkoxy-, $C_1$-$C_6$-halogenalkyl- or $C_1$-$C_6$-halogenalkoxy-substituted phenyl; or represents optionally halogen-, $C_1$–$C_6$-alkyl, $C_1$–$C_6$-alkoxy-, $C_1$–$C_6$-halogenalkyl- or $C_1$–$C_6$-halogenalkoxy-substituted phenyl-$C_1$–$C_6$-alkyl, or represents optionally halogen- or $C_1$–$C_6$-alkyl-substituted hetaryl, or represents optionally halogen- or $C_1$–$C_6$-alkyl-substituted phenoxy-$C_1$–$C_6$-alkyl, or represents optionally halogen, amino or $C_1$–$C_6$-alkyl-substituted hetaryloxy-$C_1$–$C_6$-alkyl, $R^2$ represents $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl each of which is optionally substituted by halogen, or represents optionally halogen-, nitro-, $C_1$–$C_6$-alkyl-, $C_1$–$C_6$-alkoxy- or $C_1$–$C_6$-halogeno-alkyl-substituted phenyl, A represents hydrogen or represents straight-chain or branched $C_1$–$C_{12}$-alkyl, $C_3$–$C_8$-alkenyl, $C_3$–$C_8$-alkynyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$-alkylthio-$C_2$–$C_8$-alkyl, cycloalkyl which has 3–8 ring atoms and which can be interrupted by oxygen and/or sulphur, each of these substituents being optionally substituted by halogen, or represents aryl, hetaryl or aryl-$C_1$–$C_6$-alkyl each of which is optionally substituted by halogen, $C_1$–$C_6$-alkyl-$C_1$–$C_6$-haloalkyl, $C_1$–$C_6$-alkoxy or nitro, B represents hydrogen or straight-chain or branched $C_1$–$C_{12}$-alkyl or $C_1$–$C_8$-alkoxyalkyl, or where A and B together with the carbon atom to which they are bonded form a 3 to 8-membered ring, $E^{\oplus}$ represents a metal ion equivalent or an ammonium ion, and the pure enantiomeric forms of compounds of the formula (I).

Particularly preferred compounds of the formula (I) are those in which

X represents $C_1$–$C_4$-alkyl, halogen, or $C_1$–$C_4$-alkoxy,

Y represents hydrogen, $C_1$–$C_6$-alkyl, halogen, $C_1$–$C_4$-alkoxy or $C_1$–$C_2$-halogenoalkyl, Z represents $C_1$–$C_4$-alkyl, halogen or $C_1$–$C_4$-alkoxy, n represents a number from 0–3, R represents hydrogen (Ia) or represents the groups of the formula $-CO-R^1$ or (Ib)

$-CO-O-R^2$ or (Ic)

$E^{\oplus}$ (Id)

in which $R^1$ represents $C_1$–$C_{16}$-alkyl, $C_2$–$C_{16}$-alkenyl, $C_1$–$C_6$-alkoxy-$C_2$–$C_6$-alkyl, $C_1$–$C_6$-alkylthio-$C_2$–$C_6$-alkyl, $C_1$–$C_6$-polyalkoxy-$C_2$–$C_6$-alkyl or cycloalkyl which has 3–7 ring atoms and which can be interrupted by 1–2 oxygen and/or sulphur atoms, each of these substituents being optionally substituted by halogen, or represents optionally halogen-, nitro-, $C_1$–$C_4$-alkyl-, $C_1$–$C_4$-alkoxy-, $C_1$–$C_3$-halogenoalkyl-or $C_1$–$C_3$-halogenoalkoxy-substituted phenyl, or represents optionally halogen-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, or represents optionally halogen- or $C_1$–$C_6$-alkyl-substituted hetaryl, optionally represents halogen- or $C_1$–$C_4$-alkyl-substituted phenoxy-$C_1$–$C_5$-alkyl, or represents optionally halogen, amino or $C_1$–$C_4$-alkyl-substituted hetaryloxy-$C_1$–$C_5$-alkyl, $R^2$ represents $C_1$–$C_{16}$-alkyl, $C_2$–$C_{16}$-alkenyl, $C_1$–$C_{16}$-alkoxy-$C_2$–$C_6$-alkyl or $C_1$–$C_6$-polyalkoxy-$C_2$–$C_6$-alkyl each of which is optionally substituted by halogen, or represents optionally halogen, nitro-, $C_1$–$C_4$-alkyl, $C_1$–$C_3$-alkoxy- or $C_1$–$C_3$-halogeno-alkyl-substituted phenyl, A represents hydrogen or straight-chain or branched $C_1$–$C_{10}$-alkyl, $C_3$–$C_6$-alkenyl, $C_3$–$C_6$-alkynyl, $C_1$–$C_8$-alkoxy-$C_2$–$C_6$-alkyl, $C_1$–$C_6$-polyalkoxy-$C_2$–$C_6$-alkyl, $C_1$–$C_8$-alkylthio-$C_2$–$C_6$-alkyl, or cycloalkyl which has 3–7 ring atoms and which can be interrupted by 1–2 oxygen and/or sulphur atoms, each of these substituents being optionally substituted by halogen, or represents aryl, hetaryl or aryl-$C_1$–$C_4$-alkyl each of which is optionally substituted by halogen-, $C_1$–$C_4$-alkyl-, $C_1$–$C_4$-haloalkyl-$C_1$–$C_4$-alkoxy- or nitro, B represents hydrogen or straight-chain or branched $C_1$–$C_{10}$-alkyl or $C_1$–$C_6$-alkoxyalkyl, or where A and B together with the carbon atom to which they are bonded form a 3 to 7-membered ring, $E^{\oplus}$ represents a metal ions equivalent or an ammonium ion, and the pure enantiomeric forms of compounds of the formula (I).

Very particularly preferred compounds of the formula (I) are those in which

X represents methyl, ethyl, propyl, i-propyl, fluorine, chlorine, bromine, methoxy or ethoxy, Y represents hydrogen, methyl, ethyl, propyl, i-propyl, butyl, i-butyl, tert.-butyl, fluorine, chlorine, bromine, methoxy, ethoxy or trifluoromethyl, Z represents methyl, ethyl, i-propyl, butyl, i-butyl, tert.-butyl, fluorine, chlorine, bromine, methoxy or ethoxy, n represents a number from 0–3, R represents hydrogen (Ia) or represents the groups of the formula $-CO-R^1$ or (Ib)

$-CO-O-R^2$ or (Ic)

$E^{\oplus}$ (Id)

in which $R^1$ represents $C_1$–$C_{14}$-alkyl, $C_2$–$C_{14}$-alkenyl, $C_1$–$C_4$-alkoxy-$C_2$–$C_6$--alkyl, $C_1$–$C_4$-alkylthio-$C_2$–$C_6$-alkyl, $C_1$–$C_4$-polyalkoxy-$C_2$–$C_4$-alkyl and cycloalkyl which has 3–6 ring atoms and which can be interrupted by 1–2 oxygen and/or sulphur atoms, each of these substituents being optionally substituted by fluorine or chlorine, or represents optionally fluorine- chlorine-, bromine-, methyl-, ethyl-, propyl, i-propyl-, methoxy-, ethoxy-, trifluoromethyl-, trifluoromethoxy-or nitro-substituted phenyl, or represents optionally fluorine-, chlorine-, bromine-, methyl-, ethyl-, propyl-, i-propyl-, methoxy-, ethoxy-, trifluoromethyl- or trifluoromethoxy-substituted phenyl-$C_1$–$C_3$-alkyl, or represents pyridyl, pyrimidyl, thiazolyl or pyrazolyl each of which is optionally substituted by fluorine-, chlorine-, bromine-, methyl- or ethyl-, or represents optionally fluorine-, chlorine-, methyl- or ethyl-substituted phenoxy- $C_1$-$C_4$-alkyl, or represents pyridyloxy-$C_1$-$C_4$-alkyl, pyrimidyloxy-$C_1$-$C_4$-alkyl or thiazolyloxy-$C_1$-$C_4$-alkyl each of which is optionally substituted by fluorine-, chlorine-, amino-, methyl- or ethyl-, $R^2$ represents $C_1$-$C_{14}$-alkyl, $C_2$-$C_{14}$-alkenyl, $C_1$-$C_4$-alkoxy-$C_2$-$C_6$-alkyl or $C_1$-$C_4$-polyalkoxy-$C_2$-$C_6$-alkyl each of which is optionally substituted by fluorine or chlorine, or represents phenyl which is optionally substituted by fluorine, chlorine, nitro, methyl, ethyl, propyl, i-propyl, methoxy, ethoxy or trifluoromethyl, A represents hydrogen, or straight-chain or branched $C_1$-$C_8$-alkyl, $C_3$-$C_4$-alkenyl, $C_3$-$C_4$-alkynyl, $C_1$-$C_6$-alkoxy-$C_2$-$C_4$-alkyl, $C_1$-$C_4$-polyalkoxy-$C_2$-$C_4$-alkyl, $C_1$-$C_6$-alkylthio-$C_2$-$C_4$-alkyl, cycloalkyl which has 3-6 ring atoms and which can be interrupted by 1-2 oxygen and/or sulphur atoms, each of these substituents being optionally substituted by halogen, or represents aryl, pyridine, imidazole, pyrazole, triazole, indole, thiazole or aryl-$C_1$-$C_3$-alkyl each of which is optionally substituted by fluorine-, chlorine-, bromine-, methyl-, ethyl-, propyl-, iso-propyl-, methoxy-, ethoxy-, trifluoromethyl- or nitro, B represents hydrogen or straight-chain or branched $C_1$-$C_8$-alkyl or $C_1$-$C_4$-alkoxyalkyl, or where A and B together with the carbon atom to which they are bonded form a 3 to 6-membered ring, $E^{\oplus}$ represents a metal ion equivalent or an ammonium ion, and the pure enantiomeric forms of compounds of the formula (I).

If, according to process (A), N-2,6-dichlorophenylacetyl-alanine ethyl ester is used, the course of the process according to the invention can be outlined by the following equation:

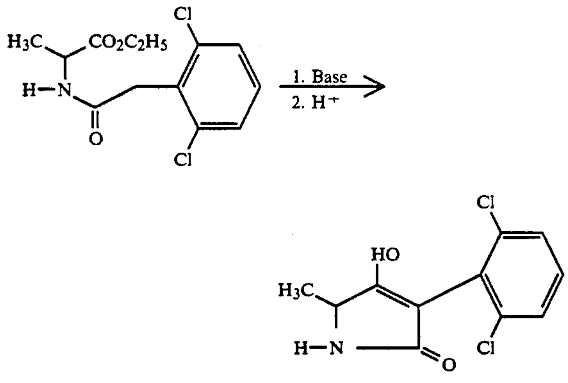

If, according to process (B) (variant α), 3-(2,5,6-trimethylphenyl)-5-isopropyl-pyrrolidine-2,4-dione and pivaloyl chloride are used as starting substances, the course of the process according to the invention can be outlined by the following equation:

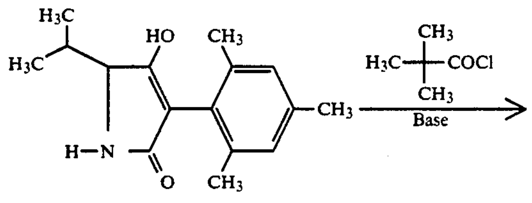

-continued

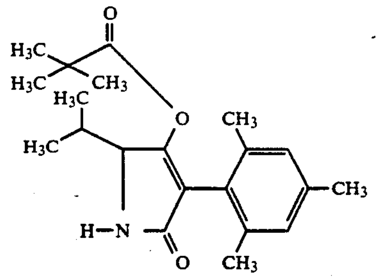

If, according to process B (variant β), 3-(2,4,6-timethylphenyl)-5-cyclopentyl-pyrrolidine-2,4-dione and acetic anhydride are used, the course of the process according to the invention can be outlined by the following equation:

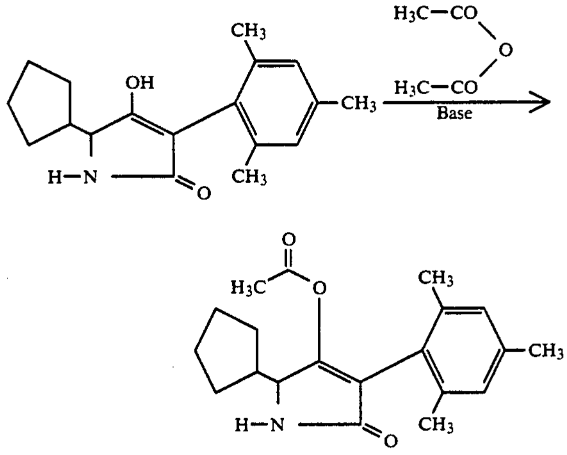

If, according to process C, 3-(2,4,6-trimethylphenyl)-5-phenyl-pyrrolidine-2,4-dione and ethoxyethyl chloroformate are used, the course of the process according to the invention can be outlined by the following equation:

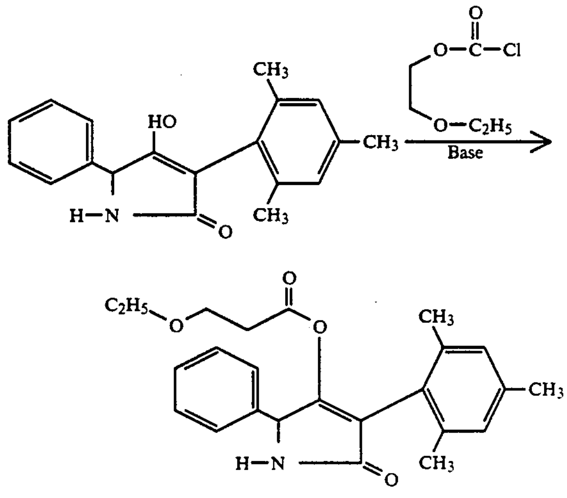

If, according to process D, 3-(2,4-dichlorophenyl)-5-(2-indolyl)-pyrrolidine-2,4-dione and methylamine are used, the course of the process according to the invention can be outlined by the following equation:

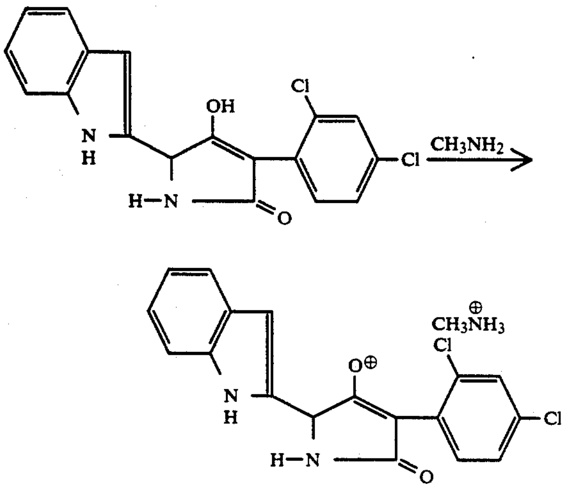

Some of the compounds of the formula (II)

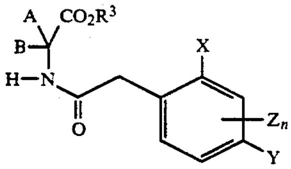
(II)

in which A, B, X, Y, Z, n and $R^3$ have the abovementioned meanings, and which are required as starting substances in the above process (A) are known or can be prepared in a simple manner by methods known in principle. For example, acyl-amino acid esters of the formula (II) are obtained when a) amino acid derivatives of the formula (VIII)

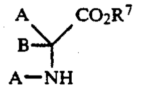
(VIII)

in which $R^7$ represents hydrogen (VIIIa) or alkyl (VIIIb) and

A has the abovementioned meanings, are acylated with phenylacetic halides of the formula (IX)

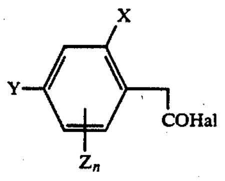
(IX)

in which

X, Y, Z and n have the abovementioned meanings and

Hal represents chlorine or bromine, (Chem. Reviews 52 237–416 (1953));

or when acylamino acids of the formula (IIa)

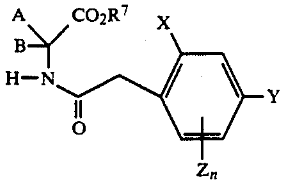
(IIa)

in which

A, B, X, Y, Z and n have the abovementioned meanings and $R^7$ represents hydrogen, are esterified (Chem. Ind. (London) 1568 (1968)).

The following compounds of the formula (II) may be mentioned by way of example:

1. N-2,4-dichlorophenyl-acetyl-glycine ethyl ester
2. N-2,6-dichlorophenyl-acetyl-glycine ethyl ester
3. N-(2,6-dichlorophenyl-acetyl)-alanine ethyl ester
4. N-(2,6-dichlorophenyl-acetyl)-valine ethyl ester
5. N-(2,6-dichlorophenyl-acetyl)-leucine ethyl ester
6. N-(2,6-dichlorophenyl-acetyl)-methionine ethyl ester
7. N-(2,6-dichlorophenyl-acetyl)-phenylanine ethyl ester
8. N-(2,6-dichlorophenyl-acetyl)-tryptophane ethyl ester
9. N-(2,6-dichlorophenyl-acetyl)-isoleucine ethyl ester
10. N-(2,4,6-trimethylphenyl-acetyl)-glycine methyl ester
11. N-(2,4,6-trimethylphenyl-acetyl)-alanine ethyl ester
12. N-(2,4,6-trimethylphenyl-acetyl)-valine ethyl ester
13. N-(2,4,6-trimethylphenyl-acetyl)-leucine ethyl ester
14. N-(2,4,6-trimethylphenyl-acetyl)-isoleucine ethyl ester
15. N-(2,4,6-trimethylphenyl-acetyl)-methionine ethyl ester
16. N-(2,4,6-trimethylphenyl-acetyl)-phenylalanine ethyl ester
17. N-(2,4,6-trimethylphenyl-acetyl)-tryptophane ethyl ester
18. N-(2,4,6-trimethylphenyl-acetyl)-(4-chlorophenyl)-alanine ethyl ester
19. N-(2,4,6-trimethylphenyl-acetyl)-S-methyl-cysteine ethyl ester
20. N-(2,4,6-trimethylphenyl-acetyl)-S-benzyl-cysteine ethyl ester
21. N-(2,4,6-trimethylphenyl-acetyl)-O-methyl-threonine ethyl ester
22. N-(2,4,6-trimethylphenyl-acetyl)-tert.-butyl-alanine ethyl ester
23. N-(2,4,6-trimethylphenyl-acetyl)-histidine ethyl ester
24. N-(2,4,6-trimethylphenyl-acetyl)-O-methyl- tyrosine ethyl ester
25. Methyl N-(2,4,6-trimethylphenyl-acetyl)-1-aminocyclopropane-carboxylate
26. Methyl N-(2,4,6-trimethylphenyl-acetyl)-1-aminocyclopentane-carboxylate
27. Methyl N-(2,4,6-trimethylphenyl-acetyl)-1-aminocyclohexane-carboxylate
28. Methyl N-(2,4,6-trimethylphenyl-acetyl)-1-amino-isobutyrate
29. Methyl N-(2,4,6-trimethylphenyl-acetyl)-2-ethyl-2-amino-butyrate
30. Methyl N-(2,4,6-trimethylphenyl-acetyl)-2-methyl-2-amino-butyrate 31. Methyl N-(2,4,6-trimethylphenyl-acetyl)-2-methyl-2-aminovalerate
32. Methyl N-(2,4,6-trimethylphenyl-acetyl)-2,3-dimethyl-2-aminovalerate The following compounds of the formula (IIa) may be mentioned by way of example:

1. N-2,4-dichlorophenyl-acetyl-glycine
2. N-2,6-dichlorophenyl-acetyl-glycine
3. N-(2,6-dichlorophenyl-acetyl)-alanine
4. N-(2,6-dichlorophenyl-acetyl)-valine
5. N-(2,6-dichlorophenyl-acetyl)-leucine
6. N-(2,6-dichlorophenyl-acetyl)-methionine
7. N-(2,6-dichlorophenyl-acetyl)-phenylalanine
8. N-(2,6-dichlorophenyl-acetyl)-tryptophane
9. N-(2,6-dichlorophenyl-acetyl)-isoleucine
10. N-(2,6-trimethylphenyl-acetyl)-glycine
11. N-(2,6-trimethylphenyl-acetyl)-alanine
12. N-(2,6-trimethylphenyl-acetyl)-valine
13. N-(2,6-trimethylphenyl-acetyl)-leucine
14. N-(2,6-trimethylphenyl-acetyl)-isoleucine
15. N-(2,6-trimethylphenyl-acetyl)-methionine
16. N-(2,6-trimethylphenyl-acetyl)-phenylalaine
17. N-(2,6-trimethylphenyl-acetyl)-tryptophane
18. N-(2,6-trimethylphenyl-acetyl)-(4-chlorophenyl)-alanine
19. N-(2,6-trimethylphenyl-acetyl)-S-methyl-cysteine
20. N-(2,6-trimethylphenyl-acetyl)-S-benzyl-cysteine
21. N-(2,6-trimethylphenyl-acetyl)-O-methyl-threonine
22. N-(2,6-trimethylphenyl-acetyl)-tert.-butyl-alanine
23. N-(2,6-trimethylphenyl-acetyl)-histidine
24. N-(2,6-trimethylphenyl-acetyl)-O-methyl -tyrosine
25. N-(2,6-trimethylphenyl-acetyl)-1-amino-cyclopropane-carboxylic acid
26. N-(2,6-trimethylphenyl-acetyl)-1-amino-cyclopentanecarboxylic acid
27. N-(2,6-trimethylphenyl-acetyl)-1-amino-cyclohexanecarboxylic acid
28. N-(2,6-trimethylphenyl-acetyl)-1-amino-isobutyric acid
29. N-(2,6-trimethylphenyl-acetyl)-2-ethyl-2-amino-butyric acid
30. N-(2,6-trimethylphenyl-acetyl)-2-methyl-2-aminobutyric acid
31. N-(2,6-trimethylphenyl-acetyl)-2-methyl-2-amino-valeric acid
32. N-(2,6-trimethylphenyl-acetyl)-2,3-dimethyl-2-amino-valeric acid Compounds of the formula (IIa) can be obtained, for example, from the phenylacetic halides of the formula (IX) and amino acids of the formula (VIIIa) by the method of Schotten-Baumann (Organikum [Practical Organic Chemistry], 9th edition, 446 (1970) VEB Deutscher Verlag der Wissenschaften, Berlin).

Compounds of the formula (VIIIa) and (VIIIb) are known or, alternatively, can be prepared with ease by processes known in principle from the literature.

Process (A) is characterized in that compounds of the formula (II) in which A, B, X, Y, Z, n and $R^3$ have the abovementioned meanings are subjected to an intramolecular condensation reaction in the presence of bases.

Diluents which can be used in process (A) according to the invention are all customary inert organic solvents. The following can preferably be used: hydrocarbons such as toluene and xylene, furthermore ethers such as dibutyl ether, tetrahydrofuran, dioxane, glycol dimethyl ether and diglycol dimethyl ether, and furthermore polar solvents such as dimethyl sulphoxide, sulpholane, dimethylformamide and N-methyl-pyrrolidone.

Deprotonating agents which can be employed for carrying out the process (A) according to the invention are all customary proton acceptors. The following can preferably be used: alkali metal oxides, alkali metal hydroxides, alkali metal carbonates, alkaline earth metal oxides, alkaline earth metal hydroxides and alkaline earth metal carbonates such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (methyl tri-$C_8$-$C_{10}$-alkyl-ammonium chloride) or TDA 1 (tris-(methoxyethoxyethyl)-amine). Other substances which can be employed are earth metal amides and alkaline earth metal hydrides such as sodium amide, sodium hydride and calcium hydride, and furthermore also alkali metal alcoholates such as sodium methylate, sodium ethylate and potassium tert.-butylate.

When carrying out process (A) according to the invention, the reaction temperatures can be varied within a substantial range. In general, the process is carried out at temperatures between 0° C. and 250° C., preferably between 50° C. and 150° C.

Process (A) according to the invention is generally carried under atmospheric pressure.

When carrying out process (A) according to the invention, the reactants of the formulae (II) and the deprotonating bases are generally employed in approximately equimolar amounts. However, it is also possible to use one or the other component in a larger excess (up to 3 moles).

Process (Bα) is characterized in that compounds of the formula (Ia) are reacted with carboxylic acid halides of the formula (III).

When the acid halides are used, then the diluents which can be employed in process (Bα) according to the invention are all inert solvents which are inert towards these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones as acetone and methyl isopropyl ketone, furthermore ethers such as diethyl ether, tetrahydrofuran and dioxane, in addition dimethyl sulphoxide and sulpholane. If the stability of the acid halide to hydrolysis permits, the reaction can also be carried out in the presence of water.

If the corresponding carboxylic acid halides are used, then acid-binding agents which are suitable for the reaction by process (Bα) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides such as magnesium oxide and calcium oxide, and in addition alkali metal carbonates and alkaline earth metal carbonates such as sodium carbonate, potassium carbonate and calcium carbonate.

When carrying out process (Bα) according to the invention, the reaction temperatures can also be varied within a substantial range when carboxylic acid halides are used. In general, the process is carried out at temperatures between −20° C. and +150° C., preferably between 0° C. and 100° C.

When carrying out the process (Bα) according to the invention, the starting substances of the formula (Ia) and the carboxylic acid halide of the formula (III) are generally used in approximately equivalent amounts. However, it is also possible to employ the carboxylic anhydride in a larger excess (up to 5 moles). Working-up is carried out by customary methods.

Process (Bβ) is characterized in that compounds of the formula (Ia) are reacted with carboxylic anhydrides of the formula (IV).

If, in process (Bβ) according to the invention, carboxylic anhydrides are used as reactant of the formula (IV), then the preferred diluents which can be used are those diluents which are also preferably suitable when halides are used. Apart from that, a carboxylic acid anhydride which is employed in excess can also act simultaneously as diluent.

The reaction temperatures in process (Bβ) according to the invention, too, can also be varied within a substantial range when carboxylic anhydrides are used. In general, the process is carried out at temperatures between −20° C. and +150° C., preferably between 0° C. and 100° C.

When carrying out the process according to the invention, the starting substances of the formula (Ia) and the carboxylic anhydride of the formula (IV) are generally used in approximately equivalent amounts. However, it is also possible to employ the carboxylic anhydride in a larger excess (up to 5 moles). Working-up is carried out by customary methods.

In general, a procedure is followed in which the diluent and carboxylic anhydride which is present in excess, as well as the carboxylic acid which is formed, are removed by distillation or by washing with an organic solvent or with water.

Process (C) is characterized in that compounds of the formula (Ia) are reacted with chloroformic esters of the formula (V).

If, in the reaction of process (C) according to the invention, the corresponding chloroformic esters are used, then the acid-binding agents which are suitable are all customary acid acceptors. The following can preferably be used: tertiary amines such as triethylamine, pyridine, DABCO, DBC, DBA, Hünig base and N,N-dimethylaniline, furthermore alkaline earth metal oxides such as magnesium oxide and calcium oxide, moreover alkali metal carbonates and alkaline earth metal carbonates such as sodium carbonate, potassium carbonate and calcium carbonate.

When the chloroformic esters are used, then suitable diluents are all solvents which are inert towards these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, in addition ketones such as acetone and methyl isopropyl ketone, furthermore ethers such as diethyl ether, tetrahydrofuran and dioxane, in addition carboxylic esters such as ethyl acetate and also strongly polar solvents such as dimethyl sulphoxide and sulpholane.

When the chloroformic esters are used as carboxylic acid derivatives of the formula (V), the reaction temperatures can be varied within a substantial range when carrying out process (C) according to the invention. If the process is carried out in the presence of a diluent and of an acid-binding agent, the reaction temperatures are generally between −20° C. and +100° C., preferably between 0° C. and 50° C.

Process (C) according to the invention is generally carried out under atmospheric pressure.

When carrying out process (C) according to the invention, the starting substances of the formula (Ia) and the corresponding chloroformic ester of the formula (V) are generally used in approximately equivalent amounts. However, it is also possible to employ one or the other component in a larger excess (up to 2 moles). Working-up is then carried out by customary methods. In general, a procedure is followed in which salts which have precipitated are removed and the reaction mixture which remains is concentrated by stripping off the diluent.

Process (D) is characterized in that compounds of the formula (Ia) are reacted with metal hydroxides (VI) or amines (VII).

Diluents which can be employed in the process according to the invention are preferably ethers such as tetrahydrofuran, dioxane or diethyl ether, or, alternatively, alcohols such as methanol, ethanol or isopropanol, and also water. In general, process (D) according to the invention is carried out under atmospheric pressure. In general, the reaction temperatures are between −20° C. and 100° C., preferably between 0° C. and 50° C.

When carrying out process (D) according to the invention, the starting substances of the formula (Ia) or (VI or (VII) are generally employed in approximately equimolar amounts. However, it is also possible to employ one or the other component in a larger excess (up to 2 moles). In general, a procedure is followed in which the reaction mixture is concentrated by stripping off the diluent.

PREPARATION EXAMPLES

Example 1

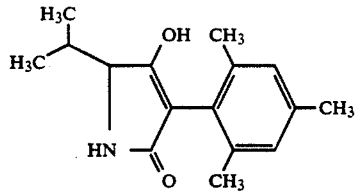

124.9 g (0.428 mol) of N-(2,4,6-trimethylphenylacetyl)-valine methyl ester are suspended in 430 ml of absolute toluene. 51.6 g of potassium tert.-butylate (95%) are added, and the mixture is then refluxed while TLC checks are carried out. The mixture is stirred into 500 ml of ice-water, the toluene is removed, and the aqueous phase is added dropwise at 0°-20° C. to 600 ml of 1N HCl. The precipitate is filtered off with suction, dried and recrystallized from chloroform/methyl tert.-butyl ether/n-hexane.

Yield: 51.5 g (=46.4% of theory) of the illustrated compound M.p. 126° C.

Example 2

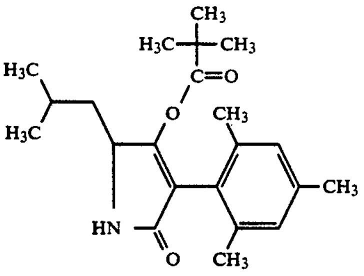

5.46 g (20 mmol) of 5-isobutyl-3-(2,4,6-trimethyl-phenyl)-pyrrolidine-2,4-dione are suspended in 70 ml of methyl tert.-butyl ether, and 3.4 ml (20 mmol) of Hünig base are added. 2.52 ml (20 mmol) of pivaloyl chloride in 5 ml of methyl tert.-butyl ether are added dropwise at 0°-10° C., and stirring is subsequently continued while carrying out thin-layer chromatography checks. The precipitate is filtered off with suction and rinsed, and the filtrate is evaporated on a rotary evaporator. Column chromatography on silica gel with cyclohexane/ethyl acetate 1:1 and crystallization from methyl tert.-butyl ether/n-hexane gave 2.14 g (29.9% of theory) of the illustrated compound of melting point 154° C.

Example 3

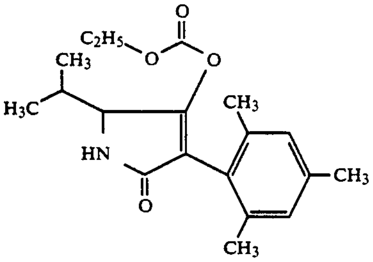

4.19 g (20 mmol) of 5-isopropyl-3-(2,4,6-trimethyl-phenyl)-pyrrolidine-2,4-dione are suspended in 70 ml of methyl tert.-butyl ether, and 3.4 ml (20 mmol) of Hünig based are added. 1.92 ml (20 mmol) of ethyl chloroformate in 5 ml of methyl tert.-butyl ether are added dropwise at −70° C., and the mixture is allowed to come to room temperature. It is evaporated on a rotary evaporator, and the residue is then taken up in methylene chloride, and the mixture is washed with water, dried and again evaporated on a rotary evaporator. Crystallization from methyl tert.-butyl ether/n-hexane gives 2.6 g (=39.3% of theory) of the illustrated compound of melting point 190° C.

The following compounds of Tables 1, 2 and 3 can be prepared similarly to Examples 1, 2 and 3, respectively:

TABLE 1

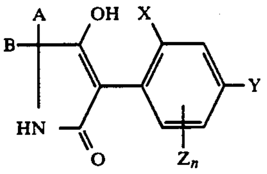

(Ia)

| Ex.-No. | X | Y | $Z_n$ | A | B | Mp °C. |
|---|---|---|---|---|---|---|
| 4 | Cl | Cl | H | H | H | |
| 5 | Cl | Cl | H | $CH_3$ | H | |
| 6 | Cl | Cl | H | $CH(CH_3)_2$ | H | |
| 7 | Cl | Cl | H | $CH_3$ | $CH_3$ | |
| 8 | Cl | Cl | H | $C_2H_5$ | $CH_3$ | |
| 9 | Cl | Cl | H | $C_2H_5$ | $C_2H_5$ | |
| 10 | Cl | Cl | H | $C_3H_7$ | $CH_3$ | |
| 11 | Cl | Cl | H | $i\text{-}C_3H_7$ | $CH_3$ | |
| 12 | Cl | Cl | H | $-(CH_2)_2-$ | | |
| 13 | Cl | Cl | H | $-(CH_2)_4-$ | | |
| 14 | Cl | Cl | H | $-(CH_2)_5-$ | | |
| 15 | Cl | Cl | H | $C_2H_5$ | H | |
| 16 | Cl | Cl | H | $C(CH_3)_3$ | H | |
| 17 | Cl | Cl | H | $CH_2CH(CH_3)_2$ | H | |
| 18 | Cl | Cl | H | 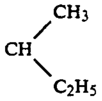 | H | |
| 19 | Cl | Cl | H | $CH_2-CH_2-S-CH_3$ | H | |
| 20 | Cl | Cl | H | $CH_2-S-CH_3$ | H | |
| 21 | Cl | Cl | H | $CH_2-S-CH_2-C_6H_5$ | H | |
| 22 | Cl | Cl | H | $CH_2-C_6H_5$ | | |
| 23 | Cl | Cl | H | 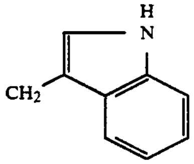 | H | |
| 24 | Cl | Cl | H | 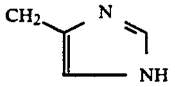 | H | |
| 25 | Cl | H | 6-Cl | H | H | |
| 26 | Cl | H | 6-Cl | $CH_3$ | H | |
| 27 | Cl | H | 6-Cl | $CH(CH_3)_2$ | H | |
| 28 | $CH_3$ | $CH_3$ | H | H | H | |
| 29 | $CH_3$ | $CH_3$ | H | $CH_3$ | H | |
| 30 | $CH_3$ | $CH_3$ | H | $CH(CH_3)_2$ | H | |
| 31 | $CH_3$ | $CH_3$ | 6-$CH_3$ | H | H | |
| 32 | $CH_3$ | $CH_3$ | 6-$CH_3$ | $CH_3$ | H | >230 |
| 33 | $CH_3$ | $CH_3$ | 6-$CH_3$ | $CH_3$ | $CH_3$ | 223 |
| 34 | $CH_3$ | $CH_3$ | 6-$CH_3$ | $C_2H_5$ | $CH_3$ | |
| 35 | $CH_3$ | $CH_3$ | 6-$CH_3$ | $C_2H_5$ | $C_2H_5$ | |
| 36 | $CH_3$ | $CH_3$ | 6-$CH_3$ | $C_3H_7$ | $CH_3$ | |
| 37 | $CH_3$ | $CH_3$ | 6-$CH_3$ | $i\text{-}C_3H_7$ | $CH_3$ | |
| 38 | $CH_3$ | $CH_3$ | 6-$CH_3$ | $-(CH_2)_2-$ | | 225 |
| 39 | $CH_3$ | $CH_3$ | 6-$CH_3$ | $-(CH_2)_4-$ | | |
| 40 | $CH_3$ | $CH_3$ | 6-$CH_3$ | $-(CH_2)_5-$ | | |
| 41 | $CH_3$ | $CH_3$ | 6-$CH_3$ | $C_2H_5$ | H | |
| 42 | $CH_3$ | $CH_3$ | 6-$CH_3$ | $C(CH_3)_3$ | H | |
| 43 | $CH_3$ | $CH_3$ | 6-$CH_3$ | $CH_2CH(CH_3)_2$ | H | >220 |
| 44 | $CH_3$ | $CH_3$ | 6-$CH_3$ | 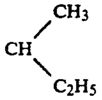 | H | |
| 45 | $CH_3$ | $CH_3$ | 6-$CH_3$ | $CH_2-CH_2-S-CH_3$ | H | |
| 46 | $CH_3$ | $CH_3$ | 6-$CH_3$ | $CH_2-S-CH_3$ | H | |
| 47 | $CH_3$ | $CH_3$ | 6-$CH_3$ | $CH_2-S-CH_2-C_6H_5$ | H | |
| 48 | $CH_3$ | $CH_3$ | 6-$CH_3$ | $CH_2-C_6H_5$ | | |

TABLE 1-continued

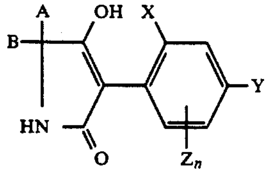

(Ia)

| Ex.-No. | X | Y | $Z_n$ | A | B | Mp °C. |
|---|---|---|---|---|---|---|
| 49 | $CH_3$ | $CH_3$ | 6-$CH_3$ | 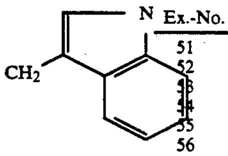 | H | |
| 50 | $CH_3$ | $CH_3$ | 6-$CH_3$ | 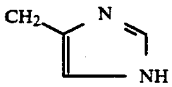 | H | |

TABLE 2

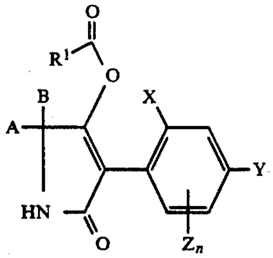

(Ib)

| Ex.-No. | X | Y | $Z_n$ | A | B | $R^1$ | Mp °C. |
|---|---|---|---|---|---|---|---|
| 51 | Cl | Cl | H | H | H | $CH_3$ | |
| 52 | Cl | Cl | H | $CH_3$ | H | $CH_3$ | |
| 53 | Cl | Cl | H | $CH_3$ | H | $C(CH_3)_3$ | |
| 54 | Cl | Cl | H | $CH_3$ | $CH_3$ | $CH_3$ | |
| 55 | Cl | Cl | H | $CH_3$ | $CH_3$ | $(CH_3)_2CH-$ | |
| 56 | Cl | Cl | H | $CH_3$ | $CH_3$ | $(CH_3)_3C-$ | |
| 57 | Cl | Cl | H | $CH_3$ | $CH_3$ | $CH_3-(CH_2)_3-$ | |
| 58 | Cl | Cl | H | $CH_3$ | $CH_3$ | $C_2H_5-C(CH_3)_2-$ | |
| 59 | Cl | Cl | H | $CH_3$ | $CH_3$ | $(CH_3)_3C-CH_2-$ | |
| 60 | Cl | Cl | H | $CH_3$ | $CH_3$ | $(CH_3)_2CH-C(CH_3)_2-$ | |
| 61 | Cl | Cl | H | $CH_3$ | $CH_3$ | $CH_2=CH-(CH_2)_8-$ | |
| 62 | Cl | Cl | H | $CH_3$ | $CH_3$ | 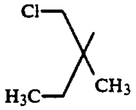 | |
| 63 | Cl | Cl | H | $CH_3$ | $CH_3$ | $C_4H_9-CH(-)-C_2H_5$ | |
| 64 | Cl | Cl | H | $CH_3$ | $CH_3$ | 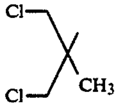 | |
| 65 | Cl | Cl | H | $CH_3$ | $CH_3$ | 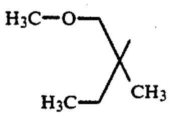 | |
| 66 | Cl | Cl | H | $CH_3$ | $CH_3$ | 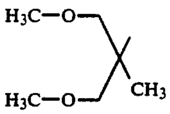 | |
| 67 | Cl | Cl | H | $CH_3$ | $CH_3$ | 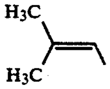 | |

TABLE 2-continued
(Ib)
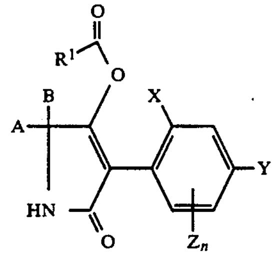
| Ex.-No. | X | Y | $Z_n$ | A | B | $R^1$ | Mp °C. |
|---|---|---|---|---|---|---|---|
| 68 | Cl | Cl | H | $CH_3$ | $CH_3$ | $H_3C—S—CH_2—$ | |
| 69 | Cl | Cl | H | $CH_3$ | $CH_3$ | 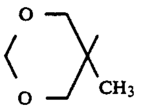 | |
| 70 | Cl | Cl | H | $CH_3$ | $CH_3$ | 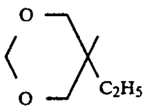 | |
| 71 | Cl | Cl | H | $CH_3$ | $CH_3$ | 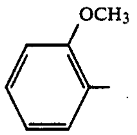 | |
| 72 | Cl | Cl | H | $CH_3$ | $CH_3$ | 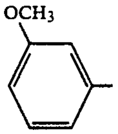 | |
| 73 | Cl | Cl | H | $CH_3$ | $CH_3$ | 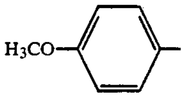 | |
| 74 | Cl | Cl | H | $CH_3$ | $CH_3$ | 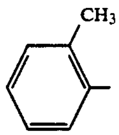 | |
| 75 | Cl | Cl | H | $CH_3$ | $CH_3$ | 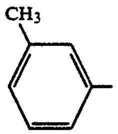 | |
| 76 | Cl | Cl | H | $CH_3$ | $CH_3$ | 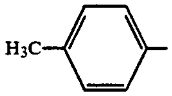 | |
| 77 | Cl | Cl | H | $CH_3$ | $CH_3$ | 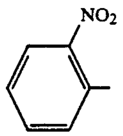 | |

TABLE 2-continued (Ib)

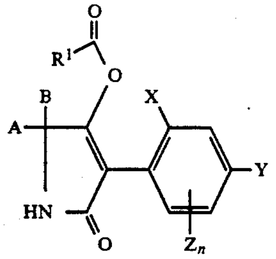

| Ex.-No. | X | Y | $Z_n$ | A | B | $R^1$ | Mp °C. |
|---|---|---|---|---|---|---|---|
| 78 | Cl | Cl | H | $CH_3$ | $CH_3$ | 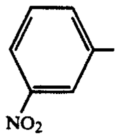 | |
| 79 | Cl | Cl | H | $CH_3$ | $CH_3$ | 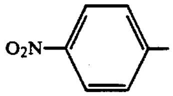 | |
| 80 | Cl | Cl | H | $CH_3$ | $CH_3$ | 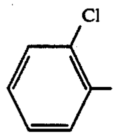 | |
| 81 | Cl | Cl | H | $CH_3$ | $CH_3$ | 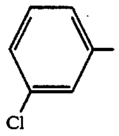 | |
| 82 | Cl | Cl | H | $CH_3$ | $CH_3$ | 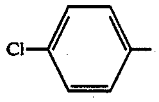 | |
| 83 | Cl | Cl | H | $CH_3$ | $CH_3$ | 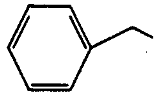 | |
| 84 | Cl | Cl | H | $C_2H_5$ | $CH_3$ | $CH_3$ | |
| 85 | Cl | Cl | H | $C_2H_5$ | $CH_3$ | $(CH_3)_2CH-$ | |
| 86 | Cl | Cl | H | $C_2H_5$ | $CH_3$ | $(CH_3)_3C-$ | |
| 87 | Cl | Cl | H | $C_2H_5$ | $CH_3$ | $CH_3-(CH_2)_3-$ | |
| 88 | Cl | Cl | H | $C_2H_5$ | $CH_3$ | $C_2H_5-C(CH_3)_2$ | |
| 89 | Cl | Cl | H | $C_2H_5$ | $CH_3$ | $(CH_3)_3C-CH_2-$ | |
| 90 | Cl | Cl | H | $C_2H_5$ | $CH_3$ | $(CH_3)_2CH-C(CH_3)_2$ | |
| 91 | Cl | Cl | H | $C_2H_5$ | $CH_3$ | $CH_2=CH-(CH_2)_8-$ | |
| 92 | Cl | Cl | H | $C_2H_5$ | $CH_3$ | 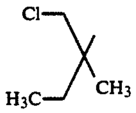 | |
| 93 | Cl | Cl | H | $C_2H_5$ | $CH_3$ | $C_4H_9-CH-C_2H_5$ | |

TABLE 2-continued
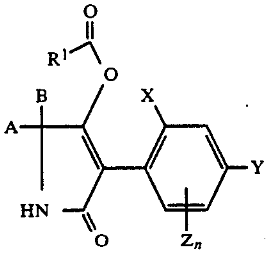
(Ib)
| Ex.-No. | X | Y | $Z_n$ | A | B | $R^1$ | Mp °C. |
|---|---|---|---|---|---|---|---|
| 94 | Cl | Cl | H | $C_2H_5$ | $CH_3$ | 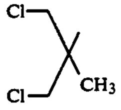 | |
| 95 | Cl | Cl | H | $C_2H_5$ | $CH_3$ | 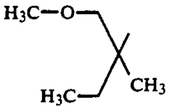 | |
| 96 | Cl | Cl | H | $C_2H_5$ | $CH_3$ | 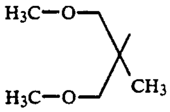 | |
| 97 | Cl | Cl | H | $C_2H_5$ | $CH_3$ | 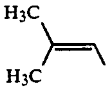 | |
| 98 | Cl | Cl | H | $C_2H_5$ | $CH_3$ | $H_3C-S-CH_2-$ | |
| 99 | Cl | Cl | H | $C_2H_5$ | $CH_3$ | 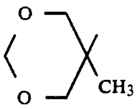 | |
| 100 | Cl | Cl | H | $C_2H_5$ | $CH_3$ | 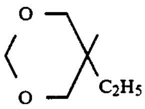 | |
| 101 | Cl | Cl | H | $C_2H_5$ | $CH_3$ | 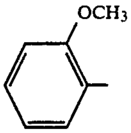 | |
| 102 | Cl | Cl | H | $C_2H_5$ | $CH_3$ | 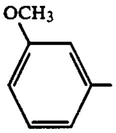 | |
| 103 | Cl | Cl | H | $C_2H_5$ | $CH_3$ | 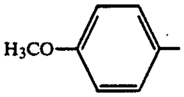 | |
| 104 | Cl | Cl | H | $C_2H_5$ | $CH_3$ | 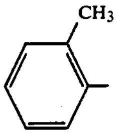 | |

TABLE 2-continued
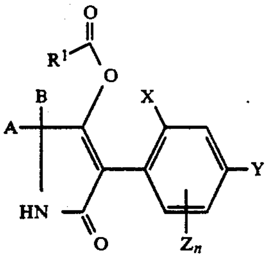
(Ib)
| Ex.-No. | X | Y | $Z_n$ | A | B | $R^1$ | Mp °C. |
|---|---|---|---|---|---|---|---|
| 105 | Cl | Cl | H | $C_2H_5$ | $CH_3$ | 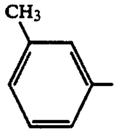 | |
| 106 | Cl | Cl | H | $C_2H_5$ | $CH_3$ | 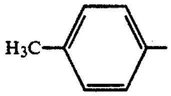 | |
| 107 | Cl | Cl | H | $C_2H_5$ | $CH_3$ | 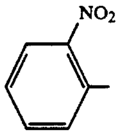 | |
| 108 | Cl | Cl | H | $C_2H_5$ | $CH_3$ | 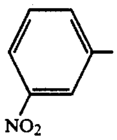 | |
| 109 | Cl | Cl | H | $C_2H_5$ | $CH_3$ | 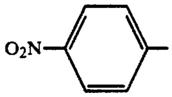 | |
| 110 | Cl | Cl | H | $C_2H_5$ | $CH_3$ | 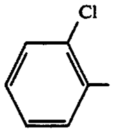 | |
| 111 | Cl | Cl | H | $C_2H_5$ | $CH_3$ | 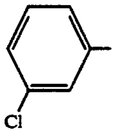 | |
| 112 | Cl | Cl | H | $C_2H_5$ | $CH_3$ | 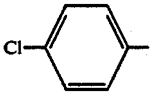 | |
| 113 | Cl | Cl | H | $C_2H_5$ | $CH_3$ | 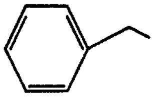 | |
| 114 | Cl | Cl | H | $C_2H_5$ | $C_2H_5$ | $CH_3$ | |
| 115 | Cl | Cl | H | $C_2H_5$ | $C_2H_5$ | $(CH_3)_2CH-$ | |
| 116 | Cl | Cl | H | $C_2H_5$ | $C_2H_5$ | $(CH_3)_3C-$ | |
| 117 | Cl | Cl | H | $C_2H_5$ | $C_2H_5$ | $CH_3-(CH_2)_3-$ | |

TABLE 2-continued
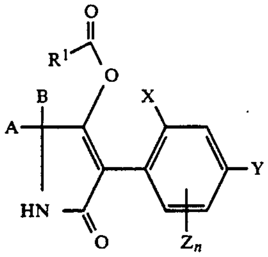
(Ib)
| Ex.-No. | X | Y | $Z_n$ | A | B | $R^1$ | Mp °C. |
|---|---|---|---|---|---|---|---|
| 118 | Cl | Cl | H | $C_2H_5$ | $C_2H_5$ | $C_2H_5-C(CH_3)_2-$ | |
| 119 | Cl | Cl | H | $C_2H_5$ | $C_2H_5$ | $(CH_3)_3C-CH_2-$ | |
| 120 | Cl | Cl | H | $C_2H_5$ | $C_2H_5$ | $(CH_3)_2CH-C(CH_3)_2-$ | |
| 121 | Cl | Cl | H | $C_2H_5$ | $C_2H_5$ | $CH_2=CH-(CH_2)_8-$ | |
| 122 | Cl | Cl | H | $C_2H_5$ | $C_2H_5$ | 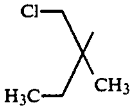 | |
| 123 | Cl | Cl | H | $C_2H_5$ | $C_2H_5$ | $C_4H_9-CH(-)-C_2H_5$ | |
| 124 | Cl | Cl | H | $C_2H_5$ | $C_2H_5$ | 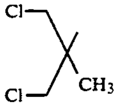 | |
| 125 | Cl | Cl | H | $C_2H_5$ | $C_2H_5$ | 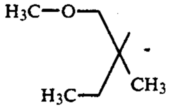 | |
| 126 | Cl | Cl | H | $C_2H_5$ | $C_2H_5$ | 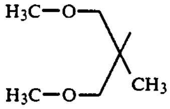 | |
| 127 | Cl | Cl | H | $C_2H_5$ | $C_2H_5$ | 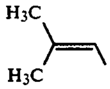 | |
| 128 | Cl | Cl | H | $C_2H_5$ | $C_2H_5$ | $H_3C-S-CH_2-$ | |
| 129 | Cl | Cl | H | $C_2H_5$ | $C_2H_5$ | 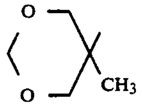 | |
| 130 | Cl | Cl | H | $C_2H_5$ | $C_2H_5$ | 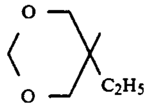 | |
| 131 | Cl | Cl | H | $C_2H_5$ | $C_2H_5$ | 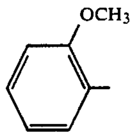 | |

TABLE 2-continued
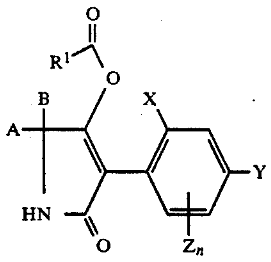
(Ib)
| Ex.-No. | X | Y | $Z_n$ | A | B | $R^1$ | Mp °C. |
|---|---|---|---|---|---|---|---|
| 132 | Cl | Cl | H | $C_2H_5$ | $C_2H_5$ | 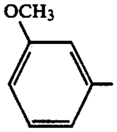 | |
| 133 | Cl | Cl | H | $C_2H_5$ | $C_2H_5$ | 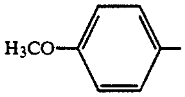 | |
| 134 | Cl | Cl | H | $C_2H_5$ | $C_2H_5$ | 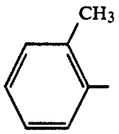 | |
| 135 | Cl | Cl | H | $C_2H_5$ | $C_2H_5$ | 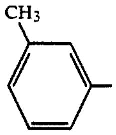 | |
| 136 | Cl | Cl | H | $C_2H_5$ | $C_2H_5$ | 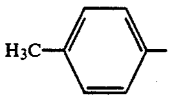 | |
| 137 | Cl | Cl | H | $C_2H_5$ | $C_2H_5$ | 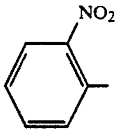 | |
| 138 | Cl | Cl | H | $C_2H_5$ | $C_2H_5$ | 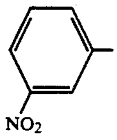 | |
| 139 | Cl | Cl | H | $C_2H_5$ | $C_2H_5$ | 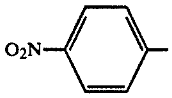 | |
| 140 | Cl | Cl | H | $C_2H_5$ | $C_2H_5$ | 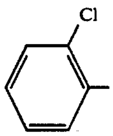 | |

TABLE 2-continued (Ib)

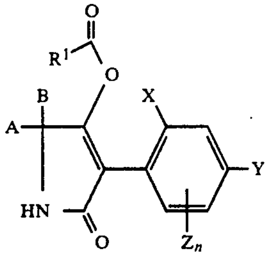

| Ex.-No. | X | Y | $Z_n$ | A | B | $R^1$ | Mp °C. |
|---|---|---|---|---|---|---|---|
| 141 | Cl | Cl | H | $C_2H_5$ | $C_2H_5$ | 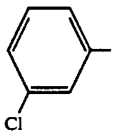 | |
| 142 | Cl | Cl | H | $C_2H_5$ | $C_2H_5$ | 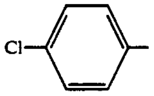 | |
| 143 | Cl | Cl | H | $C_2H_5$ | $C_2H_5$ | 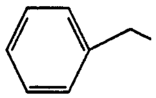 | |
| 144 | Cl | Cl | H | $C_3H_7$ | $CH_3$ | $CH_3$ | |
| 145 | Cl | Cl | H | $C_3H_7$ | $CH_3$ | $(CH_3)_2CH-$ | |
| 146 | Cl | Cl | H | $C_3H_7$ | $CH_3$ | $(CH_3)_3C-$ | |
| 147 | Cl | Cl | H | $C_3H_7$ | $CH_3$ | $CH_3-(CH_2)_3-$ | |
| 148 | Cl | Cl | H | $C_3H_7$ | $CH_3$ | $C_2H_5-C(CH_3)_2$ (with bond at C) | |
| 149 | Cl | Cl | H | $C_3H_7$ | $CH_3$ | $(CH_3)_3C-CH_2-$ | |
| 150 | Cl | Cl | H | $C_3H_7$ | $CH_3$ | $(CH_3)_2CH-C(CH_3)_2$ (with bond at C) | |
| 151 | Cl | Cl | H | $C_3H_7$ | $CH_3$ | $CH_2=CH-(CH_2)_8-$ | |
| 152 | Cl | Cl | H | $C_3H_7$ | $CH_3$ | 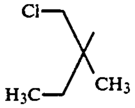 | |
| 153 | Cl | Cl | H | $C_3H_7$ | $CH_3$ | $C_4H_9-CH-C_2H_5$ (with bond at CH) | |
| 154 | Cl | Cl | H | $C_3H_7$ | $CH_3$ | 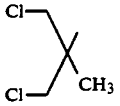 | |
| 155 | Cl | Cl | H | $C_3H_7$ | $CH_3$ | 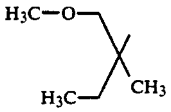 | |
| 156 | Cl | Cl | H | $C_3H_7$ | $CH_3$ | 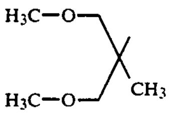 | |

TABLE 2-continued
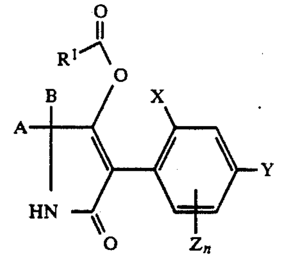
(Ib)
| Ex.-No. | X | Y | $Z_n$ | A | B | $R^1$ | Mp °C. |
|---|---|---|---|---|---|---|---|
| 157 | Cl | Cl | H | $C_3H_7$ | $CH_3$ | 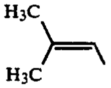 | |
| 158 | Cl | Cl | H | $C_3H_7$ | $CH_3$ | $H_3C—S—CH_2—$ | |
| 159 | Cl | Cl | H | $C_3H_7$ | $CH_3$ | 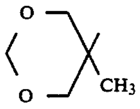 | |
| 160 | Cl | Cl | H | $C_3H_7$ | $CH_3$ | 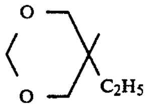 | |
| 161 | Cl | Cl | H | $C_3H_7$ | $CH_3$ | 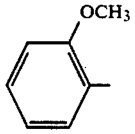 | |
| 162 | Cl | Cl | H | $C_3H_7$ | $CH_3$ | 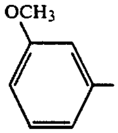 | |
| 163 | Cl | Cl | H | $C_3H_7$ | $CH_3$ | 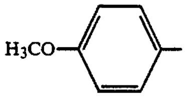 | |
| 164 | Cl | Cl | H | $C_3H_7$ | $CH_3$ | 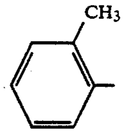 | |
| 165 | Cl | Cl | H | $C_3H_7$ | $CH_3$ | 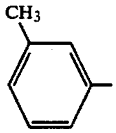 | |
| 166 | Cl | Cl | H | $C_3H_7$ | $CH_3$ | 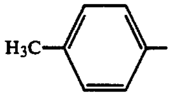 | |
| 167 | Cl | Cl | H | $C_3H_7$ | $CH_3$ | 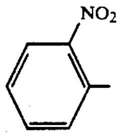 | |

TABLE 2-continued

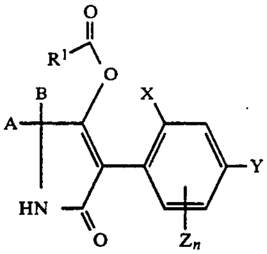
(Ib)

| Ex.-No. | X | Y | $Z_n$ | A | B | $R^1$ | Mp °C. |
|---|---|---|---|---|---|---|---|
| 168 | Cl | Cl | H | $C_3H_7$ | $CH_3$ | 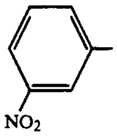 | |
| 169 | Cl | Cl | H | $C_3H_7$ | $CH_3$ | 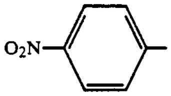 | |
| 170 | Cl | Cl | H | $C_3H_7$ | $CH_3$ | 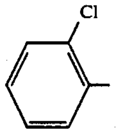 | |
| 171 | Cl | Cl | H | $C_3H_7$ | $CH_3$ | 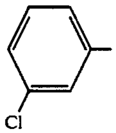 | |
| 172 | Cl | Cl | H | $C_3H_7$ | $CH_3$ | 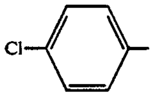 | |
| 173 | Cl | Cl | H | $C_3H_7$ | $CH_3$ | 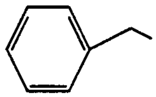 | |
| 174 | Cl | Cl | H | i-$C_3H_7$ | $CH_3$ | $CH_3$ | |
| 175 | Cl | Cl | H | i-$C_3H_7$ | $CH_3$ | $(CH_3)_2CH-$ | |
| 176 | Cl | Cl | H | i-$C_3H_7$ | $CH_3$ | $(CH_3)_3C-$ | |
| 177 | Cl | Cl | H | i-$C_3H_7$ | $CH_3$ | $CH_3-(CH_2)_3-$ | |
| 178 | Cl | Cl | H | i-$C_3H_7$ | $CH_3$ | $C_2H_5-C(CH_3)_2$ | |
| 179 | Cl | Cl | H | i-$C_3H_7$ | $CH_3$ | $(CH_3)_3C-CH_2-$ | |
| 180 | Cl | Cl | H | i-$C_3H_7$ | $CH_3$ | $(CH_3)_2CH-C(CH_3)_2$ | |
| 181 | Cl | Cl | H | i-$C_3H_7$ | $CH_3$ | $CH_2=CH-(CH_2)_8-$ | |
| 182 | Cl | Cl | H | i-$C_3H_7$ | $CH_3$ | 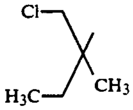 | |
| 183 | Cl | Cl | H | i-$C_3H_7$ | $CH_3$ | $C_4H_9-CH-C_2H_5$ | |

TABLE 2-continued
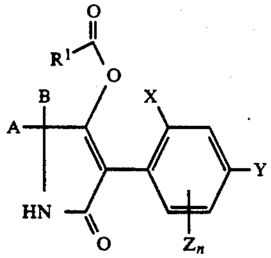
(Ib)
| Ex.-No. | X | Y | $Z_n$ | A | B | $R^1$ | Mp °C. |
|---|---|---|---|---|---|---|---|
| 184 | Cl | Cl | H | i-$C_3H_7$ | $CH_3$ | 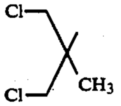 | |
| 185 | Cl | Cl | H | i-$C_3H_7$ | $CH_3$ | 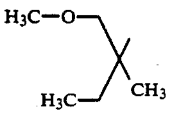 | |
| 186 | Cl | Cl | H | i-$C_3H_7$ | $CH_3$ | 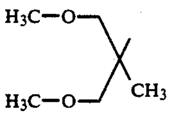 | |
| 187 | Cl | Cl | H | i-$C_3H_7$ | $CH_3$ | 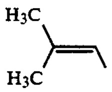 | |
| 188 | Cl | Cl | H | i-$C_3H_7$ | $CH_3$ | $H_3C-S-CH_2-$ | |
| 189 | Cl | Cl | H | i-$C_3H_7$ | $CH_3$ | 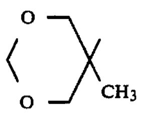 | |
| 190 | Cl | Cl | H | i-$C_3H_7$ | $CH_3$ | 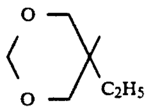 | |
| 191 | Cl | Cl | H | i-$C_3H_7$ | $CH_3$ | 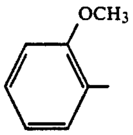 | |
| 192 | Cl | Cl | H | i-$C_3H_7$ | $CH_3$ | 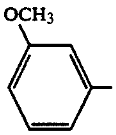 | |
| 193 | Cl | Cl | H | i-$C_3H_7$ | $CH_3$ | 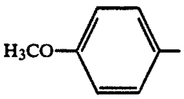 | |
| 194 | Cl | Cl | H | i-$C_3H_7$ | $CH_3$ | 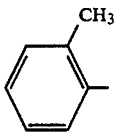 | |

TABLE 2-continued
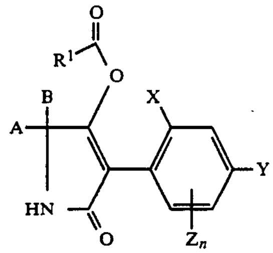
(Ib)
| Ex.-No. | X | Y | $Z_n$ | A | B | $R^1$ | Mp °C. |
|---|---|---|---|---|---|---|---|
| 195 | Cl | Cl | H | $i\text{-}C_3H_7$ | $CH_3$ | 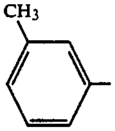 | |
| 196 | Cl | Cl | H | $i\text{-}C_3H_7$ | $CH_3$ | 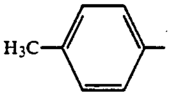 | |
| 197 | Cl | Cl | H | $i\text{-}C_3H_7$ | $CH_3$ | 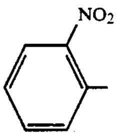 | |
| 198 | Cl | Cl | H | $i\text{-}C_3H_7$ | $CH_3$ | 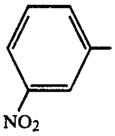 | |
| 199 | Cl | Cl | H | $i\text{-}C_3H_7$ | $CH_3$ | 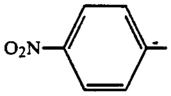 | |
| 200 | Cl | Cl | H | $i\text{-}C_3H_7$ | $CH_3$ | 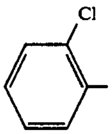 | |
| 201 | Cl | Cl | H | $i\text{-}C_3H_7$ | $CH_3$ | 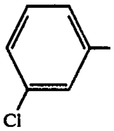 | |
| 202 | Cl | Cl | H | $i\text{-}C_3H_7$ | $CH_3$ | 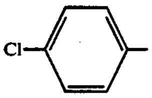 | |
| 203 | Cl | Cl | H | $i\text{-}C_3H_7$ | $CH_3$ | 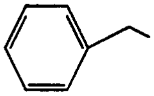 | |
| 204 | Cl | Cl | H | $-(CH_2)_4-$ | | $CH_3$ | |
| 205 | Cl | Cl | H | $-(CH_2)_4-$ | | $(CH_3)_2CH-$ | |
| 206 | Cl | Cl | H | $-(CH_2)_4-$ | | $(CH_3)_3C-$ | |
| 207 | Cl | Cl | H | $-(CH_2)_4-$ | | $CH_3-(CH_2)_3-$ | |

TABLE 2-continued
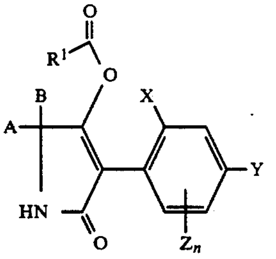
(Ib)
| Ex.-No. | X | Y | $Z_n$ | A | B | $R^1$ | Mp °C. |
|---|---|---|---|---|---|---|---|
| 208 | Cl | Cl | H | $-(CH_2)_4-$ | | $C_2H_5-C(CH_3)_2$ | |
| 209 | Cl | Cl | H | $-(CH_2)_4-$ | | $(CH_3)_3C-CH_2-$ | |
| 210 | Cl | Cl | H | $-(CH_2)_4-$ | | $(CH_3)_2CH-C(CH_3)_2$ | |
| 211 | Cl | Cl | H | $-(CH_2)_4-$ | | $CH_2=CH-(CH_2)_8-$ | |
| 212 | Cl | Cl | H | $-(CH_2)_4-$ | | 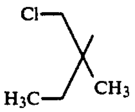 | |
| 213 | Cl | Cl | H | $-(CH_2)_4-$ | | $C_4H_9-CH-C_2H_5$ | |
| 214 | Cl | Cl | H | $-(CH_2)_4-$ | | 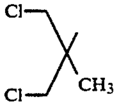 | |
| 215 | Cl | Cl | H | $-(CH_2)_4-$ | | 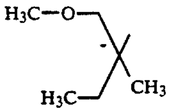 | |
| 216 | Cl | Cl | H | $-(CH_2)_4-$ | | 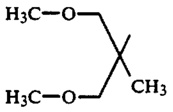 | |
| 217 | Cl | Cl | H | $-(CH_2)_4-$ | | 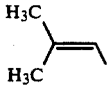 | |
| 218 | Cl | Cl | H | $-(CH_2)_4-$ | | $H_3C-S-CH_2-$ | |
| 219 | Cl | Cl | H | $-(CH_2)_4-$ | | 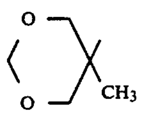 | |
| 220 | Cl | Cl | H | $-(CH_2)_4-$ | | 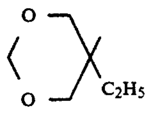 | |
| 221 | Cl | Cl | H | $-(CH_2)_4-$ | | 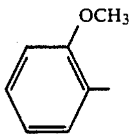 | |

TABLE 2-continued
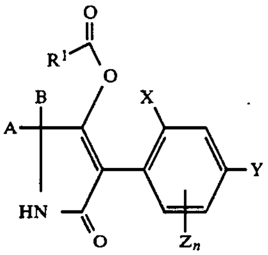
(Ib)
| Ex.-No. | X | Y | $Z_n$ | A | B | $R^1$ | Mp °C. |
|---|---|---|---|---|---|---|---|
| 222 | Cl | Cl | H | $-(CH_2)_4-$ | | 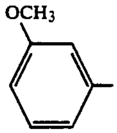 | |
| 223 | Cl | Cl | H | $-(CH_2)_4-$ | | 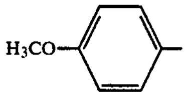 | |
| 224 | Cl | Cl | H | $-(CH_2)_4-$ | | 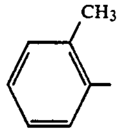 | |
| 225 | Cl | Cl | H | $-(CH_2)_4-$ | | 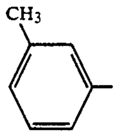 | |
| 226 | Cl | Cl | H | $-(CH_2)_4-$ | | 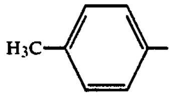 | |
| 227 | Cl | Cl | H | $-(CH_2)_4-$ | | 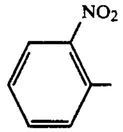 | |
| 228 | Cl | Cl | H | $-(CH_2)_4-$ | | 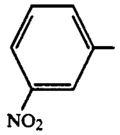 | |
| 229 | Cl | Cl | H | $-(CH_2)_4-$ | | 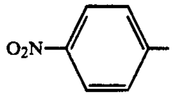 | |
| 230 | Cl | Cl | H | $-(CH_2)_4-$ | | 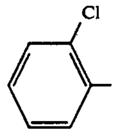 | |

TABLE 2-continued
(Ib)
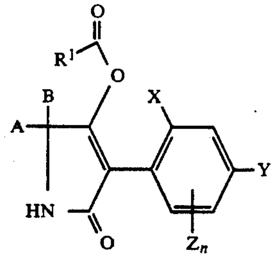
| Ex.-No. | X | Y | $Z_n$ | A | B | $R^1$ | Mp °C. |
|---|---|---|---|---|---|---|---|
| 231 | Cl | Cl | H | $-(CH_2)_4-$ | | 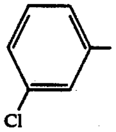 | |
| 232 | Cl | Cl | H | $-(CH_2)_4-$ | | 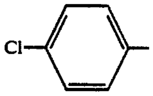 | |
| 233 | Cl | Cl | H | $-(CH_2)_4-$ | | 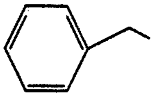 | |
| 234 | Cl | Cl | H | $-(CH_2)_5-$ | | $CH_3$ | |
| 235 | Cl | Cl | H | $-(CH_2)_5-$ | | $(CH_3)_2CH-$ | |
| 236 | Cl | Cl | H | $-(CH_2)_5-$ | | $(CH_3)_3C-$ | |
| 237 | Cl | Cl | H | $-(CH_2)_5-$ | | $CH_3-(CH_2)_3-$ | |
| 238 | Cl | Cl | H | $-(CH_2)_5-$ | | $C_2H_5-C(CH_3)_2$ | |
| 239 | Cl | Cl | H | $-(CH_2)_5-$ | | $(CH_3)_3C-CH_2-$ | |
| 240 | Cl | Cl | H | $-(CH_2)_5-$ | | $(CH_3)_2CH-C(CH_3)_2$ | |
| 241 | Cl | Cl | H | $-(CH_2)_5-$ | | $CH_2=CH-(CH_2)_8-$ | |
| 242 | Cl | Cl | H | $-(CH_2)_5-$ | | 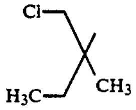 | |
| 243 | Cl | Cl | H | $-(CH_2)_5-$ | | $C_4H_9-CH-C_2H_5$ | |
| 244 | Cl | Cl | H | $-(CH_2)_5-$ | | 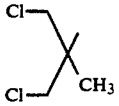 | |
| 245 | Cl | Cl | H | $-(CH_2)_5-$ | | 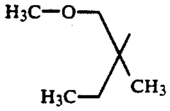 | |
| 246 | Cl | Cl | H | $-(CH_2)_5-$ | | 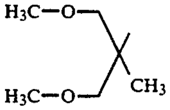 | |

TABLE 2-continued
(Ib)
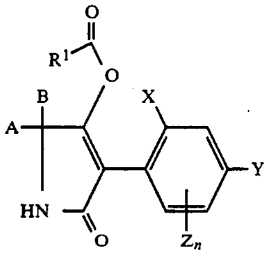
| Ex.-No. | X | Y | $Z_n$ | A | B | $R^1$ | Mp °C. |
|---|---|---|---|---|---|---|---|
| 247 | Cl | Cl | H | $-(CH_2)_5-$ | | 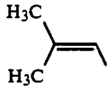 | |
| 248 | Cl | Cl | H | $-(CH_2)_5-$ | | $H_3C-S-CH_2-$ | |
| 249 | Cl | Cl | H | $-(C_2H_2)_5$ | | 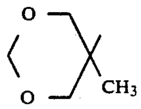 | |
| 250 | Cl | Cl | H | $-(CH_2)_5-$ | | 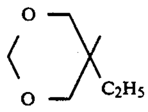 | |
| 251 | Cl | Cl | H | $-(CH_2)_5-$ | | 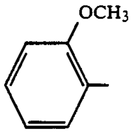 | |
| 252 | Cl | Cl | H | $-(CH_2)_5-$ | | 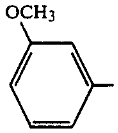 | |
| 253 | Cl | Cl | H | $-(CH_2)_5-$ | | 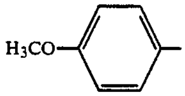 | |
| 254 | Cl | Cl | H | $-(CH_2)_5-$ | | 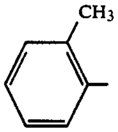 | |
| 255 | Cl | Cl | H | $-(CH_2)_5-$ | | 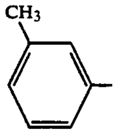 | |
| 256 | Cl | Cl | H | $-(CH_2)_5-$ | | 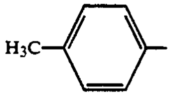 | |
| 257 | Cl | Cl | H | $-(CH_2)_5-$ | | 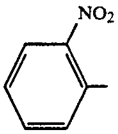 | |

TABLE 2-continued

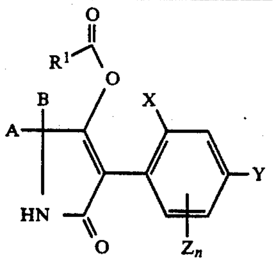

(Ib)

| Ex.-No. | X | Y | $Z_n$ | A | B | $R^1$ | Mp °C. |
|---|---|---|---|---|---|---|---|
| 258 | Cl | Cl | H | $-(CH_2)_5-$ | | 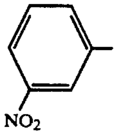 | |
| 259 | Cl | Cl | H | $-(CH_2)_5-$ | | 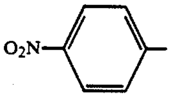 | |
| 260 | Cl | Cl | H | $-(CH_2)_5-$ | | 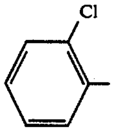 | |
| 261 | Cl | Cl | H | $-(CH_2)_5-$ | | 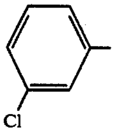 | |
| 262 | Cl | Cl | H | $-(CH_2)_5-$ | | 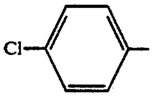 | |
| 263 | Cl | Cl | H | $-(CH_2)_5-$ | | 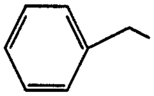 | |
| 264 | Cl | H | 6-Cl | H | H | $CH_3$ | |
| 265 | Cl | H | 6-Cl | H | H | $C(CH_3)_3$ | |
| 266 | Cl | H | 6-Cl | $CH_3$ | H | $CH_3$ | |
| 267 | Cl | H | 6-Cl | $CH_3$ | H | $C(CH_3)_3$ | |
| 268 | $CH_3$ | $CH_3$ | H | H | H | $CH_3$ | |
| 269 | $CH_3$ | $CH_3$ | H | H | H | $C(CH_3)_3$ | |
| 270 | $CH_3$ | $CH_3$ | H | $CH_3$ | H | $CH_3$ | |
| 271 | $CH_3$ | $CH_3$ | H | $CH_3$ | H | $C(CH_3)_3$ | |
| 272 | $CH_3$ | $CH_3$ | 6-$CH_3$ | H | H | $CH_3$ | |
| 273 | $CH_3$ | $CH_3$ | 6-$CH_3$ | H | H | $CH(CH_3)_2$ | |
| 274 | $CH_3$ | $CH_3$ | 6-$CH_3$ | H | H | $C(CH_3)_3$ | |
| 275 | $CH_3$ | $CH_3$ | 6-$CH_3$ | H | H | $C(CH_3)_2CH_2Cl$ | |
| 276 | $CH_3$ | $CH_3$ | 6-$CH_3$ | H | H | $C(CH_3)_2CH_2-O-CH_3$ | |
| 277 | $CH_3$ | $CH_3$ | 6-$CH_3$ | H | H | $CH_2-S-CH_3$ | |
| 278 | $CH_3$ | $CH_3$ | 6-$CH_3$ | H | H | 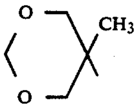 | |
| 279 | $CH_3$ | $CH_3$ | 6-$CH_3$ | H | H | 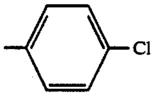 | |

TABLE 2-continued

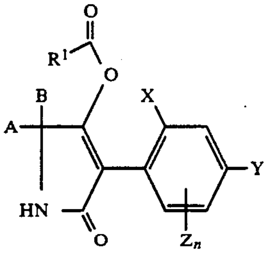

(Ib)

| Ex.-No. | X | Y | $Z_n$ | A | B | $R^1$ | Mp °C. |
|---|---|---|---|---|---|---|---|
| 280 | $CH_3$ | $CH_3$ | 6-$CH_3$ | H | H | 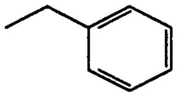 | |
| 281 | $CH_3$ | $CH_3$ | 6-$CH_3$ | $CH_3$ | H | $CH_3$ | 132 |
| 282 | $CH_3$ | $CH_3$ | 6-$CH_3$ | $CH_3$ | H | $CH(CH_3)_2$ | |
| 283 | $CH_3$ | $CH_3$ | 6-$CH_3$ | $CH_3$ | H | $C(CH_3)_3$ | 152 |
| 284 | $CH_3$ | $CH_3$ | 6-$CH_3$ | $CH_3$ | H | $C(CH_3)_2CH_2Cl$ | |
| 285 | $CH_3$ | $CH_3$ | 6-$CH_3$ | $CH_3$ | H | $C(CH_3)_2CH_2-O-CH_3$ | |
| 286 | $CH_3$ | $CH_3$ | 6-$CH_3$ | $CH_3$ | H | $CH_2-S-CH_3$ | |
| 287 | $CH_3$ | $CH_3$ | 6-$CH_3$ | $CH_3$ | H | 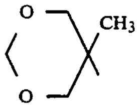 | |
| 288 | $CH_3$ | $CH_3$ | 6-$CH_3$ | $CH_3$ | H | 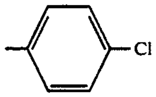 | |
| 289 | $CH_3$ | $CH_3$ | 6-$CH_3$ | $CH_3$ | H | 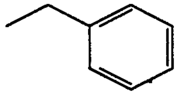 | |
| 290 | $CH_3$ | $CH_3$ | 6-$CH_3$ | $CH(CH_3)_2$ | H | $CH_3$ | 188 |
| 291 | $CH_3$ | $CH_3$ | 6-$CH_3$ | $CH(CH_3)_2$ | H | $CH(CH_3)_2$ | |
| 292 | $CH_3$ | $CH_3$ | 6-$CH_3$ | $CH(CH_3)_2$ | H | $C(CH_3)_3$ | 213 |
| 293 | $CH_3$ | $CH_3$ | 6-$CH_3$ | $CH(CH_3)_2$ | H | $C(CH_3)_2CH_2Cl$ | |
| 294 | $CH_3$ | $CH_3$ | 6-$CH_3$ | $CH(CH_3)_2$ | H | $C(CH_3)_2CH_2-O-CH_3$ | |
| 295 | $CH_3$ | $CH_3$ | 6-$CH_3$ | $CH(CH_3)_2$ | H | $CH_2-S-CH_3$ | |
| 296 | $CH_3$ | $CH_3$ | 6-$CH_3$ | $CH(CH_3)_2$ | H | 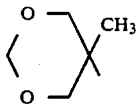 | |
| 297 | $CH_3$ | $CH_3$ | 6-$CH_3$ | $CH(CH_3)_2$ | H | 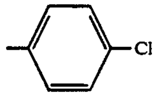 | |
| 298 | $CH_3$ | $CH_3$ | 6-$CH_3$ | $CH(CH_3)_2$ | H | 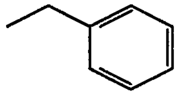 | |
| 299 | $CH_3$ | $CH_3$ | 6-$CH_3$ | $CH_2CH(CH_3)_2$ | H | $CH_3$ | 169 |
| 300 | $CH_3$ | $CH_3$ | 6-$CH_3$ | $CH_2CH(CH_3)_2$ | H | $C_2H_5$ | |
| 301 | $CH_3$ | $CH_3$ | 6-$CH_3$ | $CH_2CH(CH_3)_2$ | H | $CH(CH_3)_2$ | |
| 302 | $CH_3$ | $CH_3$ | 6-$CH_3$ | $CH_2CH(CH_3)_2$ | H | $C(CH_3)_2CH_2Cl$ | |
| 303 | $CH_3$ | $CH_3$ | 6-$CH_3$ | $CH_2CH(CH_3)_2$ | H | $C(CH_3)_2CH_2-O-CH_3$ | |
| 304 | $CH_3$ | $CH_3$ | 6-$CH_3$ | $CH_2CH(CH_3)_2$ | H | $CH_2-S-CH_3$ | |

TABLE 2-continued

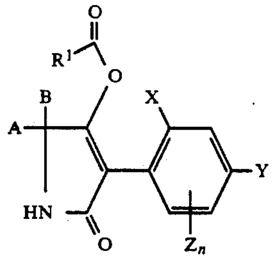

(Ib)

| Ex.-No. | X | Y | $Z_n$ | A | B | $R^1$ | Mp °C. |
|---|---|---|---|---|---|---|---|
| 305 | $CH_3$ | $CH_3$ | 6-$CH_3$ | $CH_2CH(CH_3)_2$ | H | 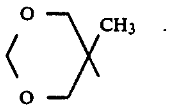 | |
| 306 | $CH_3$ | $CH_3$ | 6-$CH_3$ | $CH_2CH(CH_3)_2$ | H | 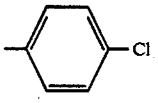 | |
| 307 | $CH_3$ | $CH_3$ | 6-$CH_3$ | $CH_2CH(CH_3)_2$ | H | 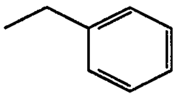 | |
| 308 | $CH_3$ | $CH_3$ | 6-$CH_3$ | $CH_3$<br>CH<br>$C_2H_5$ | H | $CH_3$ | 184 |
| 309 | $CH_3$ | $CH_3$ | 6-$CH_3$ | $CH_3$<br>CH<br>$C_2H_5$ | H | $CH(CH_3)_2$ | |
| 310 | $CH_3$ | $CH_3$ | 6-$CH_3$ | $CH_3$<br>CH<br>$C_2H_5$ | H | $C(CH_3)_3$ | |
| 311 | $CH_3$ | $CH_3$ | 6-$CH_3$ | $CH_3$<br>CH<br>$C_2H_5$ | H | $C(CH_3)_2CH_2Cl$ | |
| 312 | $CH_3$ | $CH_3$ | 6-$CH_3$ | $CH_3$<br>CH<br>$C_2H_5$ | H | $C(CH_3)_2CH_2-O-CH_3$ | |
| 313 | $CH_3$ | $CH_3$ | 6-$CH_3$ | $CH_3$<br>CH<br>$C_2H_5$ | H | $CH_2-S-CH_3$ | |
| 314 | $CH_3$ | $CH_3$ | 6-$CH_3$ | $CH_3$<br>CH<br>$C_2H_5$ | H | 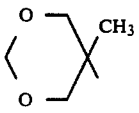 | |
| 315 | $CH_3$ | $CH_3$ | 6-$CH_3$ | $CH_3$<br>CH<br>$C_2H_5$ | H | 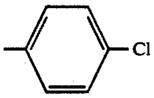 | |

TABLE 2-continued

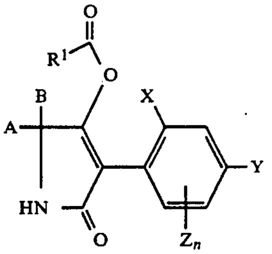

(Ib)

| Ex.-No. | X | Y | $Z_n$ | A | B | $R^1$ | Mp °C. |
|---|---|---|---|---|---|---|---|
| 316 | $CH_3$ | $CH_3$ | 6-$CH_3$ | 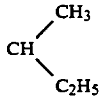 | H | 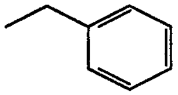 | |
| 317 | $CH_3$ | $CH_3$ | 6-$CH_3$ | $-(CH_2)_2SCH_3$ | H | $CH_3$ | |
| 318 | $CH_3$ | $CH_3$ | 6-$CH_3$ | $-(CH_2)_2SCH_3$ | H | $CH(CH_3)_2$ | |
| 319 | $CH_3$ | $CH_3$ | 6-$CH_3$ | $-(CH_2)_2SCH_3$ | H | $C(CH_3)_2$ | |
| 320 | $CH_3$ | $CH_3$ | 6-$CH_3$ | $-(CH_2)_2SCH_3$ | H | $C(CH_3)_2CH_2Cl$ | |
| 321 | $CH_3$ | $CH_3$ | 6-$CH_3$ | $-(CH_2)_2SCH_3$ | H | $C(CH_3)_2CH_2-O-CH_3$ | |
| 322 | $CH_3$ | $CH_3$ | 6-$CH_3$ | $-(CH_2)_2SCH_3$ | H | $CH_2-S-CH_3$ | |
| 323 | $CH_3$ | $CH_3$ | 6-$CH_3$ | $-(CH_2)_2SCH_3$ | H | 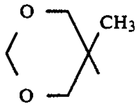 | |
| 324 | $CH_3$ | $CH_3$ | 6-$CH_3$ | $-(CH_2)_2SCH_3$ | H | 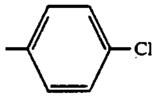 | |
| 325 | $CH_3$ | $CH_3$ | 6-$CH_3$ | $-(CH_2)_2SCH_3$ | H | 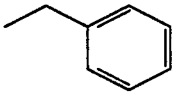 | |
| 326 | $CH_3$ | $CH_3$ | 6-$CH_3$ | $-(CH_2)_2-$ | | $CH_3$ | 94 |
| 327 | $CH_3$ | $CH_3$ | 6-$CH_3$ | $-(CH_2)_2-$ | | $-C(CH_3)_3$ | 95 |
| 328 | $CH_3$ | $CH_3$ | 6-$CH_3$ | $CH_3$ | $CH_3$ | $CH_3$ | 216 |
| 329 | $CH_3$ | $CH_3$ | 6-$CH_3$ | $CH_3$ | $CH_3$ | $(CH_3)_2CH-$ | |
| 330 | $CH_3$ | $CH_3$ | 6-$CH_3$ | $CH_3$ | $CH_3$ | $(CH_3)_3C-$ | >230 |
| 331 | $CH_3$ | $CH_3$ | 6-$CH_3$ | $CH_3$ | $CH_3$ | $CH_3-(CH_2)_3-$ | |
| 332 | $CH_3$ | $CH_3$ | 6-$CH_3$ | $CH_3$ | $CH_3$ | $C_2H_5-C(CH_3)_2$ | 183 |
| 333 | $CH_3$ | $CH_3$ | 6-$CH_3$ | $CH_3$ | $CH_3$ | $(CH_3)_3C-CH_2-$ | 175 |
| 334 | $CH_3$ | $CH_3$ | 6-$CH_3$ | $CH_3$ | $CH_3$ | $(CH_3)_2CH-C(CH_3)_2$ | |
| 335 | $CH_3$ | $CH_3$ | 6-$CH_3$ | $CH_3$ | $CH_3$ | $CH_2=CH-(CH_2)_8-$ | |
| 336 | $CH_3$ | $CH_3$ | 6-$CH_3$ | $CH_3$ | $CH_3$ | 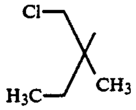 | |
| 337 | $CH_3$ | $CH_3$ | 6-$CH_3$ | $CH_3$ | $CH_3$ | $C_4H_9-CH-C_2H_5$ | |
| 338 | $CH_3$ | $CH_3$ | 6-$CH_3$ | $CH_3$ | $CH_3$ | 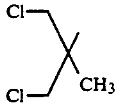 | |

TABLE 2-continued
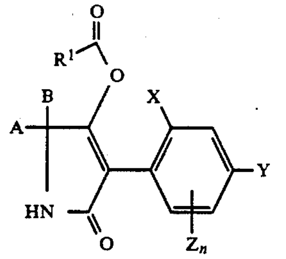
(Ib)
| Ex.-No. | X | Y | $Z_n$ | A | B | $R^1$ | Mp °C. |
|---|---|---|---|---|---|---|---|
| 339 | $CH_3$ | $CH_3$ | 6-$CH_3$ | $CH_3$ | $CH_3$ | 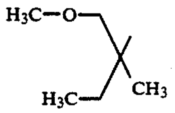 | |
| 340 | $CH_3$ | $CH_3$ | 6-$CH_3$ | $CH_3$ | $CH_3$ | 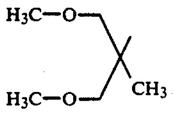 | |
| 341 | $CH_3$ | $CH_3$ | 6-$CH_3$ | $CH_3$ | $CH_3$ | 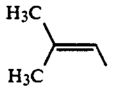 | |
| 342 | $CH_3$ | $CH_3$ | 6-$CH_3$ | $CH_3$ | $CH_3$ | $H_3C-S-CH_2-$ | |
| 343 | $CH_3$ | $CH_3$ | 6-$CH_3$ | $CH_3$ | $CH_3$ | 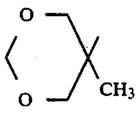 | |
| 344 | $CH_3$ | $CH_3$ | 6-$CH_3$ | $CH_3$ | $CH_3$ | 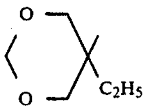 | |
| 345 | $CH_3$ | $CH_3$ | 6-$CH_3$ | $CH_3$ | $CH_3$ | 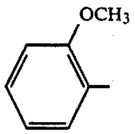 | |
| 346 | $CH_3$ | $CH_3$ | 6-$CH_3$ | $CH_3$ | $CH_3$ | 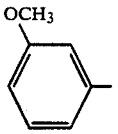 | |
| 347 | $CH_3$ | $CH_3$ | 6-$CH_3$ | $CH_3$ | $CH_3$ | 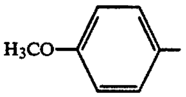 | |
| 348 | $CH_3$ | $CH_3$ | 6-$CH_3$ | $CH_3$ | $CH_3$ | 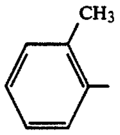 | |
| 349 | $CH_3$ | $CH_3$ | 6-$CH_3$ | $CH_3$ | $CH_3$ | 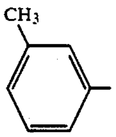 | |

TABLE 2-continued

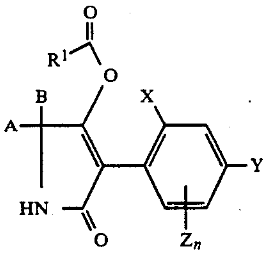

(Ib)

| Ex.-No. | X | Y | $Z_n$ | A | B | $R^1$ | Mp °C. |
|---|---|---|---|---|---|---|---|
| 350 | $CH_3$ | $CH_3$ | 6-$CH_3$ | $CH_3$ | $CH_3$ | 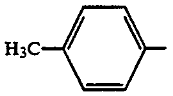 | |
| 351 | $CH_3$ | $CH_3$ | 6-$CH_3$ | $CH_3$ | $CH_3$ | 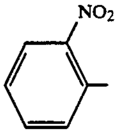 | |
| 352 | $CH_3$ | $CH_3$ | 6-$CH_3$ | $CH_3$ | $CH_3$ | 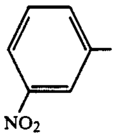 | |
| 353 | $CH_3$ | $CH_3$ | 6-$CH_3$ | $CH_3$ | $CH_3$ | 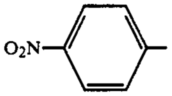 | |
| 354 | $CH_3$ | $CH_3$ | 6-$CH_3$ | $CH_3$ | $CH_3$ | 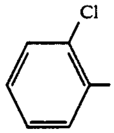 | |
| 355 | $CH_3$ | $CH_3$ | 6-$CH_3$ | $CH_3$ | $CH_3$ | 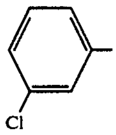 | |
| 356 | $CH_3$ | $CH_3$ | 6-$CH_3$ | $CH_3$ | $CH_3$ | 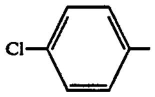 | |
| 357 | $CH_3$ | $CH_3$ | 6-$CH_3$ | $CH_3$ | $CH_3$ | 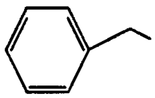 | |
| 358 | $CH_3$ | $CH_3$ | 6-$CH_3$ | $C_2H_5$ | $CH_3$ | $CH_3$ | |
| 359 | $CH_3$ | $CH_3$ | 6-$CH_3$ | $C_2H_5$ | $CH_3$ | $(CH_3)_2CH-$ | |
| 360 | $CH_3$ | $CH_3$ | 6-$CH_3$ | $C_2H_5$ | $CH_3$ | $(CH_3)_3C-$ | |
| 361 | $CH_3$ | $CH_3$ | 6-$CH_3$ | $C_2H_5$ | $CH_3$ | $CH_3-(CH_2)_3-$ | |
| 362 | $CH_3$ | $CH_3$ | 6-$CH_3$ | $C_2H_5$ | $CH_3$ | $C_2H_5-C(CH_3)_2$ | |
| 363 | $CH_3$ | $CH_3$ | 6-$CH_3$ | $C_2H_5$ | $CH_3$ | $(CH_3)_3C-CH_2-$ | |

TABLE 2-continued (Ib)

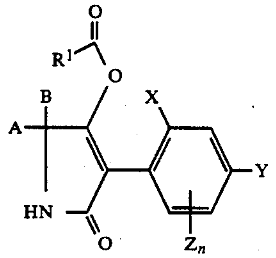

| Ex.-No. | X | Y | $Z_n$ | A | B | $R^1$ | Mp °C. |
|---|---|---|---|---|---|---|---|
| 364 | $CH_3$ | $CH_3$ | 6-$CH_3$ | $C_2H_5$ | $CH_3$ | $(CH_3)_2CH-C(CH_3)_2$ | |
| 365 | $CH_3$ | $CH_3$ | 6-$CH_3$ | $C_2H_5$ | $CH_3$ | $CH_2=CH-(CH_2)_8-$ | |
| 366 | $CH_3$ | $CH_3$ | 6-$CH_3$ | $C_2H_5$ | $CH_3$ | 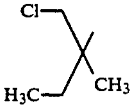 | |
| 367 | $CH_3$ | $CH_3$ | 6-$CH_3$ | $C_2H_5$ | $CH_3$ | $C_4H_9-CH-C_2H_5$ | |
| 368 | $CH_3$ | $CH_3$ | 6-$CH_3$ | $C_2H_5$ | $CH_3$ | 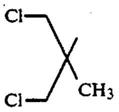 | |
| 369 | $CH_3$ | $CH_3$ | 6-$CH_3$ | $C_2H_5$ | $CH_3$ | 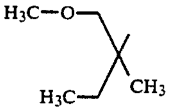 | |
| 370 | $CH_3$ | $CH_3$ | 6-$CH_3$ | $C_2H_5$ | $CH_3$ | 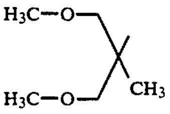 | |
| 371 | $CH_3$ | $CH_3$ | 6-$CH_3$ | $C_2H_5$ | $CH_3$ | 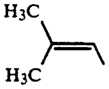 | |
| 372 | $CH_3$ | $CH_3$ | 6-$CH_3$ | $C_2H_5$ | $CH_3$ | $H_3C-S-CH_2-$ | |
| 373 | $CH_3$ | $CH_3$ | 6-$CH_3$ | $C_2H_5$ | $CH_3$ | 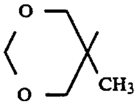 | |
| 374 | $CH_3$ | $CH_3$ | 6-$CH_3$ | $C_2H_5$ | $CH_3$ | 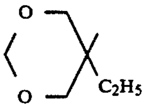 | |
| 375 | $CH_3$ | $CH_3$ | 6-$CH_3$ | $C_2H_5$ | $CH_3$ | 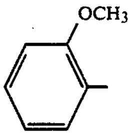 | |

TABLE 2-continued
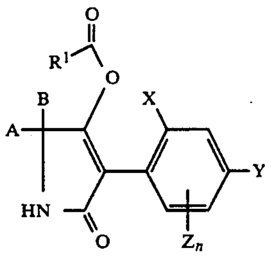
(Ib)
| Ex.-No. | X | Y | $Z_n$ | A | B | $R^1$ | Mp °C. |
|---|---|---|---|---|---|---|---|
| 376 | $CH_3$ | $CH_3$ | 6-$CH_3$ | $C_2H_5$ | $CH_3$ | 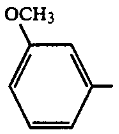 | |
| 377 | $CH_3$ | $CH_3$ | 6-$CH_3$ | $C_2H_5$ | $CH_3$ | 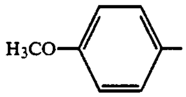 | |
| 378 | $CH_3$ | $CH_3$ | 6-$CH_3$ | $C_2H_5$ | $CH_3$ | 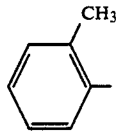 | |
| 379 | $CH_3$ | $CH_3$ | 6-$CH_3$ | $C_2H_5$ | $CH_3$ | 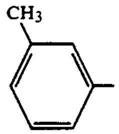 | |
| 380 | $CH_3$ | $CH_3$ | 6-$CH_3$ | $C_2H_5$ | $CH_3$ | 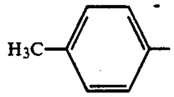 | |
| 381 | $CH_3$ | $CH_3$ | 6-$CH_3$ | $C_2H_5$ | $CH_3$ | 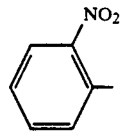 | |
| 382 | $CH_3$ | $CH_3$ | 6-$CH_3$ | $C_2H_5$ | $CH_3$ | 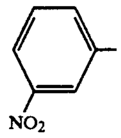 | |
| 383 | $CH_3$ | $CH_3$ | 6-$CH_3$ | $C_2H_5$ | $CH_3$ | 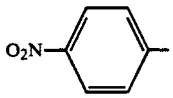 | |
| 384 | $CH_3$ | $CH_3$ | 6-$CH_3$ | $C_2H_5$ | $CH_3$ | 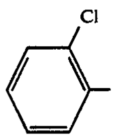 | |

TABLE 2-continued (Ib)

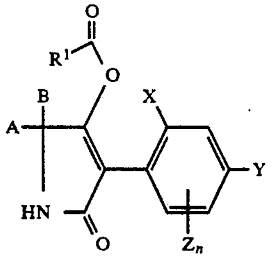

| Ex.-No. | X | Y | $Z_n$ | A | B | $R^1$ | Mp °C. |
|---|---|---|---|---|---|---|---|
| 385 | $CH_3$ | $CH_3$ | 6-$CH_3$ | $C_2H_5$ | $CH_3$ | 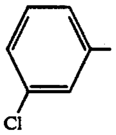 | |
| 386 | $CH_3$ | $CH_3$ | 6-$CH_3$ | $C_2H_5$ | $CH_3$ | 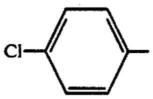 | |
| 387 | $CH_3$ | $CH_3$ | 6-$CH_3$ | $C_2H_5$ | $CH_3$ | 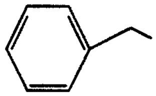 | |
| 388 | $CH_3$ | $CH_3$ | 6-$CH_3$ | $C_2H_5$ | $C_2H_5$ | $CH_3$ | |
| 389 | $CH_3$ | $CH_3$ | 6-$CH_3$ | $C_2H_5$ | $C_2H_5$ | $(CH_3)_2CH-$ | |
| 390 | $CH_3$ | $CH_3$ | 6-$CH_3$ | $C_2H_5$ | $C_2H_5$ | $(CH_3)_3C-$ | |
| 391 | $CH_3$ | $CH_3$ | 6-$CH_3$ | $C_2H_5$ | $C_2H_5$ | $CH_3-(CH_2)_3-$ | |
| 392 | $CH_3$ | $CH_3$ | 6-$CH_3$ | $C_2H_5$ | $C_2H_5$ | $C_2H_5-C(CH_3)_2$ | |
| 393 | $CH_3$ | $CH_3$ | 6-$CH_3$ | $C_2H_5$ | $C_2H_5$ | $(CH_3)_3C-CH_2-$ | |
| 394 | $CH_3$ | $CH_3$ | 6-$CH_3$ | $C_2H_5$ | $C_2H_5$ | $(CH_3)_2CH-C(CH_3)_2$ | |
| 395 | $CH_3$ | $CH_3$ | 6-$CH_3$ | $C_2H_5$ | $C_2H_5$ | $CH_2{=}CH-(CH_2)_8-$ | |
| 396 | $CH_3$ | $CH_3$ | 6-$CH_3$ | $C_2H_5$ | $C_2H_5$ | 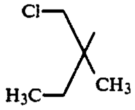 | |
| 397 | $CH_3$ | $CH_3$ | 6-$CH_3$ | $C_2H_5$ | $C_2H_5$ | $C_4H_9-CH-C_2H_5$ | |
| 398 | $CH_3$ | $CH_3$ | 6-$CH_3$ | $C_2H_5$ | $C_2H_5$ | 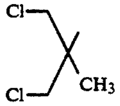 | |
| 399 | $CH_3$ | $CH_3$ | 6-$CH_3$ | $C_2H_5$ | $C_2H_5$ | 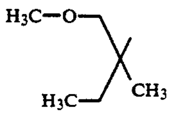 | |
| 400 | $CH_3$ | $CH_3$ | 6-$CH_3$ | $C_2H_5$ | $C_2H_5$ | 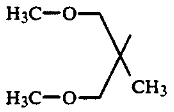 | |

TABLE 2-continued
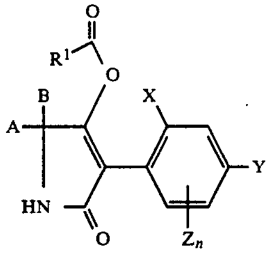
(Ib)
| Ex.-No. | X | Y | $Z_n$ | A | B | $R^1$ | Mp °C. |
|---|---|---|---|---|---|---|---|
| 401 | $CH_3$ | $CH_3$ | 6-$CH_3$ | $C_2H_5$ | $C_2H_5$ | 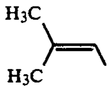 | |
| 402 | $CH_3$ | $CH_3$ | 6-$CH_3$ | $C_2H_5$ | $C_2H_5$ | $H_3C-S-CH_2-$ | |
| 403 | $CH_3$ | $CH_3$ | 6-$CH_3$ | $C_2H_5$ | $C_2H_5$ | 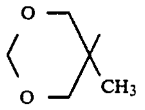 | |
| 404 | $CH_3$ | $CH_3$ | 6-$CH_3$ | $C_2H_5$ | $C_2H_5$ | 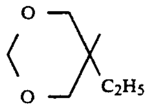 | |
| 405 | $CH_3$ | $CH_3$ | 6-$CH_3$ | $C_2H_5$ | $C_2H_5$ | 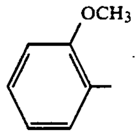 | |
| 406 | $CH_3$ | $CH_3$ | 6-$CH_3$ | $C_2H_5$ | $C_2H_5$ | 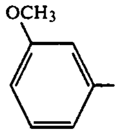 | |
| 407 | $CH_3$ | $CH_3$ | 6-$CH_3$ | $C_2H_5$ | $C_2H_5$ | 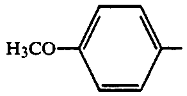 | |
| 408 | $CH_3$ | $CH_3$ | 6-$CH_3$ | $C_2H_5$ | $C_2H_5$ | 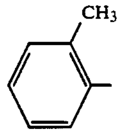 | |
| 409 | $CH_3$ | $CH_3$ | 6-$CH_3$ | $C_2H_5$ | $C_2H_5$ | 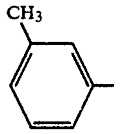 | |
| 410 | $CH_3$ | $CH_3$ | 6-$CH_3$ | $C_2H_5$ | $C_2H_5$ | 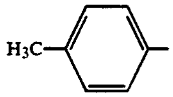 | |
| 411 | $CH_3$ | $CH_3$ | 6-$CH_3$ | $C_2H_5$ | $C_2H_5$ | 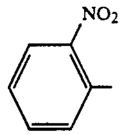 | |

TABLE 2-continued (Ib)

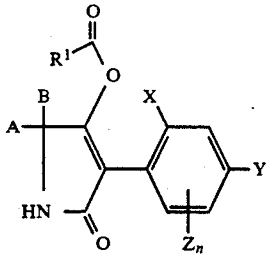

| Ex.-No. | X | Y | $Z_n$ | A | B | $R^1$ | Mp °C. |
|---|---|---|---|---|---|---|---|
| 412 | $CH_3$ | $CH_3$ | 6-$CH_3$ | $C_2H_5$ | $C_2H_5$ | 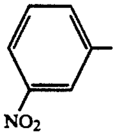 | |
| 413 | $CH_3$ | $CH_3$ | 6-$CH_3$ | $C_2H_5$ | $C_2H_5$ | 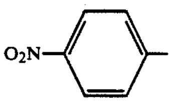 | |
| 414 | $CH_3$ | $CH_3$ | 6-$CH_3$ | $C_2H_5$ | $C_2H_5$ | 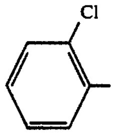 | |
| 415 | $CH_3$ | $CH_3$ | 6-$CH_3$ | $C_2H_5$ | $C_2H_5$ | 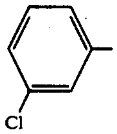 | |
| 416 | $CH_3$ | $CH_3$ | 6-$CH_3$ | $C_2H_5$ | $C_2H_5$ | 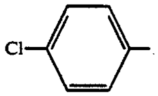 | |
| 417 | $CH_3$ | $CH_3$ | 6-$CH_3$ | $C_2H_5$ | $C_2H_5$ | 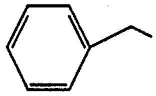 | |
| 418 | $CH_3$ | $CH_3$ | 6-$CH_3$ | $C_3H_7$ | $CH_3$ | $CH_3$ | |
| 419 | $CH_3$ | $CH_3$ | 6-$CH_3$ | $C_3H_7$ | $CH_3$ | $(CH_3)_2CH-$ | |
| 420 | $CH_3$ | $CH_3$ | 6-$CH_3$ | $C_3H_7$ | $CH_3$ | $(CH_3)_3C-$ | |
| 421 | $CH_3$ | $CH_3$ | 6-$CH_3$ | $C_3H_7$ | $CH_3$ | $CH_3-(CH_2)_3-$ | |
| 422 | $CH_3$ | $CH_3$ | 6-$CH_3$ | $C_3H_7$ | $CH_3$ | $C_2H_5-C(CH_3)_2-$ | |
| 423 | $CH_3$ | $CH_3$ | 6-$CH_3$ | $C_3H_7$ | $CH_3$ | $(CH_3)_3C-CH_2-$ | |
| 424 | $CH_3$ | $CH_3$ | 6-$CH_3$ | $C_3H_7$ | $CH_3$ | $(CH_3)_2CH-C(CH_3)_2-$ | |
| 425 | $CH_3$ | $CH_3$ | 6-$CH_3$ | $C_3H_7$ | $CH_3$ | $CH_2=CH-(CH_2)_8-$ | |
| 426 | $CH_3$ | $CH_3$ | 6-$CH_3$ | $C_3H_7$ | $CH_3$ | 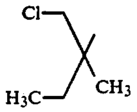 | |
| 427 | $CH_3$ | $CH_3$ | 6-$CH_3$ | $C_3H_7$ | $CH_3$ | $C_4H_9-CH(-)-C_2H_5$ | |

TABLE 2-continued
(Ib)
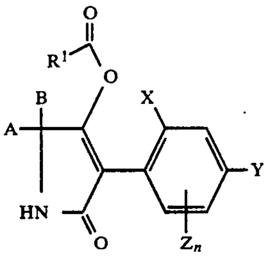
| Ex.-No. | X | Y | $Z_n$ | A | B | $R^1$ | Mp °C. |
|---|---|---|---|---|---|---|---|
| 428 | $CH_3$ | $CH_3$ | 6-$CH_3$ | $C_3H_7$ | $CH_3$ | 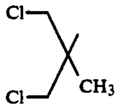 | |
| 429 | $CH_3$ | $CH_3$ | 6-$CH_3$ | $C_3H_7$ | $CH_3$ | 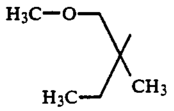 | |
| 430 | $CH_3$ | $CH_3$ | 6-$CH_3$ | $C_3H_7$ | $CH_3$ | 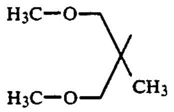 | |
| 431 | $CH_3$ | $CH_3$ | 6-$CH_3$ | $C_3H_7$ | $CH_3$ | 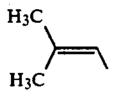 | |
| 432 | $CH_3$ | $CH_3$ | 6-$CH_3$ | $C_3H_7$ | $CH_3$ | $H_3C-S-CH_2-$ | |
| 433 | $CH_3$ | $CH_3$ | 6-$CH_3$ | $C_3H_7$ | $CH_3$ | 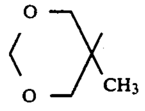 | |
| 434 | $CH_3$ | $CH_3$ | 6-$CH_3$ | $C_3H_7$ | $CH_3$ | 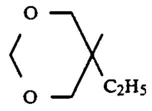 | |
| 435 | $CH_3$ | $CH_3$ | 6-$CH_3$ | $C_3H_7$ | $CH_3$ | 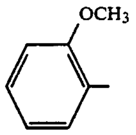 | |
| 436 | $CH_3$ | $CH_3$ | 6-$CH_3$ | $C_3H_7$ | $CH_3$ | 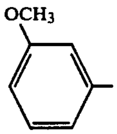 | |
| 437 | $CH_3$ | $CH_3$ | 6-$CH_3$ | $C_3H_7$ | $CH_3$ | 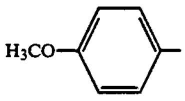 | |
| 438 | $CH_3$ | $CH_3$ | 6-$CH_3$ | $C_3H_7$ | $CH_3$ | 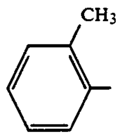 | |

TABLE 2-continued (Ib)

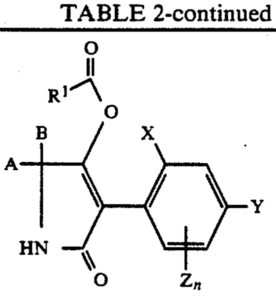

| Ex.-No. | X | Y | $Z_n$ | A | B | $R^1$ | Mp °C. |
|---|---|---|---|---|---|---|---|
| 439 | $CH_3$ | $CH_3$ | 6-$CH_3$ | $C_3H_7$ | $CH_3$ | 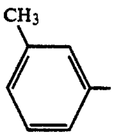 | |
| 440 | $CH_3$ | $CH_3$ | 6-$CH_3$ | $C_3H_7$ | $CH_3$ | 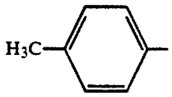 | |
| 441 | $CH_3$ | $CH_3$ | 6-$CH_3$ | $C_3H_7$ | $CH_3$ | 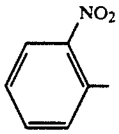 | |
| 442 | $CH_3$ | $CH_3$ | 6-$CH_3$ | $C_3H_7$ | $CH_3$ | 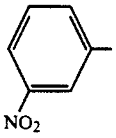 | |
| 443 | $CH_3$ | $CH_3$ | 6-$CH_3$ | $C_3H_7$ | $CH_3$ | 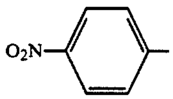 | |
| 444 | $CH_3$ | $CH_3$ | 6-$CH_3$ | $C_3H_7$ | $CH_3$ | 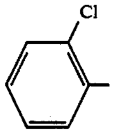 | |
| 445 | $CH_3$ | $CH_3$ | 6-$CH_3$ | $C_3H_7$ | $CH_3$ | 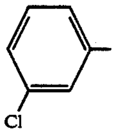 | |
| 446 | $CH_3$ | $CH_3$ | 6-$CH_3$ | $C_3H_7$ | $CH_3$ | 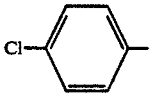 | |
| 447 | $CH_3$ | $CH_3$ | 6-$CH_3$ | $C_3H_7$ | $CH_3$ | 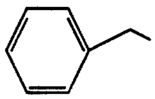 | |
| 448 | $CH_3$ | $CH_3$ | 6-$CH_3$ | i-$C_3H_7$ | $CH_3$ | $CH_3$ | |
| 449 | $CH_3$ | $CH_3$ | 6-$CH_3$ | i-$C_3H_7$ | $CH_3$ | $(CH_3)_2CH-$ | |
| 450 | $CH_3$ | $CH_3$ | 6-$CH_3$ | i-$C_3H_7$ | $CH_3$ | $(CH_3)_3C-$ | |
| 451 | $CH_3$ | $CH_3$ | 6-$CH_3$ | i-$C_3H_7$ | $CH_3$ | $CH_3-(CH_2)_3-$ | |

TABLE 2-continued (Ib)

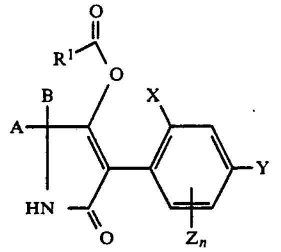

| Ex.-No. | X | Y | $Z_n$ | A | B | $R^1$ | Mp °C. |
|---|---|---|---|---|---|---|---|
| 452 | $CH_3$ | $CH_3$ | 6-$CH_3$ | i-$C_3H_7$ | $CH_3$ | $C_2H_5-C(CH_3)_2$ | |
| 453 | $CH_3$ | $CH_3$ | 6-$CH_3$ | i-$C_3H_7$ | $CH_3$ | $(CH_3)_3C-CH_2-$ | |
| 454 | $CH_3$ | $CH_3$ | 6-$CH_3$ | i-$C_3H_7$ | $CH_3$ | $(CH_3)_2CH-C(CH_3)_2$ | |
| 455 | $CH_3$ | $CH_3$ | 6-$CH_3$ | i-$C_3H_7$ | $CH_3$ | $CH_2=CH-(CH_2)_8-$ | |
| 456 | $CH_3$ | $CH_3$ | 6-$CH_3$ | i-$C_3H_7$ | $CH_3$ | 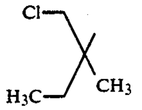 | |
| 457 | $CH_3$ | $CH_3$ | 6-$CH_3$ | i-$C_3H_7$ | $CH_3$ | $C_4H_9-CH-C_2H_5$ | |
| 458 | $CH_3$ | $CH_3$ | 6-$CH_3$ | i-$C_3H_7$ | $CH_3$ | 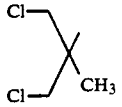 | |
| 459 | $CH_3$ | $CH_3$ | 6-$CH_3$ | i-$C_3H_7$ | $CH_3$ | 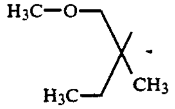 | |
| 460 | $CH_3$ | $CH_3$ | 6-$CH_3$ | i-$C_3H_7$ | $CH_3$ | 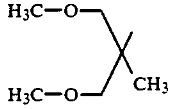 | |
| 461 | $CH_3$ | $CH_3$ | 6-$CH_3$ | i-$C_3H_7$ | $CH_3$ | 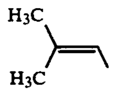 | |
| 462 | $CH_3$ | $CH_3$ | 6-$CH_3$ | i-$C_3H_7$ | $CH_3$ | $H_3C-S-CH_2-$ | |
| 463 | $CH_3$ | $CH_3$ | 6-$CH_3$ | i-$C_3H_7$ | $CH_3$ | 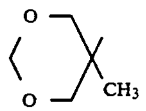 | |
| 464 | $CH_3$ | $CH_3$ | 6-$CH_3$ | i-$C_3H_7$ | $CH_3$ | 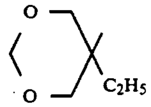 | |
| 465 | $CH_3$ | $CH_3$ | 6-$CH_3$ | i-$C_3H_7$ | $CH_3$ | 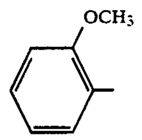 | |

TABLE 2-continued
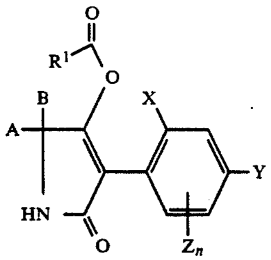
(Ib)
| Ex.-No. | X | Y | $Z_n$ | A | B | $R^1$ | Mp °C. |
|---|---|---|---|---|---|---|---|
| 466 | $CH_3$ | $CH_3$ | 6-$CH_3$ | i-$C_3H_7$ | $CH_3$ | 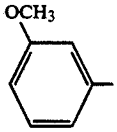 | |
| 467 | $CH_3$ | $CH_3$ | 6-$CH_3$ | i-$C_3H_7$ | $CH_3$ | 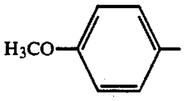 | |
| 468 | $CH_3$ | $CH_3$ | 6-$CH_3$ | i-$C_3H_7$ | H | 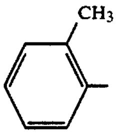 | |
| 469 | $CH_3$ | $CH_3$ | 6-$CH_3$ | i-$C_3H_7$ | H | 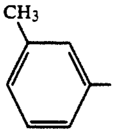 | |
| 470 | $CH_3$ | $CH_3$ | 6-$CH_3$ | i-$C_3H_7$ | H | 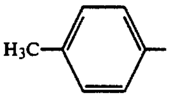 | |
| 471 | $CH_3$ | $CH_3$ | 6-$CH_3$ | i-$C_3H_7$ | H | 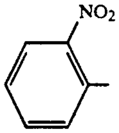 | |
| 472 | $CH_3$ | $CH_3$ | 6-$CH_3$ | i-$C_3H_7$ | H | 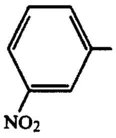 | |
| 473 | $CH_3$ | $CH_3$ | 6-$CH_3$ | i-$C_3H_7$ | H | 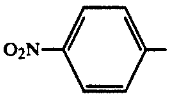 | |
| 474 | $CH_3$ | $CH_3$ | 6-$CH_3$ | i-$C_3H_7$ | H | 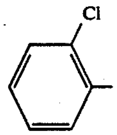 | |

TABLE 2-continued (Ib)

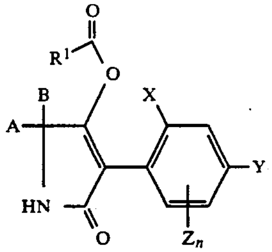

| Ex.-No. | X | Y | $Z_n$ | A | B | $R^1$ | Mp °C. |
|---|---|---|---|---|---|---|---|
| 475 | $CH_3$ | $CH_3$ | 6-$CH_3$ | i-$C_3H_7$ | H | 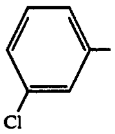 | |
| 476 | $CH_3$ | $CH_3$ | 6-$CH_3$ | i-$C_3H_7$ | H | 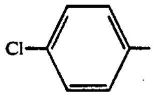 | |
| 477 | $CH_3$ | $CH_3$ | 6-$CH_3$ | i-$C_3H_7$ | H | 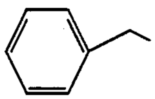 | |
| 478 | $CH_3$ | $CH_3$ | 6-$CH_3$ | $-(CH_2)_4-$ | | $CH_3$ | |
| 479 | $CH_3$ | $CH_3$ | 6-$CH_3$ | $-(CH_2)_4-$ | | $(CH_3)_2CH-$ | |
| 480 | $CH_3$ | $CH_3$ | 6-$CH_3$ | $-(CH_2)_4-$ | | $(CH_3)_3C-$ | |
| 481 | $CH_3$ | $CH_3$ | 6-$CH_3$ | $-(CH_2)_4-$ | | $CH_3-(CH_2)_3-$ | |
| 482 | $CH_3$ | $CH_3$ | 6-$CH_3$ | $-(CH_2)_4-$ | | $C_2H_5-C(CH_3)_2$ | |
| 483 | $CH_3$ | $CH_3$ | 6-$CH_3$ | $-(CH_2)_4-$ | | $(CH_3)_3C-CH_2-$ | |
| 484 | $CH_3$ | $CH_3$ | 6-$CH_3$ | $-(CH_2)_4-$ | | $(CH_3)_2CH-C(CH_3)_2$ | |
| 485 | $CH_3$ | $CH_3$ | 6-$CH_3$ | $-(CH_2)_4-$ | | $CH_2=CH-(CH_2)_8-$ | |
| 486 | $CH_3$ | $CH_3$ | 6-$CH_3$ | $-(CH_2)_4-$ | | 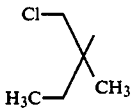 | |
| 487 | $CH_3$ | $CH_3$ | 6-$CH_3$ | $-(CH_2)_4-$ | | $C_4H_9-CH-C_2H_5$ | |
| 488 | $CH_3$ | $CH_3$ | 6-$CH_3$ | $-(CH_2)_4-$ | | 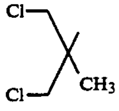 | |
| 489 | $CH_3$ | $CH_3$ | 6-$CH_3$ | $-(CH_2)_4-$ | | 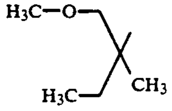 | |
| 490 | $CH_3$ | $CH_3$ | 6-$CH_3$ | $-(CH_2)_4-$ | | 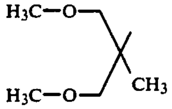 | |

TABLE 2-continued
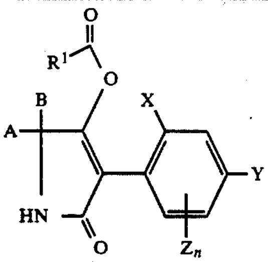
(Ib)
| Ex.-No. | X | Y | $Z_n$ | A B | $R^1$ | Mp °C. |
|---|---|---|---|---|---|---|
| 491 | $CH_3$ | $CH_3$ | 6-$CH_3$ | $-(CH_2)_4-$ | 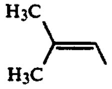 | |
| 492 | $CH_3$ | $CH_3$ | 6-$CH_3$ | $-(CH_2)_4-$ | $H_3C-S-CH_2-$ | |
| 493 | $CH_3$ | $CH_3$ | 6-$CH_3$ | $-(CH_2)_4-$ | 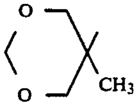 | |
| 494 | $CH_3$ | $CH_3$ | 6-$CH_3$ | $-(CH_2)_4-$ | 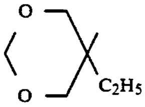 | |
| 495 | $CH_3$ | $CH_3$ | 6-$CH_3$ | $-(CH_2)_4-$ | 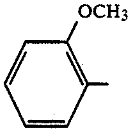 | |
| 496 | $CH_3$ | $CH_3$ | 6-$CH_3$ | $-(CH_2)_4-$ | 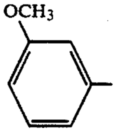 | |
| 497 | $CH_3$ | $CH_3$ | 6-$CH_3$ | $-(CH_2)_4-$ | 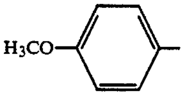 | |
| 498 | $CH_3$ | $CH_3$ | 6-$CH_3$ | $-(CH_2)_4-$ | 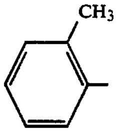 | |
| 499 | $CH_3$ | $CH_3$ | 6-$CH_3$ | $-(CH_2)_4-$ | 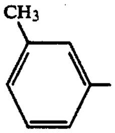 | |
| 500 | $CH_3$ | $CH_3$ | 6-$CH_3$ | $-(CH_2)_4-$ | 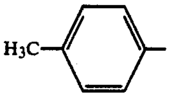 | |
| 501 | $CH_3$ | $CH_3$ | 6-$CH_3$ | $-(CH_2)_4-$ | 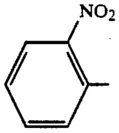 | |

TABLE 2-continued

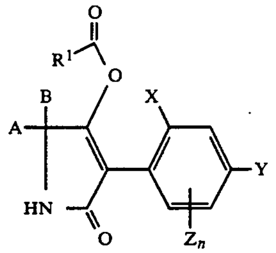

(Ib)

| Ex.-No. | X | Y | $Z_n$ | A | B | $R^1$ | Mp °C. |
|---|---|---|---|---|---|---|---|
| 502 | $CH_3$ | $CH_3$ | 6-$CH_3$ | $-(CH_2)_4-$ | | 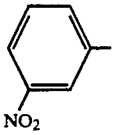 | |
| 503 | $CH_3$ | $CH_3$ | 6-$CH_3$ | $-(CH_2)_4-$ | | 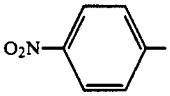 | |
| 504 | $CH_3$ | $CH_3$ | 6-$CH_3$ | $-(CH_2)_4-$ | | 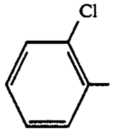 | |
| 505 | $CH_3$ | $CH_3$ | 6-$CH_3$ | $-(CH_2)_4-$ | | 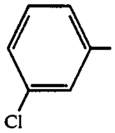 | |
| 506 | $CH_3$ | $CH_3$ | 6-$CH_3$ | $-(CH_2)_4-$ | | 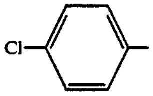 | |
| 507 | $CH_3$ | $CH_3$ | 6-$CH_3$ | $-(CH_2)_4-$ | | 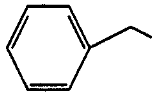 | |
| 508 | $CH_3$ | $CH_3$ | 6-$CH_3$ | $-(CH_2)_5-$ | | $CH_3$ | |
| 509 | $CH_3$ | $CH_3$ | 6-$CH_3$ | $-(CH_2)_5-$ | | $(CH_3)_2CH-$ | |
| 510 | $CH_3$ | $CH_3$ | 6-$CH_3$ | $-(CH_2)_5-$ | | $(CH_3)_3C-$ | |
| 511 | $CH_3$ | $CH_3$ | 6-$CH_3$ | $-(CH_2)_5-$ | | $CH_3-(CH_2)_3-$ | |
| 512 | $CH_3$ | $CH_3$ | 6-$CH_3$ | $-(CH_2)_5-$ | | $C_2H_5-C(CH_3)_2$ | |
| 513 | $CH_3$ | $CH_3$ | 6-$CH_3$ | $-(CH_2)_5-$ | | $(CH_3)_3C-CH_2-$ | |
| 514 | $CH_3$ | $CH_3$ | 6-$CH_3$ | $-(CH_2)_5-$ | | $(CH_3)_2CH-C(CH_3)_2$ | |
| 515 | $CH_3$ | $CH_3$ | 6-$CH_3$ | $-(CH_2)_5-$ | | $CH_2{=}CH-(CH_2)_8-$ | |
| 516 | $CH_3$ | $CH_3$ | 6-$CH_3$ | $-(CH_2)_5-$ | | 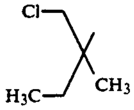 | |
| 517 | $CH_3$ | $CH_3$ | 6-$CH_3$ | $-(CH_2)_5-$ | | $C_4H_9-CH-C_2H_5$ | |

TABLE 2-continued
(Ib)
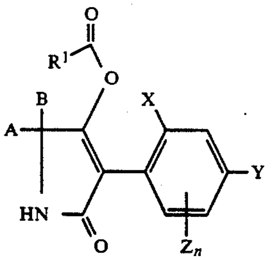
| Ex.-No. | X | Y | $Z_n$ | A | B | $R^1$ | Mp °C. |
|---|---|---|---|---|---|---|---|
| 518 | $CH_3$ | $CH_3$ | 6-$CH_3$ | $-(CH_2)_5-$ | | 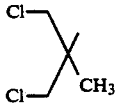 | |
| 519 | $CH_3$ | $CH_3$ | 6-$CH_3$ | $-(CH_2)_5-$ | | 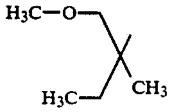 | |
| 520 | $CH_3$ | $CH_3$ | 6-$CH_3$ | $-(CH_2)_5-$ | | 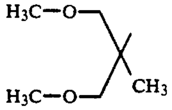 | |
| 521 | $CH_3$ | $CH_3$ | 6-$CH_3$ | $-(CH_2)_5-$ | | 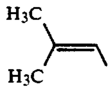 | |
| 522 | $CH_3$ | $CH_3$ | 6-$CH_3$ | $-(CH_2)_5-$ | | $H_3C-S-CH_2-$ | |
| 523 | $CH_3$ | $CH_3$ | 6-$CH_3$ | $-(CH_2)_5-$ | | 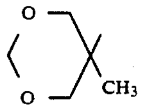 | |
| 524 | $CH_3$ | $CH_3$ | 6-$CH_3$ | $-(CH_2)_5-$ | | 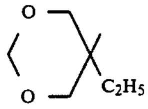 | |
| 525 | $CH_3$ | $CH_3$ | 6-$CH_3$ | $-(CH_2)_5-$ | | 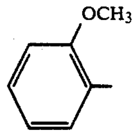 | |
| 526 | $CH_3$ | $CH_3$ | 6-$CH_3$ | $-(CH_2)_5-$ | | 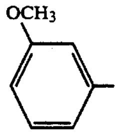 | |
| 527 | $CH_3$ | $CH_3$ | 6-$CH_3$ | $-(CH_2)_5-$ | | 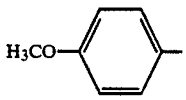 | |
| 528 | $CH_3$ | $CH_3$ | 6-$CH_3$ | $-(CH_2)_5-$ | | 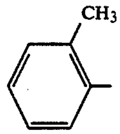 | |

TABLE 2-continued
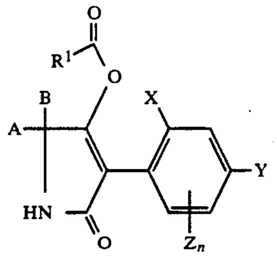
(Ib)
| Ex.-No. | X | Y | $Z_n$ | A | B | $R^1$ | Mp °C. |
| --- | --- | --- | --- | --- | --- | --- | --- |
| 529 | $CH_3$ | $CH_3$ | 6-$CH_3$ | $-(CH_2)_5-$ | | 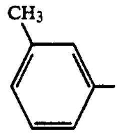 | |
| 530 | $CH_3$ | $CH_3$ | 6-$CH_3$ | $-(CH_2)_5-$ | | 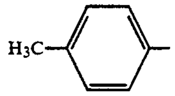 | |
| 531 | $CH_3$ | $CH_3$ | 6-$CH_3$ | $-(CH_2)_5-$ | | 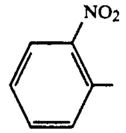 | |
| 532 | $CH_3$ | $CH_3$ | 6-$CH_3$ | $-(CH_2)_5-$ | | 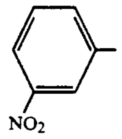 | |
| 533 | $CH_3$ | $CH_3$ | 6-$CH_3$ | $-(CH_2)_5-$ | | 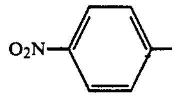 | |
| 534 | $CH_3$ | $CH_3$ | 6-$CH_3$ | $-(CH_2)_5-$ | | 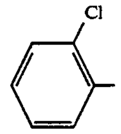 | |
| 535 | $CH_3$ | $CH_3$ | 6-$CH_3$ | $-(CH_2)_5-$ | | 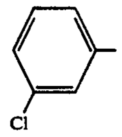 | |
| 536 | $CH_3$ | $CH_3$ | 6-$CH_3$ | $-(CH_2)_5-$ | | 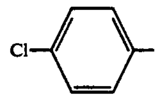 | |
| 537 | $CH_3$ | $CH_3$ | 6-$CH_3$ | $-(CH_2)_5-$ | | 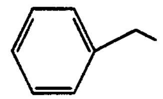 | |

TABLE 3

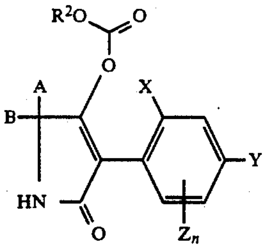

(Ic)

| Ex.-No. | X | Y | $Z_n$ | A | B | $R^2$ | Mp °C. |
|---|---|---|---|---|---|---|---|
| 538 | Cl | Cl | H | $CH_3$ | $CH_3$ | $CH_3$ | |
| 539 | Cl | Cl | H | $CH_3$ | $CH_3$ | $C_2H_5$ | |
| 540 | Cl | Cl | H | $CH_3$ | $CH_3$ | $(CH_3)_2CH-$ | |
| 541 | Cl | Cl | H | $CH_3$ | $CH_3$ | $(CH_3)_2CH-CH_2-$ | |
| 542 | Cl | Cl | H | $CH_3$ | $CH_3$ | $C_2H_5-CH-$<br>$CH_3$ | |
| 543 | Cl | Cl | H | $CH_3$ | $CH_3$ | $(CH_3)_3C-$ | |
| 544 | Cl | Cl | H | $CH_3$ | $CH_3$ | $(CH_3)_3C-CH_2-$ | |
| 545 | Cl | Cl | H | $CH_3$ | $CH_3$ | 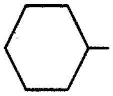 | |
| 546 | Cl | Cl | H | $CH_3$ | $CH_3$ | 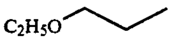 | |
| 547 | Cl | Cl | H | $CH_3$ | $CH_3$ | 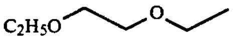 | |
| 548 | Cl | Cl | H | $CH_3$ | $CH_3$ | 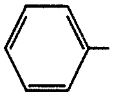 | |
| 549 | Cl | Cl | H | $CH_3$ | $CH_3$ | 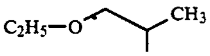 | |
| 550 | Cl | Cl | H | $CH_3$ | $CH_3$ | 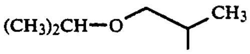 | |
| 551 | Cl | Cl | H | $CH_3$ | $CH_3$ | 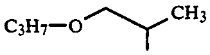 | |
| 552 | Cl | Cl | H | $CH_3$ | $CH_3$ | 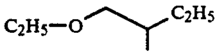 | |
| 553 | Cl | Cl | H | $C_2H_5$ | $CH_3$ | $CH_3$ | |
| 554 | Cl | Cl | H | $C_2H_5$ | $CH_3$ | $C_2H_5$ | |
| 555 | Cl | Cl | H | $C_2H_5$ | $CH_3$ | $(CH_3)_2CH-$ | |
| 556 | Cl | Cl | H | $C_2H_5$ | $CH_3$ | $(CH_3)_2CH-CH_2-$ | |
| 557 | Cl | Cl | H | $C_2H_5$ | $CH_3$ | $C_2H_5-CH-$<br>$CH_3$ | |
| 558 | Cl | Cl | H | $C_2H_5$ | $CH_3$ | $(CH_3)_3C-$ | |
| 559 | Cl | Cl | H | $C_2H_5$ | $CH_3$ | $(CH_3)_3C-CH_2-$ | |
| 560 | Cl | Cl | H | $C_2H_5$ | $CH_3$ | 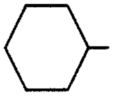 | |
| 561 | Cl | Cl | H | $C_2H_5$ | $CH_3$ | 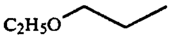 | |

TABLE 3-continued

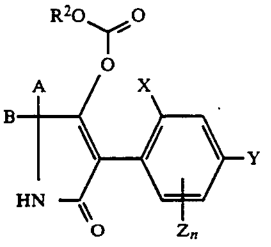

(Ic)

| Ex.-No. | X | Y | $Z_n$ | A | B | $R^2$ | Mp °C. |
|---|---|---|---|---|---|---|---|
| 562 | Cl | Cl | H | $C_2H_5$ | $CH_3$ | 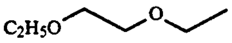 | |
| 563 | Cl | Cl | H | $C_2H_5$ | $CH_3$ | 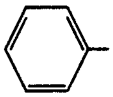 | |
| 564 | Cl | Cl | H | $C_2H_5$ | $CH_3$ | 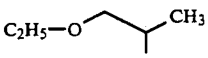 | |
| 565 | Cl | Cl | H | $C_2H_5$ | $CH_3$ | 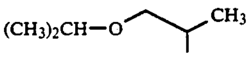 | |
| 566 | Cl | Cl | H | $C_2H_5$ | $CH_3$ | 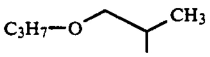 | |
| 567 | Cl | Cl | H | $C_2H_5$ | $CH_3$ | 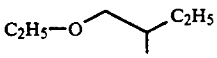 | |
| 568 | Cl | Cl | H | $C_2H_5$ | $C_2H_5$ | $CH_3$ | |
| 569 | Cl | Cl | H | $C_2H_5$ | $C_2H_5$ | $C_2H_5$ | |
| 570 | Cl | Cl | H | $C_2H_5$ | $C_2H_5$ | $(CH_3)_2CH-$ | |
| 571 | Cl | Cl | H | $C_2H_5$ | $C_2H_5$ | $(CH_3)_2CH-CH_2-$ | |
| 572 | Cl | Cl | H | $C_2H_5$ | $C_2H_5$ | $C_2H_5-CH-$<br>$CH_3$ | |
| 573 | Cl | Cl | H | $C_2H_5$ | $C_2H_5$ | $(CH_3)_3C-$ | |
| 574 | Cl | Cl | H | $C_2H_5$ | $C_2H_5$ | $(CH_3)_3C-CH_2-$ | |
| 575 | Cl | Cl | H | $C_2H_5$ | $C_2H_5$ | 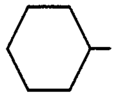 | |
| 576 | Cl | Cl | H | $C_2H_5$ | $C_2H_5$ | 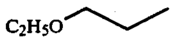 | |
| 577 | Cl | Cl | H | $C_2H_5$ | $C_2H_5$ | 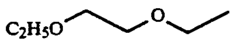 | |
| 578 | Cl | Cl | H | $C_2H_5$ | $C_2H_5$ | 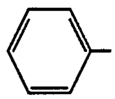 | |
| 579 | Cl | Cl | H | $C_2H_5$ | $C_2H_5$ | 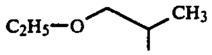 | |
| 580 | Cl | Cl | H | $C_2H_5$ | $C_2H_5$ | 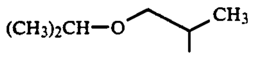 | |
| 581 | Cl | Cl | H | $C_2H_5$ | $C_2H_5$ | 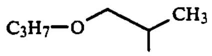 | |

TABLE 3-continued

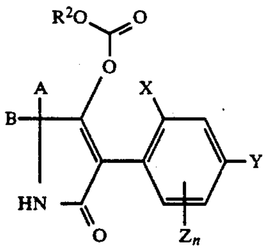

(Ic)

| Ex.-No. | X | Y | $Z_n$ | A | B | $R^2$ | Mp °C. |
|---|---|---|---|---|---|---|---|
| 582 | Cl | Cl | H | $C_2H_5$ | $C_2H_5$ | 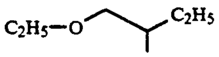 | |
| 583 | Cl | Cl | H | $C_3H_7$ | $CH_3$ | $CH_3$ | |
| 584 | Cl | Cl | H | $C_3H_7$ | $CH_3$ | $C_2H_5$ | |
| 585 | Cl | Cl | H | $C_3H_7$ | $CH_3$ | $(CH_3)_2CH-$ | |
| 586 | Cl | Cl | H | $C_3H_7$ | $CH_3$ | $(CH_3)_2CH-CH_2-$ | |
| 587 | Cl | Cl | H | $C_3H_7$ | $CH_3$ | $C_2H_5-CH-$<br>$CH_3$ | |
| 588 | Cl | Cl | H | $C_3H_7$ | $CH_3$ | $(CH_3)_3C-$ | |
| 589 | Cl | Cl | H | $C_3H_7$ | $CH_3$ | $(CH_3)_3C-CH_2-$ | |
| 590 | Cl | Cl | H | $C_3H_7$ | $CH_3$ | 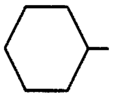 | |
| 591 | Cl | Cl | H | $C_3H_7$ | $CH_3$ | 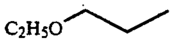 | |
| 592 | Cl | Cl | H | $C_3H_7$ | $CH_3$ | 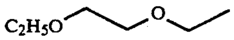 | |
| 593 | Cl | Cl | H | $C_3H_7$ | $CH_3$ | 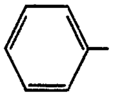 | |
| 594 | Cl | Cl | H | $C_3H_7$ | $CH_3$ | 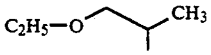 | |
| 595 | Cl | Cl | H | $C_3H_7$ | $CH_3$ | 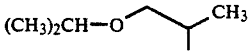 | |
| 596 | Cl | Cl | H | $C_3H_7$ | $CH_3$ | 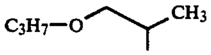 | |
| 597 | Cl | Cl | H | $C_3H_7$ | $CH_3$ | 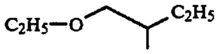 | |
| 598 | Cl | Cl | H | i-$C_3H_7$ | $CH_3$ | $CH_3$ | |
| 699 | Cl | Cl | H | i-$C_3H_7$ | $CH_3$ | $C_2H_5$ | |
| 600 | Cl | Cl | H | i-$C_3H_7$ | $CH_3$ | $(CH_3)_2CH-$ | |
| 601 | Cl | Cl | H | i-$C_3H_7$ | $CH_3$ | $(CH_3)_2CH-CH_2-$ | |
| 602 | Cl | Cl | H | i-$C_3H_7$ | $CH_3$ | $C_2H_5-CH-$<br>$CH_3$ | |
| 603 | Cl | Cl | H | i-$C_3H_7$ | $CH_3$ | $(CH_3)_3C-$ | |
| 604 | Cl | Cl | H | i-$C_3H_7$ | $CH_3$ | $(CH_3)_3C-CH_2-$ | |
| 605 | Cl | Cl | H | i-$C_3H_7$ | $CH_3$ | 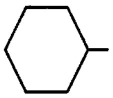 | |

TABLE 3-continued

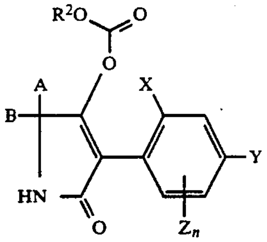

(Ic)

| Ex.-No. | X | Y | $Z_n$ | A | B | $R^2$ | Mp °C. |
|---|---|---|---|---|---|---|---|
| 606 | Cl | Cl | H | i-$C_3H_7$ | $CH_3$ | 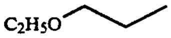 | |
| 607 | Cl | Cl | H | i-$C_3H_7$ | $CH_3$ | 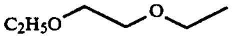 | |
| 608 | Cl | Cl | H | i-$C_3H_7$ | $CH_3$ | 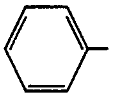 | |
| 609 | Cl | Cl | H | i-$C_3H_7$ | $CH_3$ | 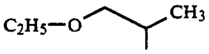 | |
| 610 | Cl | Cl | H | i-$C_3H_7$ | $CH_3$ | 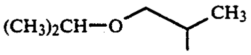 | |
| 611 | Cl | Cl | H | i-$C_3H_7$ | $CH_3$ | 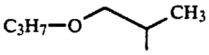 | |
| 612 | Cl | Cl | H | i-$C_3H_7$ | $CH_3$ | 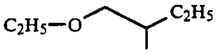 | |
| 613 | Cl | Cl | H | $-(CH_2)_4-$ | | $CH_3$ | |
| 614 | Cl | Cl | H | $-(CH_2)_4-$ | | $C_2H_5$ | |
| 615 | Cl | Cl | H | $-(CH_2)_4-$ | | $(CH_3)_2CH-$ | |
| 616 | Cl | Cl | H | $-(CH_2)_4-$ | | $(CH_3)_2CH-CH_2-$ | |
| 617 | Cl | Cl | H | $-(CH_2)_4-$ | | $C_2H_5-\underset{\displaystyle CH_3}{\underset{\mid}{CH}}-$ | |
| 618 | Cl | Cl | H | $-(CH_2)_4-$ | | $(CH_3)_3C-$ | |
| 619 | Cl | Cl | H | $-(CH_2)_4-$ | | $(CH_3)_3C-CH_2-$ | |
| 620 | Cl | Cl | H | $-(CH_2)_4-$ | | 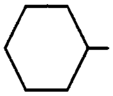 | |
| 621 | Cl | Cl | H | $-(CH_2)_4-$ | | 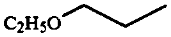 | |
| 622 | Cl | Cl | H | $-(CH_2)_4-$ | | 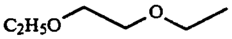 | |
| 623 | Cl | Cl | H | $-(CH_2)_4-$ | | 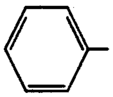 | |
| 624 | Cl | Cl | H | $-(CH_2)_4-$ | | 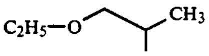 | |
| 625 | Cl | Cl | H | $-(CH_2)_4-$ | | 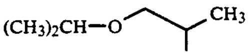 | |

TABLE 3-continued

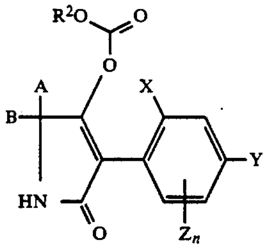

(Ic)

| Ex.-No. | X | Y | $Z_n$ | A | B | $R^2$ | Mp °C. |
|---|---|---|---|---|---|---|---|
| 626 | Cl | Cl | H | $-(CH_2)_4-$ | | 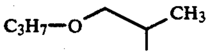 | |
| 627 | Cl | Cl | H | $-(CH_2)_4-$ | | 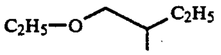 | |
| 628 | Cl | Cl | H | $-(CH_2)_5-$ | | $CH_3$ | |
| 629 | Cl | Cl | H | $-(CH_2)_5-$ | | $C_2H_5$ | |
| 630 | Cl | Cl | H | $-(CH_2)_5-$ | | $(CH_3)_2CH-$ | |
| 631 | Cl | Cl | H | $-(CH_2)_5-$ | | $(CH_3)_2CH-CH_2-$ | |
| 632 | Cl | Cl | H | $-(CH_2)_5-$ | | $C_2H_5-CH(CH_3)-$ | |
| 633 | Cl | Cl | H | $-(CH_2)_5-$ | | $(CH_3)_3C-$ | |
| 634 | Cl | Cl | H | $-(CH_2)_5-$ | | $(CH_3)_3C-CH_2-$ | |
| 635 | Cl | Cl | H | $-(CH_2)_5-$ | | 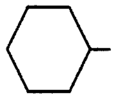 | |
| 636 | Cl | Cl | H | $-(CH_2)_5-$ | | 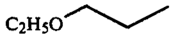 | |
| 637 | Cl | Cl | H | $-(CH_2)_5-$ | | 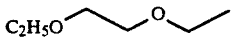 | |
| 638 | Cl | Cl | H | $-(CH_2)_5-$ | | 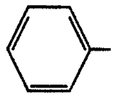 | |
| 639 | Cl | Cl | H | $-(CH_2)_5-$ | | 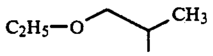 | |
| 640 | Cl | Cl | H | $-(CH_2)_5-$ | | 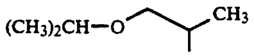 | |
| 641 | Cl | Cl | H | $-(CH_2)_5-$ | | 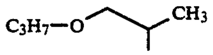 | |
| 642 | Cl | Cl | H | $-(CH_2)_5-$ | | 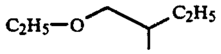 | |
| 643 | Cl | Cl | 6-Cl | H | H | $CH_3$ | |
| 644 | Cl | Cl | 6-Cl | $CH_3$ | H | $CH_3$ | |
| 645 | Cl | Cl | 6-Cl | $CH_3$ | H | $CH(CH_3)_2$ | |
| 646 | Cl | Cl | 6-Cl | $CH_3$ | H | $CH_2C(CH_3)_3$ | |
| 647 | $CH_3$ | $CH_3$ | H | H | H | $CH_3$ | |
| 648 | $CH_3$ | $CH_3$ | H | $CH_3$ | H | $CH_3$ | |
| 649 | $CH_3$ | $CH_3$ | H | $CH_3$ | H | $CH(CH_3)_2$ | |
| 650 | $CH_3$ | $CH_3$ | H | $CH_3$ | H | $CH_2C(CH_3)_3$ | |
| 651 | $CH_3$ | $CH_3$ | 6-$CH_3$ | H | H | $CH_3$ | |
| 652 | $CH_3$ | $CH_3$ | 6-$CH_3$ | H | H | $C_2H_5$ | |
| 653 | $CH_3$ | $CH_3$ | 6-$CH_3$ | H | H | $CH(CH_3)_2$ | |

TABLE 3-continued

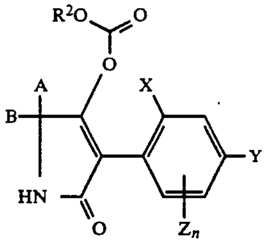

(Ic)

| Ex.-No. | X | Y | $Z_n$ | A | B | $R^2$ | Mp °C. |
|---|---|---|---|---|---|---|---|
| 654 | $CH_3$ | $CH_3$ | 6-$CH_3$ | H | H | 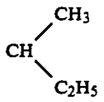 | |
| 655 | $CH_3$ | $CH_3$ | 6-$CH_3$ | H | H | $CH_2—C(CH_3)_3$ | |
| 656 | $CH_3$ | CH | 6-$CH_3$ | H | H | $(CH_2)_2O—C_2H_5$ | |
| 657 | $CH_3$ | $CH_3$ | 6-$CH_3$ | H | H | 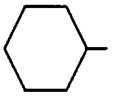 | |
| 658 | $CH_3$ | $CH_3$ | 6-$CH_3$ | H | H | 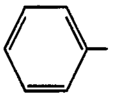 | |
| 659 | $CH_3$ | $CH_3$ | 6-$CH_3$ | $CH_3$ | H | $CH_3$ | |
| 660 | $CH_3$ | $CH_3$ | 6-$CH_3$ | $CH_3$ | H | $C_2H_5$ | |
| 661 | $CH_3$ | $CH_3$ | 6-$CH_3$ | $CH_3$ | H | $CH(CH_3)_2$ | |
| 662 | $CH_3$ | $CH_3$ | 6-$CH_3$ | $CH_3$ | H | 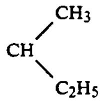 | |
| 663 | $CH_3$ | $CH_3$ | 6-$CH_3$ | $CH_3$ | H | $CH_2C(CH_3)_3$ | |
| 664 | $CH_3$ | $CH_3$ | 6-$CH_3$ | $CH_3$ | H | $(CH_2)_2O—C_2H_5$ | |
| 665 | $CH_3$ | $CH_3$ | 6-$CH_3$ | $CH_3$ | H | 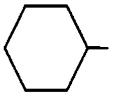 | |
| 666 | $CH_3$ | $CH_3$ | 6-$CH_3$ | $CH_3$ | H | 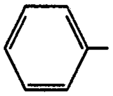 | |
| 667 | $CH_3$ | $CH_3$ | 6-$CH_3$ | $CH(CH_3)_2$ | H | $CH_3$ | |
| 668 | $CH_3$ | $CH_3$ | 6-$CH_3$ | $CH(CH_3)_2$ | H | $C_2H_5$ | |
| 669 | $CH_3$ | $CH_3$ | 6-$CH_3$ | $CH(CH_3)_2$ | H | $CH(CH_3)_2$ | |
| 670 | $CH_3$ | $CH_3$ | 6-$CH_3$ | $CH(CH_3)_2$ | H | 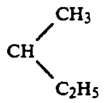 | |
| 671 | $CH_3$ | $CH_3$ | 6-$CH_3$ | $CH(CH_3)_2$ | H | $CH_2C(CH_3)_3$ | |
| 672 | $CH_3$ | $CH_3$ | 6-$CH_3$ | $CH(CH_3)_2$ | H | $(CH_2)_2O—C_2H_5$ | |
| 673 | $CH_3$ | $CH_3$ | 6-$CH_3$ | $CH(CH_3)_2$ | H | 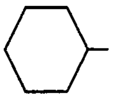 | |

TABLE 3-continued

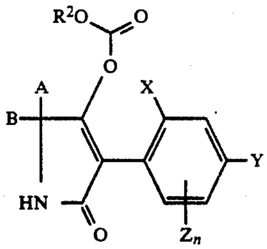

(Ic)

| Ex.-No. | X | Y | $Z_n$ | A | B | $R^2$ | Mp °C. |
|---|---|---|---|---|---|---|---|
| 674 | $CH_3$ | $CH_3$ | 6-$CH_3$ | $CH(CH)_2$ | H | 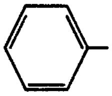 | |
| 675 | $CH_3$ | $CH_3$ | 6-$CH_3$ | $CH_2CH(CH_3)_2$ | H | $CH_3$ | |
| 676 | $CH_3$ | $CH_3$ | 6-$CH_3$ | $CH_2CH(CH_3)_2$ | H | $C_2H_5$ | |
| 677 | $CH_3$ | $CH_3$ | 6-$CH_3$ | $CH_2CH(CH_3)_2$ | H | $CH(CH_3)_2$ | |
| 678 | $CH_3$ | $CH_3$ | 6-$CH_3$ | $CH_2CH(CH_3)_2$ | H | $CH_2CH(CH_3)_2$ | |
| 679 | $CH_3$ | $CH_3$ | 6-$CH_3$ | $CH_2CH(CH_3)_2$ | H | 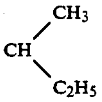 | |
| 680 | $CH_3$ | $CH_3$ | 6-$CH_3$ | $CH_2CH(CH_3)_2$ | H | $CH_2C(CH_3)_3$ | |
| 681 | $CH_3$ | $CH_3$ | 6-$CH_3$ | $CH_2CH(CH_3)_2$ | H | $(CH_2)_2O-C_2H_5$ | |
| 682 | $CH_3$ | $CH_3$ | 6-$CH_3$ | $CH_2CH(CH_3)_2$ | H | 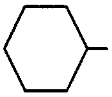 | |
| 683 | $CH_3$ | $CH_3$ | 6-$CH_3$ | $CH_2CH(CH_3)_2$ | H | 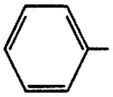 | |
| 684 | $CH_3$ | $CH_3$ | 6-$CH_3$ | $(CH_2)_2-SCH_3$ | H | $CH_3$ | |
| 685 | $CH_3$ | $CH_3$ | 6-$CH_3$ | $(CH_2)_2-SCH_3$ | H | $C_2H_5$ | |
| 686 | $CH_3$ | $CH_3$ | 6-$CH_3$ | $(CH_2)_2-SCH_3$ | H | $CH(CH_3)_2$ | |
| 687 | $CH_3$ | $CH_3$ | 6-$CH_3$ | $(CH_2)_2-SCH_3$ | H | 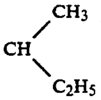 | |
| 688 | $CH_3$ | $CH_3$ | 6-$CH_3$ | $(CH_2)_2-SCH_3$ | H | $CH_2C(CH_3)_3$ | |
| 689 | $CH_3$ | $CH_3$ | 6-$CH_3$ | $(CH_2)_2-SCH_3$ | H | $(CH_2)_2O-C_2H_5$ | |
| 690 | $CH_3$ | $CH_3$ | 6-$CH_3$ | $(CH_2)_2-SCH_3$ | H | 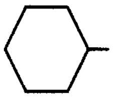 | |
| 691 | $CH_3$ | $CH_3$ | 6-$CH_3$ | $(CH_2)_2-SCH_3$ | H | 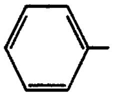 | |
| 692 | $CH_3$ | H | 6-$CH_3$ | $CH_3$ | $CH_3$ | $CH_3$ | |
| 693 | $CH_3$ | $CH_3$ | 6-$CH_3$ | $CH_3$ | $CH_3$ | $C_2H_5$ | 140 |
| 694 | $CH_3$ | $CH_3$ | 6-$CH_3$ | $CH_3$ | $CH_3$ | $(CH_3)_2CH-$ | 161-163 |
| 695 | $CH_3$ | $CH_3$ | 6-$CH_3$ | $CH_3$ | $CH_3$ | $(CH_3)_2CH-CH_2-$ | |
| 696 | $CH_3$ | $CH_3$ | 6-$CH_3$ | $CH_3$ | $CH_3$ | 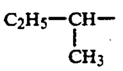 | 98 |
| 697 | $CH_3$ | $CH_3$ | 6-$CH_3$ | $CH_3$ | $CH_3$ | $(CH_3)_3C-$ | |
| 698 | $CH_3$ | $CH_3$ | 6-$CH_3$ | $CH_3$ | $CH_3$ | $(CH_3)_3C-CH_2-$ | |

TABLE 3-continued

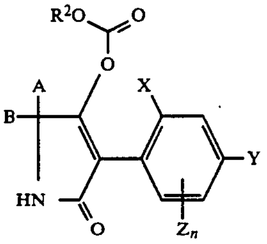

(Ic)

| Ex.-No. | X | Y | $Z_n$ | A | B | $R^2$ | Mp °C. |
|---|---|---|---|---|---|---|---|
| 699 | $CH_3$ | $CH_3$ | 6-$CH_3$ | $CH_3$ | $CH_3$ | 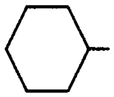 | |
| 700 | $CH_3$ | $CH_3$ | 6-$CH_3$ | $CH_3$ | $CH_3$ | 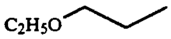 | |
| 701 | $CH_3$ | $CH_3$ | 6-$CH_3$ | $CH_3$ | $CH_3$ | 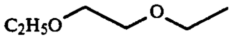 | |
| 702 | $CH_3$ | $CH_3$ | 6-$CH_3$ | $CH_3$ | $CH_3$ | 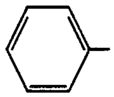 | |
| 703 | $CH_3$ | $CH_3$ | 6-$CH_3$ | $CH_3$ | $CH_3$ | 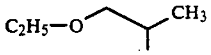 | |
| 704 | $CH_3$ | $CH_3$ | 6-$CH_3$ | $CH_3$ | $CH_3$ | 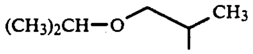 | |
| 705 | $CH_3$ | $CH_3$ | 6-$CH_3$ | $CH_3$ | $CH_3$ | 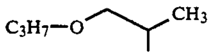 | |
| 706 | $CH_3$ | $CH_3$ | 6-$CH_3$ | $CH_3$ | $CH_3$ | 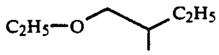 | |
| 707 | $CH_3$ | H | 6-$CH_3$ | $C_2H_5$ | $CH_3$ | $CH_3$ | |
| 708 | $CH_3$ | $CH_3$ | 6-$CH_3$ | $C_2H_5$ | $CH_3$ | $C_2H_5$ | |
| 709 | $CH_3$ | $CH_3$ | 6-$CH_3$ | $C_2H_5$ | $CH_3$ | $(CH_3)_2CH-$ | |
| 710 | $CH_3$ | $CH_3$ | 6-$CH_3$ | $C_2H_5$ | $CH_3$ | $(CH_3)_2CH-CH_2-$ | |
| 711 | $CH_3$ | $CH_3$ | 6-$CH_3$ | $C_2H_5$ | $CH_3$ | $C_2H_5-\underset{\underset{\displaystyle CH_3}{\vert}}{CH}-$ | |
| 712 | $CH_3$ | $CH_3$ | 6-$CH_3$ | $C_2H_5$ | $CH_3$ | $(CH_3)_3C-$ | |
| 713 | $CH_3$ | $CH_3$ | 6-$CH_3$ | $C_2H_5$ | $CH_3$ | $(CH_3)_3C-CH_2-$ | |
| 714 | $CH_3$ | $CH_3$ | 6-$CH_3$ | $C_2H_5$ | $CH_3$ | 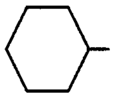 | |
| 715 | $CH_3$ | $CH_3$ | 6-$CH_3$ | $C_2H_5$ | $CH_3$ | 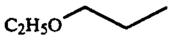 | |
| 716 | $CH_3$ | $CH_3$ | 6-$CH_3$ | $C_2H_5$ | $CH_3$ | 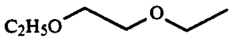 | |
| 717 | $CH_3$ | $CH_3$ | 6-$CH_3$ | $C_2H_5$ | $CH_3$ | 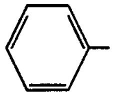 | |

TABLE 3-continued

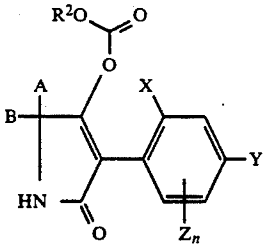

(Ic)

| Ex.-No. | X | Y | $Z_n$ | A | B | $R^2$ | Mp °C. |
|---|---|---|---|---|---|---|---|
| 718 | $CH_3$ | $CH_3$ | 6-$CH_3$ | $C_2H_5$ | $CH_3$ | 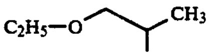 | |
| 719 | $CH_3$ | $CH_3$ | 6-$CH_3$ | $C_2H_5$ | $CH_3$ | 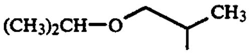 | |
| 720 | $CH_3$ | $CH_3$ | 6-$CH_3$ | $C_2H_5$ | $CH_3$ | 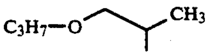 | |
| 721 | $CH_3$ | $CH_3$ | 6-$CH_3$ | $C_2H_5$ | $CH_3$ | 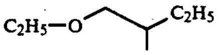 | |
| 722 | $CH_3$ | H | 6-$CH_3$ | $C_2H_5$ | $C_2H_5$ | $CH_3$ | |
| 723 | $CH_3$ | $CH_3$ | 6-$CH_3$ | $C_2H_5$ | $C_2H_5$ | $C_2H_5$ | |
| 724 | $CH_3$ | $CH_3$ | 6-$CH_3$ | $C_2H_5$ | $C_2H_5$ | $(CH_3)_2CH-$ | |
| 725 | $CH_3$ | $CH_3$ | 6-$CH_3$ | $C_2H_5$ | $C_2H_5$ | $(CH_3)_2CH-CH_2-$ | |
| 726 | $CH_3$ | $CH_3$ | 6-$CH_3$ | $C_2H_5$ | $C_2H_5$ | $C_2H_5-CH-$<br>$CH_3$ | |
| 727 | $CH_3$ | $CH_3$ | 6-$CH_3$ | $C_2H_5$ | $C_2H_5$ | $(CH_3)_3C-$ | |
| 728 | $CH_3$ | $CH_3$ | 6-$CH_3$ | $C_2H_5$ | $C_2H_5$ | $(CH_3)_3C-CH_2-$ | |
| 729 | $CH_3$ | $CH_3$ | 6-$CH_3$ | $C_2H_5$ | $C_2H_5$ | 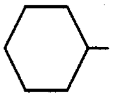 | |
| 730 | $CH_3$ | $CH_3$ | 6-$CH_3$ | $C_2H_5$ | $C_2H_5$ | 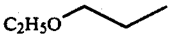 | |
| 731 | $CH_3$ | $CH_3$ | 6-$CH_3$ | $C_2H_5$ | $C_2H_5$ | 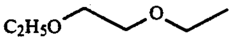 | |
| 732 | $CH_3$ | $CH_3$ | 6-$CH_3$ | $C_2H_5$ | $C_2H_5$ | 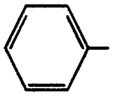 | |
| 733 | $CH_3$ | $CH_3$ | 6-$CH_3$ | $C_2H_5$ | $C_2H_5$ | 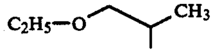 | |
| 734 | $CH_3$ | $CH_3$ | 6-$CH_3$ | $C_2H_5$ | $C_2H_5$ | 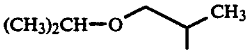 | |
| 735 | $CH_3$ | $CH_3$ | 6-$CH_3$ | $C_2H_5$ | $C_2H_5$ | 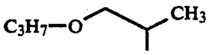 | |
| 736 | $CH_3$ | $CH_3$ | 6-$CH_3$ | $C_2H_5$ | $C_2H_5$ | 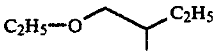 | |
| 737 | $CH_3$ | H | 6-$CH_3$ | $C_3H_7$ | $CH_3$ | $CH_3$ | |
| 738 | $CH_3$ | $CH_3$ | 6-$CH_3$ | $C_3H_7$ | $CH_3$ | $C_2H_5$ | |
| 739 | $CH_3$ | $CH_3$ | 6-$CH_3$ | $C_3H_7$ | $CH_3$ | $(CH_3)_2CH-$ | |
| 740 | $CH_3$ | $CH_3$ | 6-$CH_3$ | $C_3H_7$ | $CH_3$ | $(CH_3)_2CH-CH_2-$ | |

TABLE 3-continued (Ic)

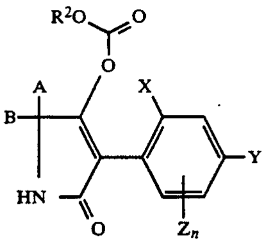

| Ex.-No. | X | Y | $Z_n$ | A | B | $R^2$ | Mp °C. |
|---|---|---|---|---|---|---|---|
| 741 | $CH_3$ | $CH_3$ | 6-$CH_3$ | $C_3H_7$ | $CH_3$ | $C_2H_5$—CH—<br>$CH_3$ | |
| 742 | $CH_3$ | $CH_3$ | 6-$CH_3$ | $C_3H_7$ | $CH_3$ | $(CH_3)_3C$— | |
| 743 | $CH_3$ | $CH_3$ | 6-$CH_3$ | $C_3H_7$ | $CH_3$ | $(CH_3)_3C$—$CH_2$— | |
| 744 | $CH_3$ | $CH_3$ | 6-$CH_3$ | $C_3H_7$ | $CH_3$ | 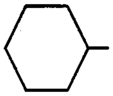 | |
| 745 | $CH_3$ | $CH_3$ | 6-$CH_3$ | $C_3H_7$ | $C_2H_5$ | 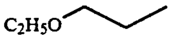 | |
| 746 | $CH_3$ | $CH_3$ | 6-$CH_3$ | $C_3H_7$ | $CH_3$ | 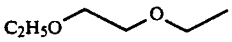 | |
| 747 | $CH_3$ | $CH_3$ | 6-$CH_3$ | $C_3H_7$ | $CH_3$ | 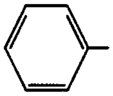 | |
| 748 | $CH_3$ | $CH_3$ | 6-$CH_3$ | $C_3H_7$ | $CH_3$ | 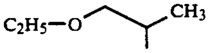 | |
| 749 | $CH_3$ | $CH_3$ | 6-$CH_3$ | $C_3H_7$ | $CH_3$ | 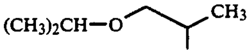 | |
| 750 | $CH_3$ | $CH_3$ | 6-$CH_3$ | $C_3H_7$ | $CH_3$ | 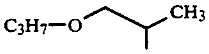 | |
| 751 | $CH_3$ | $CH_3$ | 6-$CH_3$ | $C_3H_7$ | $CH_3$ | 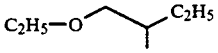 | |
| 752 | $CH_3$ | H | 6-$CH_3$ | i-$C_3H_7$ | $CH_3$ | $CH_3$ | |
| 753 | $CH_3$ | $CH_3$ | 6-$CH_3$ | i-$C_3H_7$ | $CH_3$ | $C_2H_5$ | |
| 754 | $CH_3$ | $CH_3$ | 6-$CH_3$ | i-$C_3H_7$ | $CH_3$ | $(CH_3)_2CH$— | |
| 755 | $CH_3$ | $CH_3$ | 6-$CH_3$ | i-$C_3H_7$ | $CH_3$ | $(CH_3)_2CH$—$CH_2$— | |
| 756 | $CH_3$ | $CH_3$ | 6-$CH_3$ | i-$C_3H_7$ | $CH_3$ | $C_2H_5$—CH—<br>$CH_3$ | |
| 757 | $CH_3$ | $CH_3$ | 6-$CH_3$ | i-$C_3H_7$ | $CH_3$ | $(CH_3)_3C$— | |
| 758 | $CH_3$ | $CH_3$ | 6-$CH_3$ | i-$C_3H_7$ | $CH_3$ | $(CH_3)_3C$—$CH_2$— | |
| 759 | $CH_3$ | $CH_3$ | 6-$CH_3$ | i-$C_3H_7$ | $CH_3$ | 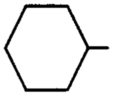 | |
| 760 | $CH_3$ | $CH_3$ | 6-$CH_3$ | i-$C_3H_7$ | $CH_3$ | 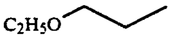 | |
| 761 | $CH_3$ | $CH_3$ | 6-$CH_3$ | i-$C_3H_7$ | $CH_3$ | 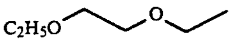 | |

TABLE 3-continued

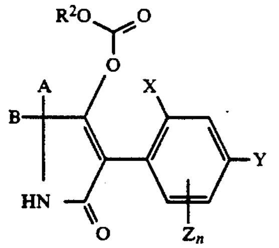

(Ic)

| Ex.-No. | X | Y | $Z_n$ | A | B | $R^2$ | Mp °C. |
|---|---|---|---|---|---|---|---|
| 762 | $CH_3$ | $CH_3$ | 6-$CH_3$ | i-$C_3H_7$ | $CH_3$ | 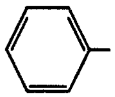 | |
| 763 | $CH_3$ | $CH_3$ | 6-$CH_3$ | i-$C_3H_7$ | $CH_3$ | 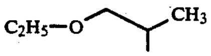 | |
| 764 | $CH_3$ | $CH_3$ | 6-$CH_3$ | i-$C_3H_7$ | $CH_3$ | 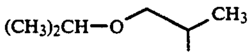 | |
| 765 | $CH_3$ | $CH_3$ | 6-$CH_3$ | i-$C_3H_7$ | $CH_3$ | 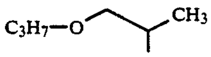 | |
| 766 | $CH_3$ | $CH_3$ | 6-$CH_3$ | i-$C_3H_7$ | $CH_3$ | 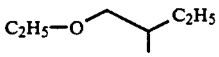 | |
| 767 | $CH_3$ | H | 6-$CH_3$ | $-(CH_2)_4-$ | | $CH_3$ | |
| 768 | $CH_3$ | $CH_3$ | 6-$CH_3$ | $-(CH_2)_4-$ | | $C_2H_5$ | |
| 769 | $CH_3$ | $CH_3$ | 6-$CH_3$ | $-(CH_2)_4-$ | | $(CH_3)_2CH-$ | |
| 770 | $CH_3$ | $CH_3$ | 6-$CH_3$ | $-(CH_2)_4-$ | | $(CH_3)_2CH-CH_2-$ | |
| 771 | $CH_3$ | $CH_3$ | 6-$CH_3$ | $-(CH_2)_4-$ | | $C_2H_5-CH(CH_3)-$ | |
| 772 | $CH_3$ | $CH_3$ | 6-$CH_3$ | $-(CH_2)_4-$ | | $(CH_3)_3C-$ | |
| 773 | $CH_3$ | $CH_3$ | 6-$CH_3$ | $-(CH_2)_4-$ | | $(CH_3)_3C-CH_2-$ | |
| 774 | $CH_3$ | $CH_3$ | 6-$CH_3$ | $-(CH_2)_4-$ | | 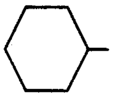 | |
| 775 | $CH_3$ | $CH_3$ | 6-$CH_3$ | $-(CH_2)_4-$ | | 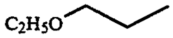 | |
| 776 | $CH_3$ | $CH_3$ | 6-$CH_3$ | $-(CH_2)_4-$ | | 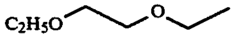 | |
| 777 | $CH_3$ | $CH_3$ | 6-$CH_3$ | $-(CH_2)_4-$ | | 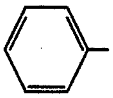 | |
| 778 | $CH_3$ | $CH_3$ | 6-$CH_3$ | $-(CH_2)_4-$ | | 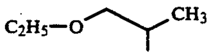 | |
| 779 | $CH_3$ | $CH_3$ | 6-$CH_3$ | $-(CH_2)_4-$ | | 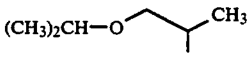 | |
| 780 | $CH_3$ | $CH_3$ | 6-$CH_3$ | $-(CH_2)_4-$ | | 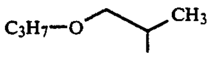 | |
| 781 | $CH_3$ | $CH_3$ | 6-$CH_3$ | $-(CH_2)_4-$ | | 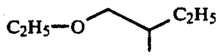 | |

TABLE 3-continued (Ic)

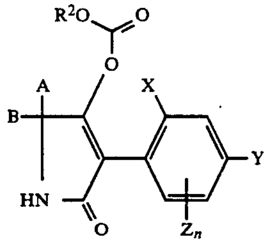

| Ex.-No. | X | Y | $Z_n$ | A | B | $R^2$ | Mp °C. |
|---|---|---|---|---|---|---|---|
| 782 | $CH_3$ | H | 6-$CH_3$ | $-(CH_2)_5-$ | | $CH_3$ | |
| 783 | $CH_3$ | $CH_3$ | 6-$CH_3$ | $-(CH_2)_5-$ | | $C_2H_5$ | |
| 784 | $CH_3$ | $CH_3$ | 6-$CH_3$ | $-(CH_2)_5-$ | | $(CH_3)_2CH-$ | |
| 785 | $CH_3$ | $CH_3$ | 6-$CH_3$ | $-(CH_2)_5-$ | | $(CH_3)_2CH-CH_2-$ | |
| 786 | $CH_3$ | $CH_3$ | 6-$CH_3$ | $-(CH_2)_5-$ | | $C_2H_5-CH(CH_3)-$ | |
| 787 | $CH_3$ | $CH_3$ | 6-$CH_3$ | $-(CH_2)_5-$ | | $(CH_3)_3C-$ | |
| 788 | $CH_3$ | $CH_3$ | 6-$CH_3$ | $-(CH_2)_5-$ | | $(CH_3)_3C-CH_2-$ | |
| 789 | $CH_3$ | $CH_3$ | 6-$CH_3$ | $-(CH_2)_5-$ | | 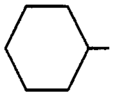 | |
| 790 | $CH_3$ | $CH_3$ | 6-$CH_3$ | $-(CH_2)_5-$ | | 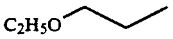 | |
| 791 | $CH_3$ | $CH_3$ | 6-$CH_3$ | $-(CH_2)_5-$ | | 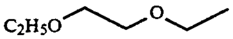 | |
| 792 | $CH_3$ | $CH_3$ | 6-$CH_3$ | $-(CH_2)_5-$ | | 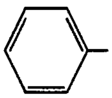 | |
| 793 | $CH_3$ | $CH_3$ | 6-$CH_3$ | $-(CH_2)_5-$ | | 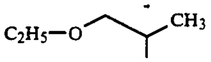 | |
| 794 | $CH_3$ | $CH_3$ | 6-$CH_3$ | $-(CH_2)_5-$ | | 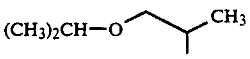 | |
| 795 | $CH_3$ | $CH_3$ | 6-$CH_3$ | $-(CH_2)_5-$ | | 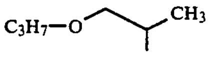 | |
| 796 | $CH_3$ | $CH_3$ | 6-$CH_3$ | $-(CH_2)_5-$ | | 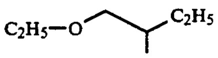 | |

Example (II1)

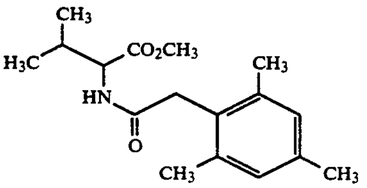

138 g (0.5 mol) of N-(2,4,6-trimethylphenyl-acetyl)-valine are suspended in 500 ml of methanol, 73 ml (0.55 mol) of dimethoxypropane are added, 4.75 g (25 mmol) of p-toluenesulphonic acid monohydrate are added, and the mixture is then refluxed while thin-layer chromatography (TLC) checks are carried out.

After the solvent has been removed by evaporation on the rotary evaporator, the residue is taken up in methylene chloride, and the mixture is washed with sodium hydrogen carbonate solution, dried and evaporated on a rotary evaporator.

Yield: 127.6 g (=88% of theory).

Example (IIa1)

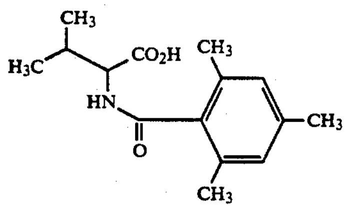

10 g (0.25 mol) of NaOH tablets are added to 58.8 g (0.5 mol) of L-valine in 720 ml of water. Thereafter, 30 g (0.75 mol) of NaOH tablets in 150 ml of water and 98.2 g (0.5 mol) of mesityleneacetyl chloride are synchronously added dropwise in such a way that the temperature, does not exceed 40° C. After 1 h, the mixture is acidified with concentrated hydrochloric acid at 0°-20° C., the product is filtered off with suction and dried in vacuo at 70° C. over diphosphorus pentoxide.

Yield: 138 g (=100% of theory) m.p. 140° C.

The active compounds of the formula (I) according to the invention are suitable for combating animal pests, in particular of the class of the Arachnida and the order of the mites (Acarina) which occur in agriculture, in forestry, in the protection of stored goods and materials, and in the hygiene field, these active substances being well tolerated by plants and having a favourable toxicity towards warm-blooded species. They are active against normally sensitive and resistant species and against all or some stages of development. The abovementioned pests include:

From the order of the Acarina, for example *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp..

The active substances according to the invention are not only active against pests of plants, the hygiene field and of stored goods, but also in the veterinary medicine sector against parasites of animals (ectoparasites) such as scaly ticks, argasidae, scab mites and trombedae.

They are active against normally-sensitive and resistant species and strains and against all parasitizing and non-parasitizing development stages of the ectoparasites.

The active substances according to the invention are distinguished by a high acaricidal activity. They can be employed with particularly good success against mites which are injurious to plants, such as, for example, against the common spider mite (*Tetranychus urticae*).

The active compounds according to the invention can furthermore be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

It is characteristic of the compounds according to the invention that they have a selective activity against monocotyledon weeds when used pre- and post-emergence, while being well tolerated by crop plants.

The active compounds according to the invention can be used, for example, in connection with the following plants:

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In this context, the active compounds according to the invention show, besides an outstanding action against harmful plants, a good tolerance by important crop plants such as, for example wheat, cotton, soya beans, citrus fruit and sugar beet, and they can therefore be employed as selective weed killers.

The active compounds can be converted into the customary formulations, such as solutions, emulsions, suspensions, powders, foams, pastes, granules, aerosols, natural and synthetic substances impregnated with active compounds, very fine capsules in polymeric substances and in coating compositions for seed, furthermore in formulation with burning equipment such as fumigating cartridges, fumigating cans, fumigating coils and the like, as well as ULV cold-mist and warm-mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at room temperature and atmospheric pressure, for example aerosol propellants, such as halogenohydrocarbons and also butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms prepared from these formulations as a mixture with other active substances such as insecticides, attractants, sterilants, acaricides, nematicides, herbicides or fungicides. The insecticides include, for example, phosphates, carbamates, carboxylic esters, chlorinated hydrocarbons, phenylureas, substances produced by microorganisms, etc.

Furthermore, the active substances according to the invention can be present in their commercially available formulations and in the use forms prepared from these formulations as a mixture with synergists. Synergists are compounds by which the action of the active substances is increased without it being necessary for the synergist added to be active itself.

The active compound content of the use forms prepared from the commercially available formulations can vary within wide limits. The active compound concentration of the use forms can be from 0.0000001 to 95% by weight of active substance, preferably between 0.0001 and 1% by weight.

The compounds are employed in a customary manner appropriate for the use forms.

The active substances according to the invention are also suitable for combating mites, ticks, etc. in the sectors of animal keeping and cattle breeding; better results, for example higher milk production, greater weight, more attractive animal pelt, longer life, etc., can be achieved by combating the pests.

The application of the active compounds according to the invention occurs in this sector in a known fashion, such as by oral application in the form of, for example, tablets, capsules, potions, granules, by means of dermal or external application in the form of, for example, dipping, spraying, pouring-on, spotting on and dusting, as well as by means of parenteral application in the form of, for example, injection and, furthermore, by means of the feed-through process. In addition, application as moulded articles (collar, ear tag) is also possible.

In the biological examples listed below, the following compounds were used as comparison substances:

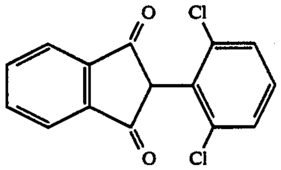
A)

disclosed in DE-A 2,361,084 and U.S. Pat. No. 4,632,698

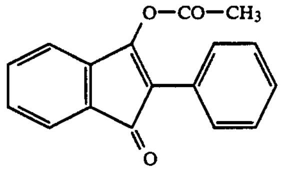
B)

disclosed in DE-A 2,361,084 and U.S. Pat. No. 4,632,698

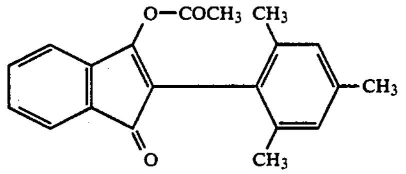
C)

disclosed in DE-A 2,361,084 and U.S. Pat. No. 4,632,698

Example A

Phaedon larvae test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), while the leaves are still moist.

After the desired time, the destruction in % is determined. 100% means that all the beetle larvae have been killed; 0% means that none of the beetle larvae have been killed.

In this test, a superior activity compared with the prior art is shown, for example, by the following compounds of the Preparation Examples: (1), (2), (32), (40), (278), (280), (290), (299).

Example B

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the desired time, the destruction in % is determined. 100% means that all the caterpillars have been killed; 0% means that none of the caterpillars have been killed.

In this test, a superior activity compared with the prior art is shown, for example, by the following compounds of the Preparation Examples: (1), (32), (283), (299).

Example C

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice leaf-hopper (*Nephotettix cincticepa*) while the seedlings are still moist.

After the desired time, the destruction in % is determined. 100% means that all the leaf-hoppers have been killed; 0% means that none of the leaf-hoppers have been killed.

In this test, a superior activity compared with the prior art is shown, for example, by the following compounds of the Preparation Examples: (1), (32), (43), (290), (292), (299), (301).

Example D

Pre-emergence test

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Seeds of the test plants are sown in standard soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, a superior activity compared with the prior art is shown, for example, by the following compounds of the Preparation Examples: (32), (281), (283).

Example E

Post-emergence test

Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, a superior activity compound with the prior art is shown, for example, by the following compounds of the Preparation Examples: (32), (281), (283).

Example F

Tetranychus test (OP resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water containing emulsifier to the desired concentration.

Bean plants (*Phaseolus vulgaris*) which are heavily infested with all development stages of the common spider mite or greenhouse red spider mite (*Tetranychus urticae*) are sprayed with an active compound preparation of the desired concentration until dripping wet.

After the desired time, the action in % is determined. 100% means that all the spider mites have been killed; 0% means that none of the spider mites have been killed.

In this test, a superior activity compared with the prior art is shown, for example, by the following compounds of the Preparation Examples: (281), (283).

It is understood that the specification and examples are illustrative but not limitative of the present invention and that other embodiments within the spirit and scope of the invention will suggest themselves to those skilled in the art.

We claim:

1. A 3-aryl-pyrrolidine-2,4-dione derivative of the formula

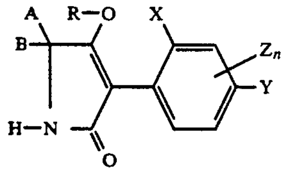

(I)

in which

X represents $C_1$–$C_6$-alkyl, halogen or $C_1$–$C_6$-alkoxy,

Y represent hydrogen, $C_1$–$C_6$-alkyl, halogen or $C_1$–$C_6$-alkoxy or $C_1$–$C_3$-halogenoalkyl, Z represents $C_1$–$C_6$-alkyl, halogen or $C_1$–$C_6$-alkoxy, n represents a number from 0–3, R represents hydrogen (Ia), or represents the groups of the formula —CO—$R^1$ or (Ib)

—CO—O—$R^2$ or (Ic)

$E^{\oplus}$ (Id)

in which $R^1$ represents $C_1$–$C_{20}$-alkyl, $C_2$–$C_{20}$-alkenyl, $C_1$–$C_8$-alkoxy-$C_2$–$C_8$-alkyl, $C_1$–$C_8$-alkylthio-$C_2$–$C_8$-alkyl, $C_1$–$C_8$-polyalkoxy-$C_2$–$C_8$-alkyl and cycloalkyl which has 3–8 ring atoms and which can be interrupted by at least one of oxygen and sulphur, each of these substituents being optionally substituted by halogen, or represents optionally halogen-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl; or represents optionally halogen-, $C_1$–$C_6$-alkyl-, $C_1$–$C_6$-alkoxy-, $C_1$–$C_6$-halogenoalkyl- or represents optionally halogen- and $C_1$–$C_6$-alkyl-substituted phenoxy-$C_1$–$C_6$-alkyl, $R^2$ represents $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl each of which is optionally substituted by halogen, or represents phenyl or cycloalkyl which has 3–8 ring atoms, each of which is optionally substituted by halogen-, nitro-, $C_1$–$C_6$-alkyl-, $C_1$–$C_6$-alkoxy- or $C_1$–$C_6$-halogenoalkyl, A represents hydrogen or represents straight-chain or branched $C_1$–$C_{12}$-alkyl, $C_3$–$C_8$-alkenyl, $C_3$–$C_8$-alkynyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$-alkylthio-$C_2$–$C_8$-alkyl, cycloalkyl which has 3–8 ring atoms and which can be interrupted by at least one of oxygen and sulphur, each of these substituents being optionally substituted by halogen, or represents aryl, or aryl-$C_1$–$C_6$-alkyl each of which is optionally substituted by halogen, $C_1$–$C_6$-alkyl-$C_1$–$C_6$-halogenoalkyl-, $C_1$–$C_6$-alkoxy or nitro, B represents hydrogen or straight-chain or branched $C_1$–$C_{12}$-alkyl or $C_1$–$C_8$-alkoxyalkyl, and $E^{\oplus}$ represents a metal ion equivalent or an ammonium ion.

2. A 3-aryl-pyrrolidine-2,4-dione derivative according to claim 1, in which

X represents $C_1$–$C_4$-alkyl, halogen, or $C_1$–$C_4$-alkoxy,

Y represents hydrogen, $C_1$–$C_6$-alkyl, halogen, $C_1$–$C_4$-alkoxy or $C_1$–$C_2$-halogenoalkyl, Z represents $C_1$–$C_4$-alkyl, halogen or $C_1$–$C_4$-alkoxy, n represents a number from 0–3, R represents hydrogen (Ia) or represents the groups of the formula —CO—$R^1$ (Ib), or —CO—O—$R^2$ (Ic) or $E^{\oplus}$ (Id)

in which $R^1$ represents $C_1$–$C_{16}$-alkyl, $C_2$–$C_{16}$-alkenyl, $C_1$–$C_6$-alkoxy-$C_2$–$C_6$-alkyl, $C_1$–$C_6$-alkylthio-$C_2$–$C_6$-alkyl, $C_1$–$C_6$-polyalkoxy-$C_2$–$C_6$-alkyl and cycloalkyl which has 3–7 ring atoms and which can be interrupted once or twice by at least one of oxygen and sulphur atoms, each of these substituents being optionally substituted by halogen, or represents optionally halogen-, nitro-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl, or represents optionally halogen-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, optionally represents halogen- and $C_1$–$C_4$-alkyl-substituted phenoxy-$C_1$–$C_5$-alkyl, $R^2$ represents $C_1$–$C_{16}$-alkyl, $C_2$–$C_{16}$-alkenyl, $C_1$–$C_{16}$-alkoxy-$C_2$–$C_6$-alkyl or $C_1$–$C_8$-polyalkoxy-$C_2$–$C_6$-alkyl each of which is optionally substituted by halogen, or represents optionally halogen, nitro-, $C_1$–$C_4$-alkyl, $C_1$–$C_3$-alkoxy- or $C_1$–$C_3$-halogenoalkyl-substituted phenyl, A represents hydrogen or straight-chain or branched $C_1$–$C_{10}$-alkyl, $C_3$–$C_6$-alkenyl, $C_3$–$C_6$-alkynyl, $C_1$–$C_8$-alkoxy-$C_2$–$C_6$-alkyl, $C_1$–$C_6$-polyalkoxy-$C_2$–$C_6$-alkyl, $C_1$–$C_8$alkylthio-$C_2$–$C_6$-alkyl, cycloalkyl which has 3–7 ring atoms and which can be interrupted once or twice by at least one of oxygen and sulphur atoms, each of these substituents being optionally substituted by halogen, or represents aryl, or aryl-$C_1$–$C_4$-alkyl each of which is optionally substituted by halogen-, $C_1$–$C_4$-alkyl-, $C_1$–$C_4$-halogenoalkyl, $C_1$–$C_4$-alkoxy or nitro, B represents hydrogen or straight-chain or branched $C_1$–$C_{10}$-alkyl or $C_1$–C alkoxyalkyl, and $E^{\oplus}$ represents a metal ion equivalent or an ammonium ion.

3. A 3-aryl-pyrrolidine-2,4-dione derivative according to claim 1, in which

X represents methyl, ethyl, propyl, i-propyl, fluorine, chlorine, bromine, methoxy and ethoxy, Y represents hydrogen, methyl, ethyl, propyl, i-propyl, butyl, i-butyl, tert.-butyl, fluorine, chlorine, bromine, methoxy, ethoxy and trifluoromethyl, Z represents methyl, ethyl, i-propyl, butyl, i-butyl, tert.-butyl, fluorine, chlorine, bromine, methoxy and ethoxy, n represents a number from 0–3, R represents hydrogen (Ia) or represents the groups of the formula —CO—$R^1$ (Ib) or —CO—O—$R^2$ (Ic) or $E^{\oplus}$ (Id)

in which $R^1$ represents $C_1$–$C_{14}$-alkyl, $C_2$–$C_{14}$-alkenyl, $C_1$–$C_4$-alkoxy-$C_2$–$C_6$-alkyl, $C_1$–$C_4$-alkylthio-$C_2$–$C_6$-alkyl, $C_1$–$C_4$-polyalkoxyl-$C_2$–$C_4$-alkyl and cycloalkyl which has 3–6 ring atoms, and which can be interrupted once or twice by at least one of oxygen and sulphur atoms, each of these substituents being optionally substituted by fluorine or chlorine, or represents optionally fluorine- chlorine, bromine-, methyl-, ethyl-, propyl, i-propyl, methoxy, ethoxy, trifluoromethyl-, trifluoromethoxy- or nitro-substituted phenyl, or represents optionally fluorine-, chlorine-, bromine-, methyl-, ethyl-, propyl-, i-propyl, methoxy, ethoxy, trifluoromethyl or trifluoromethoxy-substituted phenyl-$C_1$–$C_3$-alkyl, or represents optionally fluorine-, chlorine-, methyl- or ethyl-substituted phenoxy-$C_1$–$C_4$-alkyl, $R^2$ represents $C_1$–$C_{14}$-alkyl, $C_2$–$C_{14}$-alkenyl, $C_1$–$C_4$-alkoxy-$C_2$–$C_6$-alkyl or $C_1$–$C_4$-polyalkoxy-$C_2$–$C_6$-alkyl each of which is optionally substituted by fluorine or chlorine, or represents phenyl which is optionally substituted by fluorine-, chlorine-, nitro-, methyl-, ethyl-, propyl-, i-propyl-, methoxy-, ethoxy- or trifluoromethyl-, A represents hydrogen, or straight-chain or branched $C_1$–$C_8$-alkyl, $C_3$–$C_4$-alkenyl, $C_3$–$C_4$-alkynyl, $C_1$–$C_6$-alkoxy-$C_2$–$C_4$-alkyl, $C_1$–$C_4$-polyalkoxy-$C_2$–$C_4$-alkyl, $C_1$–$C_6$-alkylthio-$C_2$–$C_4$-alkyl, cycloalkyl which has 3–6 ring atoms and which can be interrupted once or twice by at least one of oxygen and sulphur atoms, each of these substituents being optionally substituted by halogen, B represents hydrogen or straight-chain or branched $C_1$–$C_6$-alkyl or $C_1$–$C_4$-alkoxyalkyl, and $E^{\oplus}$ represents a metal ion equivalent or an ammonium ion.

4. An insecticidal acaricidal or herbicidal composition comprising an insecticidally, acaricidally or herbicidally effective amount of a compound according to claim 1 and a diluent.

5. A method of combating insects, acarids or unwanted vegetation which comprises applying thereto or to a locus from which it is desired to exclude such insects, acarids or vegetation an insecticidally, acaricidally or herbicidally effective amount of a compound according to claim 1.

6. 1-H-3-Aryl-pyrrolidine-2,4-dione-derivative according to claim 1 of the formula:

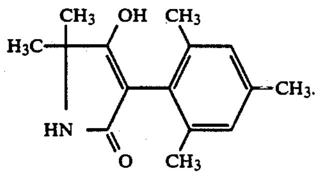

7. 1-H-3-Aryl-pyrrolidine-2,4-dione derivative according to claim 1 of the formula

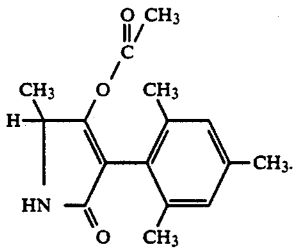

8. 1-H-3-Aryl-pyrrolidine-2,4-dione derivative according to claim 1 of the formula

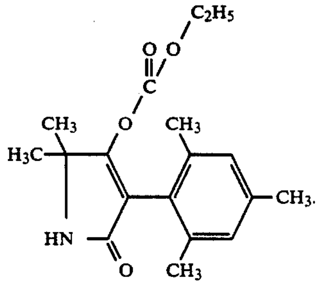

9. 1-H-3-Aryl-pyrrolidine-2,4-dione derivative according to claim 1 of the formula

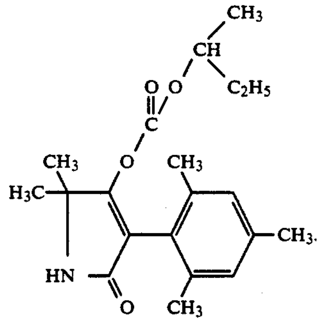

10. 1-H-3-Aryl-pyrrolidine-2,4-dione derivative according to claim 1 of the formula

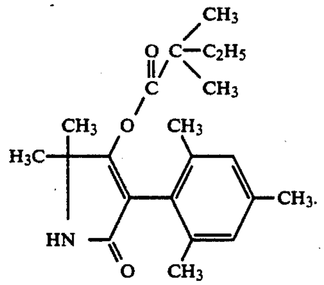

* * * * *